(12) United States Patent
Aliper et al.

(10) Patent No.: US 11,373,732 B2
(45) Date of Patent: Jun. 28, 2022

(54) AGING MARKERS OF HUMAN MICROBIOME AND MICROBIOMIC AGING CLOCK

(71) Applicant: Deep Longevity Limited, Hong Kong (HK)

(72) Inventors: Aleksandr M. Aliper, Moscow (RU); Fedor Galkin, Moscow (RU); Aleksandrs Zavoronkovs, Pak Shek Kok (HK)

(73) Assignee: Deep Longevity Limited, Hong Kong (HK)

( * ) Notice: Subject to any disclaimer, the term of this patent is extended or adjusted under 35 U.S.C. 154(b) by 105 days.

(21) Appl. No.: 16/661,849

(22) Filed: Oct. 23, 2019

(65) Prior Publication Data

US 2020/0075127 A1 Mar. 5, 2020

Related U.S. Application Data

(63) Continuation-in-part of application No. 16/415,855, filed on May 17, 2019, now Pat. No. 10,665,326, which is a continuation-in-part of application No. 16/104,391, filed on Aug. 17, 2018, now Pat. No. 10,325,673, which is a continuation-in-part of application No. 16/044,784, filed on Jul. 25, 2018, now Pat. No. 11,260,078.

(60) Provisional application No. 62/536,658, filed on Jul. 25, 2017, provisional application No. 62/547,061, filed on Aug. 17, 2017, provisional application No. 62/784,953, filed on Dec. 26, 2018, provisional application No. 62/751,397, filed on Oct. 26, 2018.

(51) Int. Cl.
*G16B 40/00* (2019.01)
*G16B 10/00* (2019.01)
*G16H 15/00* (2018.01)
*G06N 20/20* (2019.01)
*G06N 3/08* (2006.01)
*G16B 5/00* (2019.01)

(52) U.S. Cl.
CPC .............. *G16B 40/00* (2019.02); *G06N 3/08* (2013.01); *G06N 20/20* (2019.01); *G16B 5/00* (2019.02); *G16B 10/00* (2019.02); *G16H 15/00* (2018.01)

(58) Field of Classification Search
None
See application file for complete search history.

(56) References Cited

U.S. PATENT DOCUMENTS

| | | |
|---|---|---|
| 8,592,646 B2 | 11/2013 | Portereiko et al. |
| 9,141,756 B1 | 9/2015 | Hillis et al. |
| 10,325,673 B2 | 6/2019 | Aliper et al. |
| 10,665,326 B2 | 5/2020 | Aliper et al. |
| 2019/0030078 A1 | 1/2019 | Aliper et al. |
| 2019/0034581 A1 | 1/2019 | Aliper et al. |
| 2019/0272890 A1 | 9/2019 | Aliper et al. |

FOREIGN PATENT DOCUMENTS

| | | |
|---|---|---|
| CN | 108290059 A | 7/2018 |
| CN | 109415431 A | 3/2019 |
| WO | 2014011735 A1 | 1/2014 |
| WO | 2014091017 | 6/2014 |
| WO | 2016151489 | 9/2016 |
| WO | 2020084536 | 4/2020 |

OTHER PUBLICATIONS

International Search Report and Written Opinion PCT/IB2019/059087, dated Jan. 23, 2020.
Galkin et al. "Human Microbiome aging clocks based on deep learning and tandem of permutation feature importance and accumulated local effects." BIORXIV, Dec. 28, 2018 pp. 1-33.
Lan et al. "Selecting age-related functional characteristics in the human gun microbiome" Microbiome, vol. 1, Jan. 9, 2013, Article No. 2, pp. 1-12.
Pyrkov et al. "Extracting biological age from biomedical data via deep learning; too much of a good thing." Scientific Reports, vol. 8 Mar. 26, 2018, Article No. 5210, pp. 1-11.
Cole et al. "Predicting Age Using Neuroimaging: Innovative Brain Ageing Biomarkers." Trends in Neurosciences vol. 40 No. 12, Dec. 31, 2017 pp. 681-690.
International Search Report and Written Opinion PCT/IB2020/054644, dated Aug. 25, 2020.
Galkin et al. "Biohorology and biomarkers of aging: Current state-of-the-art, challenges and opportunities" Ageing Research Reviews, vol. 60, Jul. 2020, 101050 https://doi.org/10.1016/j.arr.2020.101050.
Donaldson, et al. "Gut biogeography of the bacterial microbiota" Nat Rev Microbiol 14, 20-32 (2016). https://doi.org/10.1038/nrmicro3552.
Viome Life Sciences, Inc. website <https://www.viome.com/products?refcode=vpm_go&campaign=375767564&keyword=viome&msclkid=489dfaf968c6118ff44a9ba655d5d384&utm_sou%E2%80%A6> retrieved Oct. 11, 2021.
DayTwo Inc. website <https://daytwo.com/our-story/> retrieved Oct. 11, 2021.
International Search Report and Written Opinion PCT/IB2021/053430, dated Jun. 28, 2021.

*Primary Examiner* — G Steven Vanni
(74) *Attorney, Agent, or Firm* — Maschoff Brennan; Jonathan M. Benns

(57) ABSTRACT

A method of predicting a phenotypical age of a subject based on a microflora taxonomic profile of a microbiota of the subject can include: isolating a plurality of microorganism nucleic acids of microorganisms from a sample of a microbiota of the subject; analyzing the plurality of microorganism nucleic acids to determine an amount of the microorganisms of the microbiota based on the plurality of microorganism nucleic acids; generating a taxonomic profile of the microbiota of the subject based on the amount of each of the microorganisms; processing the taxonomic profile of the microbiota with a computer configured with a machine learning platform in order to predict the phenotypical age of the subject; generating a report with the predicted phenotypical age of the subject; and providing the report to the subject.

21 Claims, 33 Drawing Sheets

- N(Alistipes_finegoldii) = 3781
- N(Bacteroides_ovatus) = 3796
- N(Bifidobacterium_longum) = 3717
- N(Flavonifractor_plautii) = 3785
- N(Prevotella_intermedia) = 3441
- N([Clostridium]_saccharolyticum) = 3098

- N(Anaerostipes_hadrus) = 3779
- N(Bacteroides_vulgatus) = 3800
- N(Blautia_hansenii) = 3744
- N(Methanobrevibacter_smithii) = 2203
- N(Roseburia_hominis) = 3797
- N([Eubacterium]_eligens) = 3735

- N(Bacteroides_dorei) = 3795
- N(Bifidobacterium_bifidum) = 3429
- N(Eggerthella_lenta) = 3690
- N(Odoribacter_splanchnicus) = 3791
- N(Ruminococcus_bicirculans) = 3756
- N([Eubacterium]_hallii) = 3772

- N(Bacteroides_fragilis) = 3777
- N(Bifidobacterium_breve) = 3592
- N(Escherichia_coli) = 3416
- N(Parabacteroides_distasonis) = 3779
- N(Veillonella_parvula) = 3206
- N([Eubacterium]_rectale) = 3797

Fig. 8Y

- N(Bacteroides_caccae) = 3747
- N(Bacteroides_caecimuris) = 3787
- N(Bacteroides_cellulosilyticus) = 3740
- N(Barnesiella_viscericola) = 3670
- N(Bifidobacterium_adolescentis) = 3483
- N(Bifidobacterium_catenulatum) = 2987
- N(Bifidobacterium_pseudocatenulatum) = 3333
- N(Chryseobacterium_gallinarum) = 2181
- N(Enterococcus_faecalis) = 2411
- N(Faecalibacterium_prausnitzii) = 3798
- N(Fusobacterium_ulcerans) = 158
- N(Lachnoclostridium_sp._YL32) = 3459
- N(Lactococcus_lactis) = 2741
- N(Megasphaera_elsdenii) = 2606
- N(Ornithobacterium_rhinotracheale) = 3619
- N(Parvimonas_micra) = 1618
- N(Shigella_sp._PAMC_28760) = 2308
- N(Streptococcus_gordonii) = 2139
- N([Clostridium]_bolteae) = 3789

Fig. 12

- N(Acidaminococcus_fermentans) = 1529
- N(Acidaminococcus_intestini) = 2129
- N(Bifidobacterium_dentium) = 2152
- N(Desulfovibrio_fairfieldensis) = 583
- N(Dialister_pneumosintes) = 2269
- N(Hafnia_sp_CBA7124) = 410
- N(Lactobacillus_amylovorus) = 1907
- N(Negativicoccus_massiliensis) = 1357
- N(Oxalobacter_formigenes) = 770
- N(Prevotella_jejuni) = 1893
- N(Pseudomonas_aeruginosa) = 228
- N(Rhodococcus_sp_YL-1) = 93
- N(Akkermansia_muciniphila) = 2970

Obtaining nucleic acid information contained within the guts of a cohort of subjects
1402

Filtering the obtained nucleic acid information
1404

Inferring microbe abundance profiles from nucleic acid information
1406

Filtering and normalizing raw abundance profiles
1408

Defining cross-validation (CV) sets
1410

Training neural network models
1412

Assessing model performance
1414

Generating Model Ensemble
1416

Fig. 14

|  | ERR011341 | ERR011167 | ERR011144 | ERR011302 | ERR011216 | ERR011300 | ERR011234 |
|---|---|---|---|---|---|---|---|
| Predicted age, yrs | 60.98 | 53.97 | 63.33 | 58.94 | 56.6 | 54.17 | 53.77 |
| Bacillus coagulans |  |  |  |  |  |  |  |
| Bifidobacterium animalis |  |  |  |  |  |  |  |
| Bifidobacterium bifidum |  |  |  |  |  |  |  |
| Bifidobacterium breve |  |  |  |  |  |  |  |
| Bifidobacterium longum |  |  |  |  |  |  |  |
| Enterococcus faecium |  |  |  |  |  |  |  |
| Lactobacillus acidophilus |  |  |  |  |  |  |  |
| Lactobacillus casei |  |  |  |  |  |  |  |
| Lactobacillus gasseri |  |  |  |  |  |  |  |
| Lactobacillus helveticus |  |  |  |  |  |  |  |
| Lactobacillus plantarum |  |  |  |  |  |  |  |
| Lactobacillus reuteri |  |  |  |  |  |  |  |
| Lactobacillus rhamnosus |  |  |  |  |  |  |  |
| Lactobacillus salivarius |  |  |  |  |  |  |  |
| Propionibacterium freudenreichii |  |  |  |  |  |  |  |
| Streptococcus thermophilus |  |  |  |  |  |  |  |

Fig. 15

| Microbe | Average age change after increasing a microbe's abundance from X% quantile value to Y% quantile value in the population | | | | | | | | | Amplitude, yrs |
|---|---|---|---|---|---|---|---|---|---|---|
|  | 10-20 | 20-30 | 30-40 | 40-50 | 50-60 | 60-70 | 70-80 | 80-90 | 90-95 |  |
| Bacteroides dorei | -0.01 | -0.02 | -0.07 | -0.12 | -0.23 | -0.03 | -0.37 | -1.04 | -0.69 | 2.58 |
| Methanobrevibacter smithii | -0.01 | -0.05 | -0.01 | -0.09 | -0.06 | -0.20 | -0.15 | -0.02 | -0.38 | 0.97 |
| [Eubacterium] rectale | -0.06 | 0.00 | -0.07 | -0.18 | -0.27 | 0.15 | -0.04 | -0.35 | 0.60 | 0.83 |
| [Eubacterium] hallii | -0.11 | -0.04 | -0.03 | -0.09 | 0.03 | -0.17 | 0.08 | -0.31 | -0.01 | 0.66 |
| Bifidobacterium longum | -0.01 | -0.01 | -0.01 | 0.00 | -0.01 | -0.06 | -0.06 | -0.14 | -0.17 | 0.46 |
| Roseburia hominis | -0.04 | -0.03 | -0.02 | -0.04 | 0.00 | -0.01 | -0.03 | -0.12 | -0.02 | 0.29 |

Fig. 16A

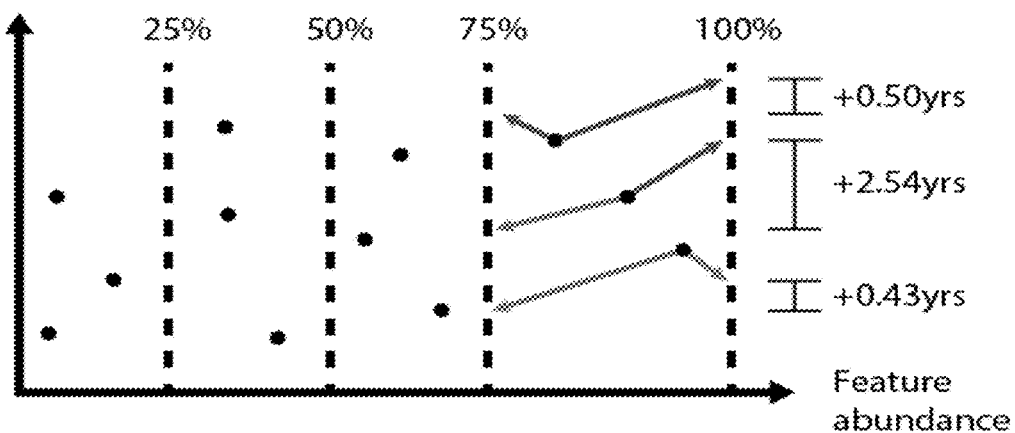
$$LE_{75\text{-}100} = (0.5+2.54+0.43) : 3 = +1.16 \text{ yrs}$$
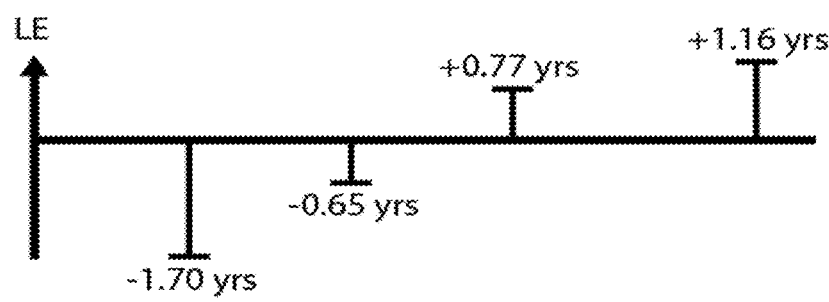
$$ALE_{75\text{-}100} = LE_{0\text{-}25} + LE_{25\text{-}50} + LE_{50\text{-}75} + LE_{75\text{-}100}$$
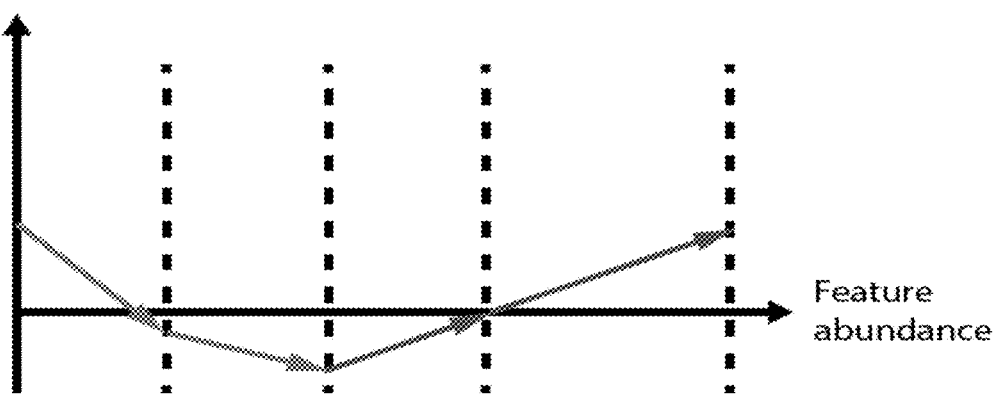
Fig. 19

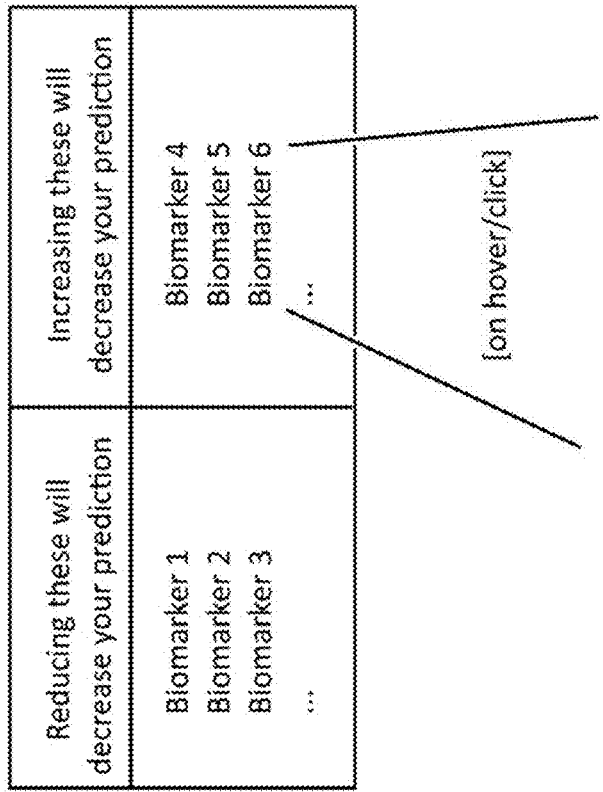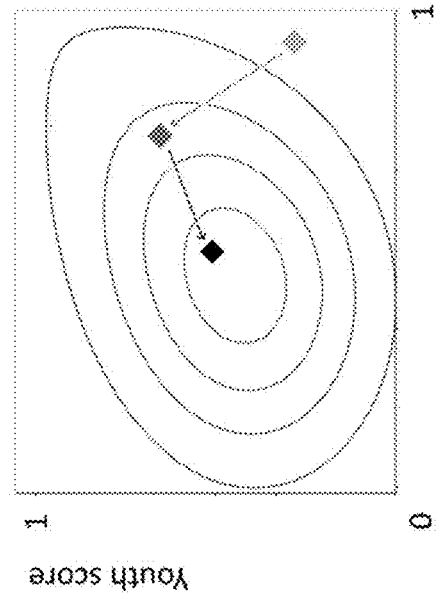
Fig. 22

| Profile | Actual BMI, kg/m2 | Predicted BMI, kg/m2 | Predicted Phenotypic Age, yrs | Chronological Age, yrs |
|---|---|---|---|---|
| ERR1293507 | 26.78 | 27.57 | 60.7 | 58 |
| ERR1293512 | 26.4 | 24.64 | 40.78 | 48 |
| ERR1293514 | 25.11 | 26.27 | 53.27 | 57 |
| ERR1293535 | 22.15 | 26.29 | 64.18 | 68 |
| ERR1293588 | 21.34 | 23.02 | 42.34 | 36 |
| ERR1293591 | 27.21 | 26.05 | 51.56 | 42 |
| ERR1293595 | 30.5 | 27.2 | 57.59 | 67 |
| ERR1293611 | 25.38 | 27.13 | 55.65 | 63 |
| ERR1293627 | 23.62 | 25.58 | 56.18 | 59 |
| ERR1293653 | 22.96 | 24 | 60.89 | 56 |
| ERR1293666 | 23.09 | 26.69 | 53.27 | 48 |
| ERR1293689 | 18.64 | 24.25 | 57.57 | 67 |
| ERR1293704 | 20.47 | 29.22 | 54.32 | 60 |
| ERR1293713 | 33.38 | 28.81 | 47.69 | 49 |
| ERR1293756 | 24.81 | 25.52 | 46.28 | 51 |
| ERR1293805 | 24.36 | 30.1 | 46.8 | 45 |
| ERR1293806 | 23.12 | 27.92 | 60 | 60 |
| ERR1293853 | 22.71 | 24.07 | 49.16 | 56 |
| ERR1293866 | 27.61 | 25.17 | 47.62 | 42 |
| ERR1293899 | 21.52 | 27.37 | 57.63 | 48 |
| ERR1293926 | 22.62 | 25.31 | 42.51 | 45 |
| ERR1727309 | 32.43 | 27.89 | 59.84 | 62 |
| ERR1727315 | 28.58 | 25.77 | 64.93 | 65 |
| ERR1727332 | 33.03 | 29.76 | 58 | 63 |
| ERR1727339 | 32.43 | 28.98 | 58.95 | 62 |
| ERR1727347 | 25.4 | 22.8 | 44.01 | 40 |
| ERR1727368 | 19.98 | 22.82 | 43.14 | 45 |
| ERR1727395 | 30.04 | 26.66 | 54.69 | 55 |
| ERR1727430 | 32.87 | 25.23 | 51.62 | 53 |
| ERR1727487 | 36.58 | 27.4 | 54.8 | 55 |

Fig. 23

AGING MARKERS OF HUMAN MICROBIOME AND MICROBIOMIC AGING CLOCK

CROSS-REFERENCE

This patent application is a continuation-in-part of U.S. Ser. No. 16/415,855 filed May 17, 2019, which is a continuation-in-part of U.S. Ser. No. 16/104,391 filed Aug. 17, 2018 now U.S. Pat. No. 10,325,673, which is a continuation-in-part of U.S. Ser. No. 16/044,784 filed Jul. 25, 2018, which claims benefit of U.S. No. 62/536,658 filed Jul. 25, 2017 and claims benefit of U.S. No. 62/547,061 filed Aug. 17, 2017, wherein each application is incorporated herein by specific reference in its entirety. This patent application also claims priority to U.S. No. 62/784,953 filed Dec. 26, 2018, and claims priority to U.S. No. 62/751,397 filed Oct. 26, 2018, wherein each provisional application is incorporated herein by specific reference in its entirety.

BACKGROUND

There are two commonly accepted definitions of age. In the first one, the chronological age (CA) is simply the actual calendar time a human has been alive. The second one, called biological age (BA) or physiological age, is related to the actual physiological health of the individual. The biological age value is correlated to how well the different organs and regulatory systems of the body perform, and at what extent the general homeostasis at all levels of the organism is being maintained. The measurement of any physiological process inside the body is usually done with a set of predefined biomarkers. A biomarker is a characteristic that is measured as an indicator of normal biological processes, pathogenic processes, or pharmacologic responses to a therapeutic intervention. Biomarkers are developed with the purpose of measuring a very-well defined process within the body. However, aging is a systemic process, and the development of biomarkers for measuring the biological aging of an individual is subject to specific challenges. Indeed, such biomarkers must not only be an objective quantifiable substance and easily measurable characteristics of the biological aging process, but must also be able to take into account that aging is not a single specific process, but rather a suite of changes that are felt across multiple physiological systems.

The chronological age is proportional to the risk of a variety of detrimental conditions and diseases such as arthritis, heart failure, dementia, sarcopenia and others. These associations are discovered in population-wide studies and can be used to promote specific healthcare guidelines and recommended interventions for a group of people. Demographic studies of chronological age are indispensable for officials who rely on them to put together retirement and healthcare policies. However, the concept of chronological age tends to be much less useful on an individual level. A person's life expectancy may deviate significantly from the demographic estimate depending on their condition.

The biological age of an organism concept suggests that various cues can be aggregated into a single numeric score that predicts the risk of aging associated disorders (AAD) and life expectancy more accurately than chronological age. In a sense chronological age and biological age are inverse concepts: AAD risks in a population are a function of chronological age, while biological age is a function of these risks. To illustrate this concept, people routinely estimate the biological age in an attempt to estimate the chronological age by observing their gait, wrinkles, skin pigmentation and voice to conclude that the person in front of them is old or young. On the other hand, determining the chronological age requires verification of the person's official documents (e.g., birth certificate, etc.).

Previously, several attempts have been made to develop a clock for measuring biological aging. Both gene expression (Wolters and Schumacher 2013) and DNA methylation profiles (Horvath 2013) change during aging and may be used as biomarkers of aging as demonstrated previously with the epigenetic clock. Many studies analyzing transcriptomes of biopsies in a variety of diseases indicated that age and sex of the patient had significant effects on gene expression (Chowers et al. 2003) and that there are noticeable changes in gene expression with age in mice (Weindruch et al. 2002) (Park et al. 2009), resulting in development of mouse aging gene expression databases (Zahn et al. 2007) and for humans (Blalock et al. 2003) (Welle et al. 2003) (Park and Prolla 2005) (Hong et al. 2008) (de Magalhães, Curado, and Church 2009). Despite there being numerous biomarkers of aging, developing gut microbiome based biomarkers has presented researchers with a challenge due to huge individual variation in microflora in the same person over time and across different people.

The human gut is colonized by a dense microbial community that is calculated to have $10^{14}$ cells, which is an order of magnitude higher than the number of human cells in a human organism (Suau et al. 1999). Gut microbiota, which are the microorganisms of a particular site such as the gut, is a complex ecosystem that carries multiple important functions in the organism. Apart from being a core element of the digestive system, microbiota regulates immunity, processes xenobiotics, produces important metabolites and even affects higher neural functions (De Palma et al. 2017; Rowland et al. 2018; Wu and Wu 2012).

The influence, however, is not one-sided. The microbiota is not simply determining certain host characteristics, but is rather constantly reacting to signals from the host via multiple feedback loops (Lozupone et al. 2012). Some of these feedback loops have been found to be reflected in the microbiota composition. Although this example demonstrates a clearly deleterious microflora succession, a gut microbiota ecosystem normally changes throughout an individual's life. Some of these changes reflect individual lifestyle, while others seem to be more general for whole populations.

Metagenomic studies have provided valuable insights into how microflora in the gut microbiota progress with age. Such studies show that gut colonization happens during birth with the bacteria living in the birth canal. The "pioneer microbiome" includes facultative aerobes (*Escherichia* and *Enterococcus*), that gets replaced after breast feeding with obligate anaerobes (e.g. *Bifidobacterium infantis*) (Perez-Muñoz et al. 2017). Weaning leads to another community shift towards more typically adult microbiomes (Tanaka and Nakayama 2017). These early stages of colonization are extremely important as normal infant intestinal microbiota promotes intestinal mucus formation, prevents pathogen blooming, and regulates T-cells (Buford 2017).

Although infant microbiome succession is well studied and can be used to assess the risks of various health conditions, its transition to adult microbiome is understood less clearly. More so, composition variability attributed to geographic location, medical history, diet and other factors make it hard to analyze adult microbiomes as fruitfully as those of infants. Age-related studies of human microbiome have failed to produce a straightforward theory of gut microflora aging. Certain studies indicate decreasing biodiversity in the elderly gut microflora (Garcia-Peña et al. 2017; Hopkins and Macfarlane 2002). However, that is not the case for all data sets and old healthy people may have microbiomes as diverse as in younger people (Bian et al. 2017; Maffei et al. 2017). Other findings include changes in specific taxa (e.g., changes in strains, species, or genus or other taxonomic category) amount or changes in percentage of one or more specific microorganisms (e.g., strains, species, or genus or other taxonomic category) of a total microbiota in aging microbiota. For example, bacterial genara, such as *Bacteroides, Bifidobacterium, Blautia, Lactobacilli*, or *Ruminococcus* have been shown to decrease in the elderly, while *Clostridium, Escherichia, Streptococci, Enterobacteria* have been shown to increase in the elderly (O'Toole and Jeffery 2015; Woodmansey et al. 2004). However, these patterns are not strictly established as results may vary greatly among different studies.

So far biologists seem to have separated gut microbiome into three chronological states: child, adult and elderly microbiomes, which are divided by an unclear set of rules. Among them, adult microbiome is the least definitive term. It has no established succession stages as in newborns and does not normally reflect gradient detrimental processes typical for an old organism.

Therefore, it would be advantageous to design a biological clock model that can estimate a biological age based on gut microbiota. Additionally, it would be advantageous to use the biological clock model to predict the biological age based on gut microbiota. Moreover, it would be advantageous to have an application platform that allows users to receive information based on their gut microbiota and determined biological age.

SUMMARY

In some embodiments, a method of predicting a chronological age (e.g., predicted chronological age is the biological age) and/or phenotypical age (e.g., the phenotypical age is the biological age based on the phenotype of the microbiota of the subject) of a subject based on a microflora taxonomic profile of a microbiota of the subject can include: isolating a plurality of microorganism nucleic acids of microorganisms from a sample of a microbiota of the subject; analyzing the plurality of microorganism nucleic acids to determine an amount of the microorganisms of the microbiota based on the plurality of microorganism nucleic acids; generating a taxonomic profile of the microbiota of the subject based on the amount of each of the microorganisms; processing the taxonomic profile of the microbiota with a computer configured with a machine learning platform (e.g., machine learning platform includes one or more deep neural networks) in order to predict the chronological age and/or phenotypical age of the subject; generating a report with the predicted chronological age and/or phenotypical age of the subject; and providing the report to the subject.

The methods predict what the chronological age of a subject could be based on the calculated phenotypic age of the microbiota of the subject. This results in the calculated phenotypic age being used as the predicted chronological age of the subject; however, it is likely that the calculated phenotypic age may be different from the actual chronological age that is measured from the birthdate of the subject. The predicted chronological age, which is the phenotypic age, is referred to herein as the biological age of the subject. As such, the predicted phenotypic age of the microbiota of the subject is determined and defined as the predicted biological age of the subject. Accordingly, the biological aging clock based on the microbiota can be used to obtain a predicted biological age of the subject. Thus, reference to the predicted chronological age or the phenotypic age is made by discussion of the predicted biological age.

In some embodiments, a method of predicting a biological age of a subject can include: obtaining a taxonomic profile of a microbiota of the subject based on an amount of each of microorganism in a sample of microbiota of the subject; processing the taxonomic profile of the microbiota with a computer configured with a machine learning platform; predicting the biological age of the subject based on output of the processed taxonomic profile; generating a report with the predicted biological age of the subject; and providing the report to the subject. In some aspects, the method can include: receiving a plurality of microorganism nucleic acids of microorganisms from the sample of the microbiota of the subject; and analyzing the plurality of microorganism nucleic acids to determine an amount of the microorganisms of the microbiota based on the plurality of microorganism nucleic acids. In some aspects, the method can include generating the taxonomic profile of the microbiota of the subject based on the amount of each of the microorganisms in the sample. In some aspects, the taxonomic profile includes a specific group of microorganisms as defined herein, such as the specific group of microorganisms including: Group 314; Group 95; Group 76; Group 39; Group 41; Group 16; Geroprotective Group; Progeroid Group; or combinations thereof. In some aspects, the specific group of microorganisms includes: Group 39; or Group 41. In some aspects, the method can include: receiving the biological sample having the microbiota of the subject; and isolating the plurality of microorganism nucleic acids of microorganisms from the sample of the microbiota of the subject.

In some embodiments, the method can include processing the taxonomic profile of the microbiota in a manner that results in defining one or more of the following: a relative amount of the microorganisms of total microorganisms in the microbiota; a relative amount of each microorganism; and/or a relative amount species level taxonomic profile for each species of the microorganisms. In some aspects, the method can include generating a species level taxonomic profile of the microbiota of the subject based on the amount of each of the microorganisms. In some aspects, each taxonomic profile is based on whole metagenome reads.

In some embodiments, the method can include: accessing a database with a plurality of reference microorganism taxonomic profiles linked to a biological age of a plurality of reference subjects; and comparing the taxonomic profile of the microbiota of the subject with the plurality of reference microorganism taxonomic profiles.

In some aspects, the method can include: determining an altered taxonomic profile to reduce the predicted biological age of the subject into a younger predicted biological age range than the predicted biological age of the subject; and including the altered taxonomic profile in the report provided to the subject. In some aspects, the method can include: determining a treatment method for obtaining the altered taxonomic profile of the subject to obtain a younger predicted biological age range in the subject; and providing the treatment method in the report. In some aspects, the method includes: determining at least one microorganism whose change in amount provides an altered taxonomic profile to reduce the predicted biological age of the subject into a younger predicted biological age range than the predicted biological age of the subject; and providing information about the determined at least one microorganism in the report.

In some embodiments, the method can include: analyzing a plurality of microorganism nucleic acids from a plurality of reference subjects, wherein a plurality of microorganism nucleic acids are analyzed for each subject; determining an amount of the microorganisms of the microbiota of each reference subject based on the plurality of microorganism nucleic acids; generating a taxonomic profile of the microbiota of each reference subject based on the amount of each of the microorganisms; processing the taxonomic profile of the microbiota of each reference subject with a computer configured with a machine learning platform in order to predict the biological age of each reference subject; and saving the predicted biological age and associated taxonomic profile for each reference subject in a reference database with the predicted biological age associated with the taxonomic profile of the microbiota for each reference subject. In some aspects, the method includes: generating a computer program product stored on a tangible, non-transitory memory device of a computer that when executed cause the computer to: access the reference database; compare the subject's taxonomic profile with the reference database; provide information on at least one specific microorganism that modulates the predicted biological age associated of the subject; generate the report with the provided information; and cause the report to be provided to the subject.

In some embodiments, the method can include: creating input vectors based on the taxonomic profile; inputting the input vectors into the machine learning platform; generating a predicted biological aging clock of the microbiota based on the input vectors by the machine learning platform, wherein the biological aging clock is specific to the microbiota; and preparing the report to include the biological aging clock and identifies the predicted biological age of the subject based on the microbiota.

In some embodiments, the method can include: providing an internet application to a computer of the subject; receiving input from the internet application to obtain the report for the subject; associating the generated report with the subject; and providing the generated report to internet application on the computer. In some aspects, the method can include: providing a selectable selection to the internet application; receiving a selected selection input from the internet application, the selected selection input being obtained from the subject selecting the selectable selection; identify information regarding the predicted biological age from the selected selection input; and providing the information regarding the predicted biological age to the internet application on the computer of the subject. In some embodiments, the method can include at least one of: providing information about the types of microorganisms in the microbiota; providing dietary information about how to increase specific microorganisms of the microbiota; providing dietary information about how to decrease specific microorganisms of the microbiota; providing health information about microbiota for a defined age range for a reference group of microbiota; providing information about reference subjects having similar microbiota taxonomic profiles; or providing a sequence of a plurality of predicted biological ages for the subject, wherein the providing is over the internet to the internet application on the computer of the subject.

In some embodiments, a method of creating a microbiomic aging clock can include: obtaining microbiota nucleic acid information for a plurality of subjects; determining abundance profiles of the abundance of microbes of the microbiota based on the nucleic acid information for each subject; training a plurality of neural network models with the abundance profiles; assessing performance of the plurality of trained neural network models; identifying trained neural network models having an error below an error threshold; combining the identified trained neural network models into an ensemble model; and providing the ensemble model. In some aspects, the method can include: filtering the microbiota nucleic acid information prior to determining abundance profiles; filtering and normalizing the abundance profiles; and defining cross-validation sets of data, wherein the training uses the cross-validation sets of data with the filtered and normalized abundance profiles.

In some embodiments, a method of assessing effect of a dietary change on a predicted biological age of a subject can include: obtaining a first biological age of a subject based on a first microflora taxonomic profile of a microbiota of the subject, the method comprising: providing instructions to the subject to change their diet by changing consumption of at least one substance; obtaining a second biological age of the subject based on a second microflora taxonomic profile of the microbiota of the subject; comparing the first biological age with the second biological age by determining a difference between the first microflora taxonomic profile and the second microflora taxonomic profile; identifying at least one microorganism with a change in abundance from the first microflora taxonomic profile to the second microflora taxonomic profile; and providing a report with the difference between the first biological age and second biological age, and with the identified at least one microorganism having the change in abundance. In some aspects, the instructions include at least one of: increasing consumption of a substance that increases microorganisms associated with a seno-positive effect; decrease consumption of a substance that increases microorganisms associated with a seno-negative effect; increase consumption of a substance that decreases microorganisms associated with seno-negative effect; or decreasing consumption of a substance that decreases microorganisms associated with seno-positive effect.

In some embodiments, a method of predicting a body mass index (BMI) of a subject can include: obtaining a taxonomic profile of a microbiota of the subject based on an amount of each of microorganism in a sample of microbiota of the subject; processing the taxonomic profile of the microbiota with a computer configured with a machine learning platform trained with taxonomic profile data with known BMI values; predicting the BMI of the subject based on output of the processed taxonomic profile; generating a report with the predicted BMI of the subject; and providing the report to the subject.

In some embodiments, a method can include: creating input vectors based on the taxonomic profile and associated BMI; inputting the input vectors into the machine learning platform; generating a predicted BMI clock of the microbiota based on the input vectors by the machine learning platform, wherein the BMI clock is specific to the microbiota; and preparing the report to include the BMI clock and identifies the predicted BMI of the subject based on the microbiota.

In some embodiments, a method of predicting a disease state of a subject can include: obtaining a taxonomic profile of a microbiota of the subject based on an amount of each of microorganism in a sample of microbiota of the subject; processing the taxonomic profile of the microbiota with a computer configured with a machine learning platform trained with taxonomic profile data with a known disease state; predicting the disease state of the subject based on output of the processed taxonomic profile; generating a report with the predicted disease state of the subject; and providing the report to the subject. In some aspects, the method can include: creating input vectors based on the taxonomic profile and associated known disease state; inputting the input vectors into the machine learning platform; generating a predicted disease state clock of the microbiota based on the input vectors by the machine learning platform, wherein the disease state clock is specific to the microbiota; and preparing the report to include the disease state clock and identifies the predicted disease state of the subject based on the microbiota. In some aspects, the known disease state is Type-I Diabetes; however, it should be recognized that the model can be trained with microbiota taxonomic profiles associated with disease states of other diseases. Thus, the model can be trained for any type of disease with data of the microbiota associated with the disease type, and then subjects can provide their microbiota nucleic aids for analysis to determine if they have a defined disease state.

In some embodiments, a method of generating a synthetic taxonomic profile can include: providing a microbiomic aging clock that has been trained with abundance profiles of the abundance of the microbiota of a plurality of subjects based on the nucleic acid information for each subject; generating at least one synthetic taxonomic profile; and generating a report for the at least one synthetic taxonomic profile. In some aspects, the method can include: inputting criteria into the microbiomic aging clock for a synthetic subject having a defined phenotype; and generating the synthetic taxonomic profile for the synthetic subject based on the defined phenotype.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 12 shows the calculated ALE values for another group of microorganisms.

FIG. 13 shows the calculated ALE values for another group of microorganisms.

FIG. 14 shows a method of constructing a microbiomic aging clock.

FIG. 15 includes data that shows that different people can have both positive and negative effects on the predicted age from the same bacterium by using the biological clock model.

FIG. 16A shows average changes in the predicted while shifting microbes' abundance within the subsample of people older than 50 years old.

FIG. 19 shows training a reliable aging clock model, and applying accumulated local effect (ALE) to the model to measure its responses to changes in feature values.

FIG. 22 illustrates an example of an application that can perform the methods described herein.

FIG. 23 includes an example of 30 profiles that shows the profile ID, actual BMI, Predicted BMI, Predicted Phenotypic Age, and the actual Chronological Age.

DETAILED DESCRIPTION

Figure 1:
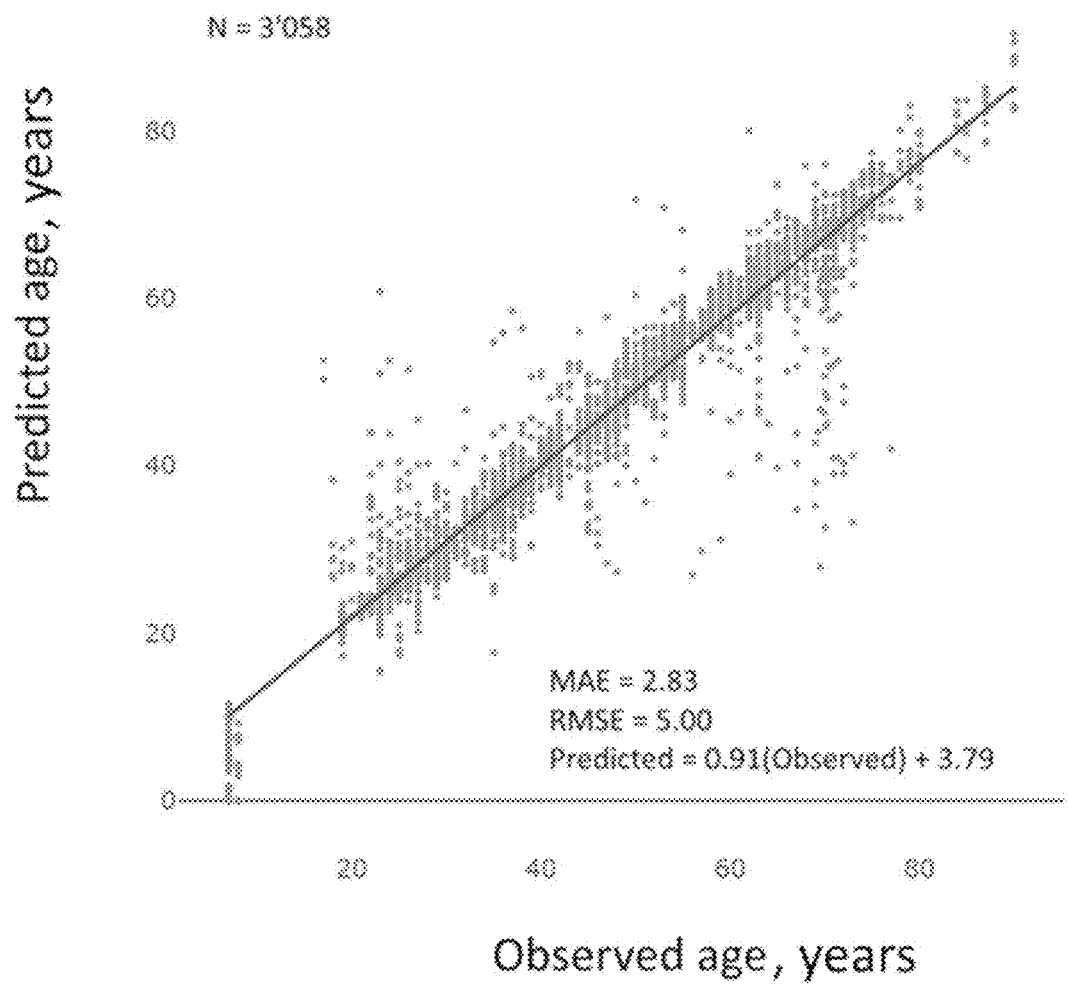
FIG. 1 shows predicted age versus an observed age in a DFS model.

In the following detailed description, of. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to metagenome biomarkers of human biological aging, which may include microflora of a microbiota and the microbiomes thereof. More specifically, the invention relates to biomarkers included in gut microbiome profiles of subjects, which can be processed and analyzed with computers (e.g., machine learning, artificial intelligence, deep learning, deep neural networks, etc.) to provide metrics and estimated biological ages (e.g., an estimate or prediction of an actual chronological age without knowing the true chronological age) of humans with microbiome aging clocks. More specifically, microbiome aging clocks are generated for individuals based on the gut microbiome profiles or other microbiota locations in a subject, which can be provided for various uses, such as those described herein, including a predicted chronological age or phenotypical age (e.g., biological age) of the individual subject. As used herein, the predicted chronological age is not the true chronological age, but instead the predicted chronological age is the calculated phenotypic age. The phenotypic age of the microbiome refers to the biological age of the subject as presented by the gut microbiota phenotype of the subject.

In some embodiments, machine learning and deep learning techniques are used to estimate biological age of humans or other subjects by their metagenomic microbiome profiles. The machine learning platform may include one or more deep neural networks.

In some aspects, the machine learning platform comprises one or more generative adversarial networks. In some aspects, the machine learning platform comprises an adversarial autoencoder architecture. In some aspects, the machine learning platform comprises a feature importance analysis for ranking genes, gene sets or taxonomic features and their sets by their importance in age prediction.

In some embodiments, the invention can be utilized to access the biological age (BA) as predicted by the computing based on the gut microbiome profiles or other microbiota microbiome profiles, and then produce interventions against biological aging. As such, the gut or other location microbiome profiles or can be used to determine an intervention to reduce aging in the individual subject.

In some embodiments, a method to estimate a subject's predicted chronological age (CA) based on their microflora taxonomic profile is provided. The method can assess the importance of specific microorganism taxa in the aging of the subject. The true chronological age can be compared to the predicted value (e.g., biological age) to assess the health of the subject.

In some embodiments, the method can consider the chronological age and the biological age. This mix of chronological age and the biological age can be used with aging clocks in biogerontology, such as the biological aging clocks described herein. In some aspects, the biological aging clock is a mathematical model that takes in a list of aging biomarkers, such as one of the specific Groups defined herein, and produces a chronological age estimate. The biological aging clock model can be verified on healthy individuals (e.g., trained), and once trained is then applied to people to determine the biological age of each subject. For example, the people that have their biological age assessed can be normal healthy people, or those people that are expected to age differently by receiving geroprotective interventions or suffering from an AAD. The biological aging clock model shows accurate predictions for healthy people and reacts to age-altering conditions, thereby it is regarded as a reliable way to estimate biological age in humans, such as for the sake of scientific progress.

The description herein provides a way to determine the most significant features in the context of aging for any type of biological data with limited dimensionality (e.g. transcriptomic, proteomic, biochemical, epigenomic, metagenomic). This method allows to determine which features carry the most influence on biological age estimation and use them to design the biogerontological tools and interventions.

While the subject is often a human, other mammals, such as farm animals (e.g., cows, horses, chickens, turkeys, pigs, etc.), dogs, cats, as well as other types of animals, such as birds, reptiles, insects etc., can also be used as subjects. Accordingly, the invention can be used to screen the health of individual subjects or overall public health for a number of subjects whether in a common location, such as a city, or with a common heritage or other linking basis. The determined biological age can then be used to provide medical advice to the subject or group of subjects. The biological age can also be used to develop consumer products and services to beneficially affect the gut microbiota of a subject. While the microflora of a gut microbiota can be used, the microflora of other microbiota can be used, such locations of the microbiota can include mouth, skin, eyes, ears, genitals, specific organs, or other locations than the gut.

In some embodiments, the method of obtaining the sample can be standard procedures. The samples of can include a gut microbiome or a non-gut microbiome (e.g. urogenital, cutaneous, oral, or others listed). The sample can then be processed to obtain a nucleic acids (e.g., DNA, RNA, of any form) profile. Also, a protein profile may be used. The profile can then be analyzed as nucleic acids or proteins are commonly analyzed for amounts or percentages or other value indicates to characterize the microflora profile of the sample.

The samples can be obtained from any biological sample of a subject, whether taken from the surface of a subject or from an internal region of the subject. For example, the sample of gut metagenome can be obtained either with stool collection or biopsy. Accordingly, blood samples, urine samples, sweat samples, hair samples, mucus samples, semen samples, vaginal secretion samples, or other bodily fluid or excretion sample can be used.

In some embodiments, a method of predicting a subject's biological age based on their microbiome taxonomic profile is provided. The method can include: (a) obtaining or isolating microbial nucleic acids (e.g., DNA, RNA, of any type) from a sample of the subject's metagenomics microbiome; (b) determining or estimating relative or absolute amounts or percentages or other value of a plurality of different microorganisms (e.g., strain, species, or genus level microbial taxa categories) in the sample (e.g., by using whole genome sequencing ("WGS") techniques) to produce a taxonomic profile of the microorganisms, such as the microflora of a specific microbiota (e.g., gut, mouth, skin, eyes, ears, genitals, urethra, anus, colon, intestines, vagina, specific organs, or other locations); and (c) processing the taxonomic profile with a machine learning platform in order to predict the age of the subject (e.g., sample donor). The predicted age can be the subject's biological age based on their microbiome taxonomic profile as processed by the machine learning platform. In some aspects, the determined phenotypic or biological age can be assigned to the subject. In some aspects, the sample can may be processed and the nucleic acid information obtained. The method can operate by receiving the nucleic acid information and then performing the computations described herein.

The present technology and protocols often is described in connection to a single subject; however, the protocols can be applied to multiple subjects. This can include assessing or otherwise analyzing multiple taxonomic profile or metagenomics profiles of multiple subjects at the same time. Such can include comparing the profiles of different subjects with each other and/or against standard profiles (e.g., having: (1) lower biological age than real age; (2) same biological age as real age; and/or (3) higher biological age than real age). The resulting data can then be included in reports for reporting to the subject, which reports can include identifying proposed dietary plans, treatment plans, lifestyle plans, exercise plans, or other plans. The subject wanting a lower biological age or in need thereof can then utilize the one or more plans that are reported to them.

In some embodiments, the protocol can include creating a metagenomics biological clock and the use of it to predict a subject's biological age. Data related to metagenomics taxonomical profiles based on genetic analyses correlated with actual ages of subjects can be used to train computer models (e.g., the machine learning and deep learning techniques with one or more deep neural networks). The data can be input into such computer models to train the computer models to correlate the data with ages, and thereby be able to receive data and correlate the data with the chronological age and/or phenotypic age. For example, the model can be trained such that when a certain data set is used for analysis, the model can provide output of a predicted age based on the biomarkers and taxonomic profiles matching with certain ages. The model outputs the predicted phenotypic age based on the taxonomic profile. The metagenomics biological clock can also be used to produce healthcare guidelines, which can be based on the collective data of taxonomic profiles for a plurality of subjects. For example, the protocol can include loading hundreds to thousands of metagenomics taxonomical profiles into the model in order to get the information on how the population is doing in general, whether the population is older than expected (e.g., older than actual age). The data can then be studied to determine whether certain diets cause increases in phenotypic age over real age. As such, the data can be analyzed to determine whether reducing dietary sugar could make the subjects phenotypically younger (i.e., biologically younger).

In some embodiments, the different microorganisms can include two or more of the following microorganisms, where each microorganism is defined herein by the microorganism number provided in parentheses: *Bacteroides vulgatus* (1), *Fusobacterium ulcerans* (2), *Bacteroides ovatus* (3), *Bifidobacterium bifidum* (4), *Chryseobacterium gallinarum* (5), [*Eubacterium*] *rectale* (6), [*Eubacterium*] *hallii* (7), *Bifidobacterium longum* (8), *Alistipes finegoldii* (9), *Faecalibacterium prausnitzii* (10), [*Clostridium*] *saccharolyticum* (11), *Ornithobacterium rhinotracheale* (12), *Bacteroides dorei* (13), *Parvimonas micra* (14), *Lactococcus lactis* (15), *Bifidobacterium adolescentis* (16), *Bifidobacterium catenulatum* (17), *Enterococcus faecalis* (18), [*Eubacterium*] *eligens* (19), *Roseburia hominis* (20), *Lachnoclostridium* sp. YL32 (21), *Bacteroides cellulosilyticus* (22), *Akkermansia muciniphila* (23), *Parabacteroides distasonis* (24), *Bifidobacterium pseudocatenulatum* (25), *Bacteroides caccae* (26), *Ruminococcus bicirculans* (27), *Methanobrevibacter smithii* (28), *Escherichia coli* (29), *Prevotella intermedia* (30), *Megasphaera elsdenii* (31), [*Clostridium*] *bolteae* (32), *Flavonifractor plautii* (33), *Streptococcus gordonii* (34), *Barnesiella viscericola* (35), *Anaerostipes hadrus* (36), *Bacteroides caecimuris* (37), *Eggerthella lenta* (38), *Odoribacter splanchnicus* (39), *Bacteroides fragilis* (40), *Shigella* sp. PAMC 28760 (41), *Rhodococcus* sp. YL-1 (42), *Acidaminococcus fermentans* (43), *Campylobacter jejuni* (44), *Streptococcus parasanguinis* (45), *Bifidobacterium angulatum* (46), *Negativicoccus massiliensis* (47), *Veillonella parvula* (48), *Streptococcus salivarius* (49), *Streptococcus anginosus* (50), *Victivallales bacterium* CCUG 44730 (51), *Parabacteroides* sp. CTO6 (52), *Streptococcus thermophiles* (53), *Bacteroides salanitronis* (54), *Hafnia* sp. CBA7124 (55), *Christensenella massiliensis* (56), *Bacteroides thetaiotaomicron* (57), *Bifidobacterium dentium* (58), *Cloacibacillus porcorum* (59), *Streptococcus constellatus* (60), *Haemophilus parainfluenzae* (61), *Pseudomonas aeruginosa* (62), *Intestinimonas butyriciproducens* (63), *Clostridium* sp. SY8519 (64), *Desulfovibrio fairfieldensis* (65), *Blautia hansenii* (66), *Prevotella jejuni* (67), *Lactobacillus amylovorus* (68), *Oxalobacter formigenes* (69), *Adlercreutzia equolifaciens* (70), *Acidaminococcus intestine* (71), *Dialister pneumosintes* (72), *Erysipelotrichaceae bacterium* 146 (73), *Comamonas kerstersii* (74), *Enterococcus faecium* (75), *Coriobacteriaceae bacterium* 68-1-3 (76), *Bifidobacterium breve* (77), *Collinsella aerofaciens* (78), *Mordavella* sp. Marseille-P3756 (79), *Bacteroides helcogenes* (80), *Prevotella melaninogenica* (81), *Lactobacillus ruminis* (82), *Rothia mucilaginosa* (83), *Turicibacter* sp. H121 (84), *Klebsiella* sp. 2N3 (85), *Hafnia alvei* (86), *Clostridium cochlearium* (87), *Gordonibacter urolithinfaciens* (88), *Propionibacterium freudenreichii* (89), *Lactobacillus reuteri* (90), *Eggerthella* sp. YY7918 (91), *Streptococcus acidominimus* (92), *Campylobacter coli* (93), *Chryseobacterium taklimakanense* (94), and/or *Porphyromonas asaccharolytica* (95) as well as combinations thereof. In some aspects, the microorganisms of this paragraph are a specific group, and are used as a specific combination, herein "Group 95," which designates the 95 specific members in the group. Accordingly, each of the 95 different types of recited microorganisms is present in Group 95.

In some embodiments, the methods can include the microorganism set or biomarker set includes the following group: *Bacteroides vulgatus* (1), *Comamonas kerstersii* (2), *Bifidobacterium bifidum* (3), *Rhodococcus* sp. YL-1 (4), *Alistipes finegoldii* (5), *Bacteroides ovatus* (6), *Chryseobacterium gallinarum* (7), *Desulfovibrio fairfieldensis* (8), *Campylobacter jejuni* (9), *Bifidobacterium longum* (10), *Odoribacter splanchnicus* (11), *Bacteroides caecimuris* (12), *Oxalobacter formigenes* (13), *Christensenella massiliensis* (14), *Ornithobacterium rhinotracheale* (15), *Parabacteroides* sp. CT06 (16), *Prevotella jejuni* (17), *Flavonifractor plautii* (18), *Bacteroides dorei* (19), *Streptococcus salivarius* (20), *Haemophilus parainfluenzae* (21), *Prevotella melaninogenica* (22), *Bacteroides thetaiotaomicron* (23), *Chryseobacterium taklimakanense* (24), *Eggerthella* sp. YY7918 (25), *Propionibacterium freudenreichii* (26), *Clostridium* sp. SY8519 (27), *Intestinimonas butyriciproducens* (28), *Pseudomonas aeruginosa* (29), *Faecalibacterium prausnitzii* (30), *Hafnia* sp. CBA7124 (31), *Eggerthella lenta* (32), *Acidaminococcus fermentans* (33), *Lactobacillus reuteri* (34), *Lactococcus lactis* (35), [*Eubacterium*] *eligens* (36), [*Clostridium*] *bolteae* (37), [*Clostridium*] *saccharolyticum* (38), [*Eubacterium*] *hallii* (39). In some aspects, the microorganisms of this paragraph are a specific group, and are used as a specific combination, herein "Group 39," which designates the 39 specific members in the group. Accordingly, each of the 39 different types of recited microorganisms is present in Group 39.

In some embodiments, the specific set of features derived from gut metagenomic information includes the following microbial species' relative abundance: *Bacteroides dorei* (1), *Akkermansia muciniphila* (2), *Bacteroides cellulosilyticus* (3), *Shigella* sp. PAMC 28760 (4), [*Eubacterium*] *rectale* (5), *Ruminococcus bicirculans* (6), *Methanobrevibacter smithii* (7), [*Eubacterium*] *eligens* (8), *Bifidobacterium bifidum* (9), *Bacteroides vulgatus* (10), *Bifidobacterium adolescentis* (11), *Bacteroides thetaiotaomicron* (12), *Bacteroi-* des ovatus (13), Bacteroides caccae (14), Bacteroides caecimuris (15), Bifidobacterium longum (16), Megasphaera elsdenii (17), Escherichia coli (18), Parabacteroides distasonis (19), Parabacteroides sp. CTO6 (20), [Eubacterium] hallii (21), Flavonifractor plautii (22), Gordonibacter urolithinfaciens (23), [Clostridium] bolteae (24), Bifidobacterium pseudocatenulatum (25), Streptococcus salivarius (26), Streptococcus thermophilus (27), Ornithobacterium rhinotracheale (28), Alistipes finegoldii (29), Coriobacteriaceae bacterium 68-1-3 (30), Campylobacter jejuni (31), Streptococcus parasanguinis (32), Roseburia hominis (33), Acidaminococcus fermentans (34), Streptococcus equinus (35), Chryseobacterium gallinarum (36), Eggerthella lenta (37), Faecalibacterium prausnitzii (38), Lactobacillus amylophilus (39), [Clostridium] saccharolyticum (40), and Bacteroides fragilis (41). In some aspects, the microorganisms of this paragraph are a specific group, and are used as a specific combination, herein "Group 41," which designates the 41 specific members in the group. Accordingly, each of the 41 different types of recited microorganisms is present in Group 41.

Figure 21:
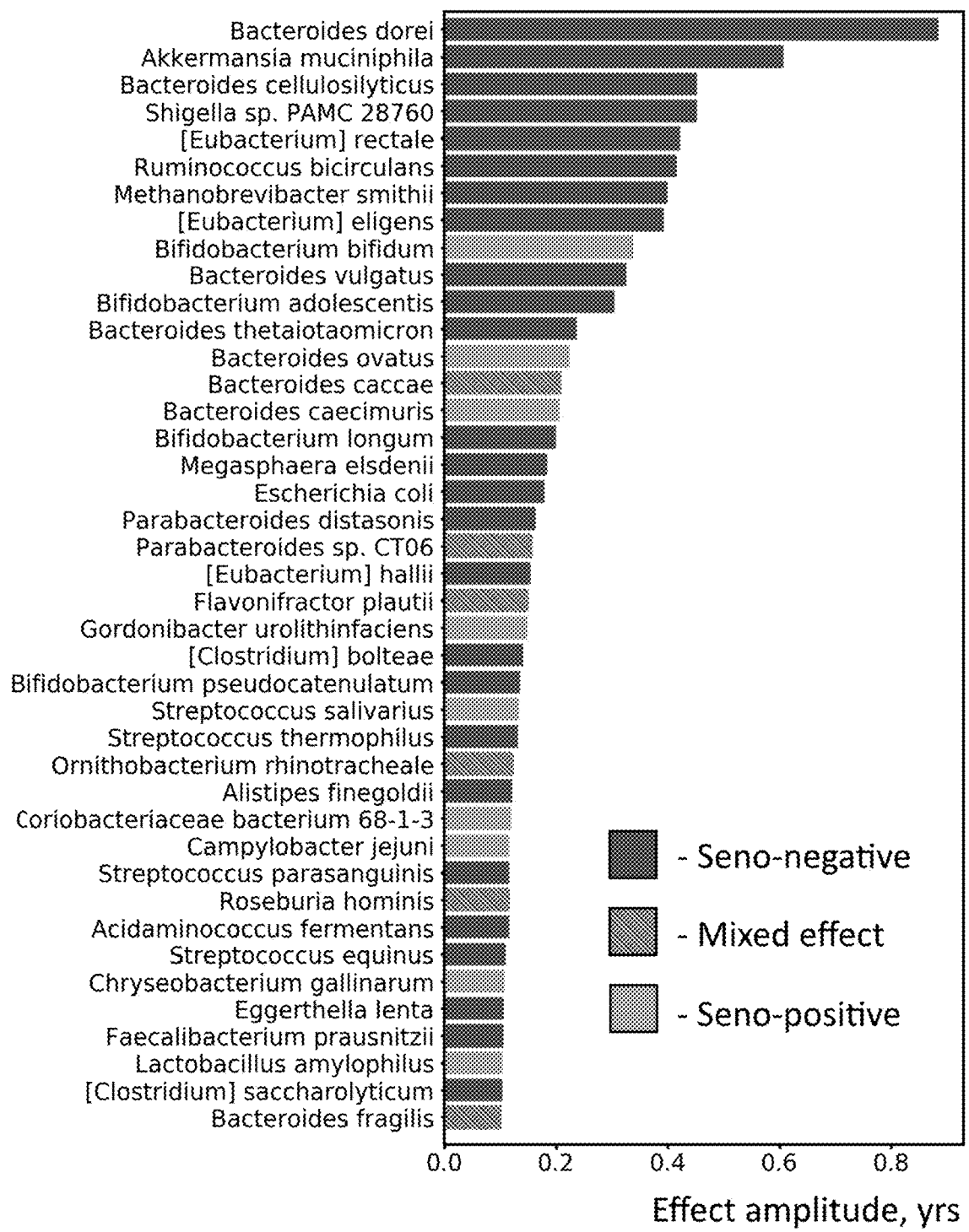
FIG. 21 shows the 41 microbial features that show the most prominent amplitude with determined seno-status.

FIG. 21 shows the 41 microbial features that show the most prominent amplitude with determined seno-status. A DNN model was trained to predict donors' age based on their microflora taxonomic profiles. ALE-analysis (described herein) showed that 41 features in the model can change the prediction by more than 0.1 years. Out of these 41 features, 9 of them are seno-positive (are associated with increased predicted age, lightest box), 26 of them are seno-negative (associated with reduced predicted age, darkest box) and 6 do not display monotonic behavior (e.g., hatched box). These 41 taxa can be used as biomarkers of aging in certain embodiments to reduce the cost and complexity of the full taxonomic microbiota analysis. It should be recognized that the other Groups of microbiota can also be similarly analyzed and used.

These microbial species can be treated as biomarkers of human age to develop hypotheses regarding the nature of aging or design consumer products (such as prebiotics and probiotics) to affect aging as well as diagnostics systems using this set of features.

Figure 4:
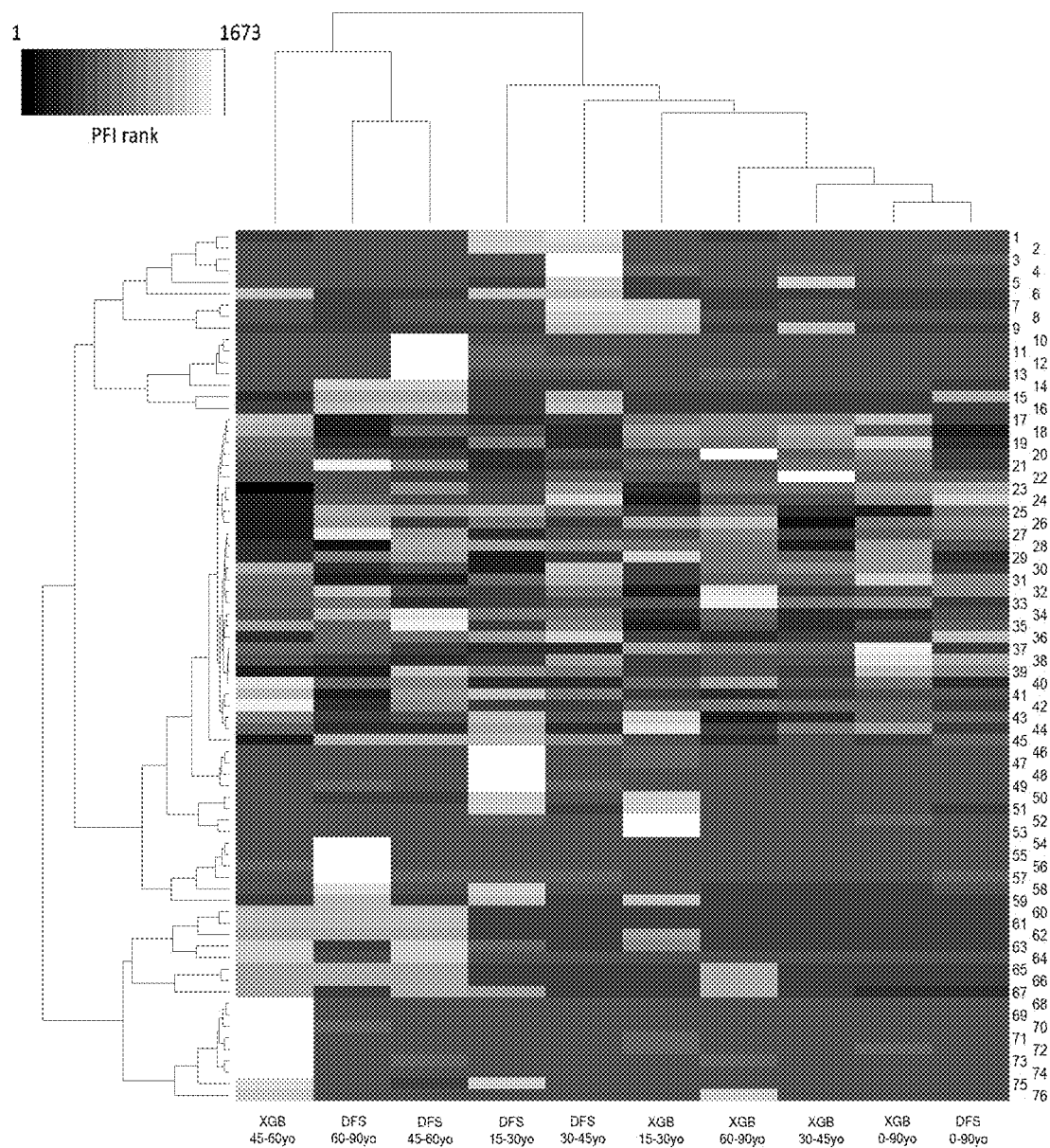
FIG. 4 shows an importance rank comparison of 74 microbial taxa assigned by DFS and XGB age predicting models for all samples (0-90 year old) and 15-30, 30-45, 45-60 and 60-90 age groups.
Figure 8A:
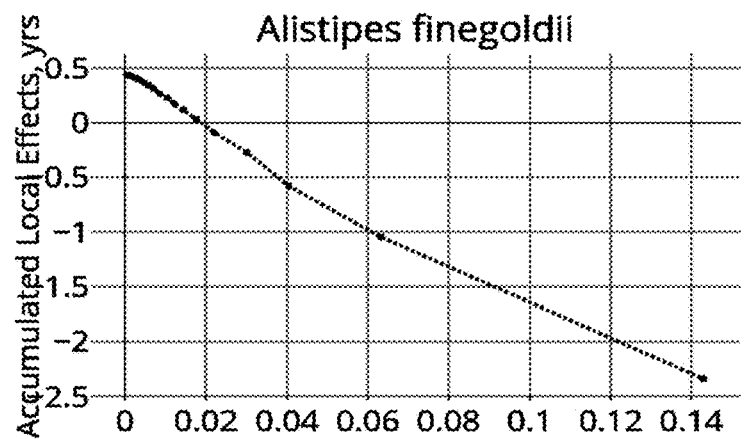
FIGS. 8A-8X show ALE plots for 24 features in DFS model.
Figure 8B:
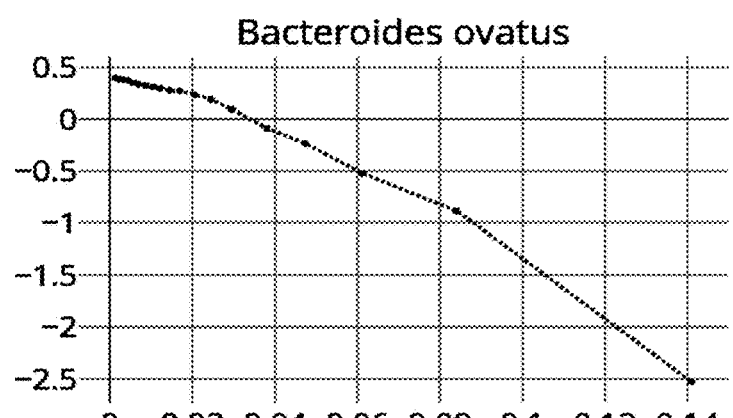
FIG. 8Y shows the calculated ALE values for FIGS. 8A-8X.
Figure 8C:
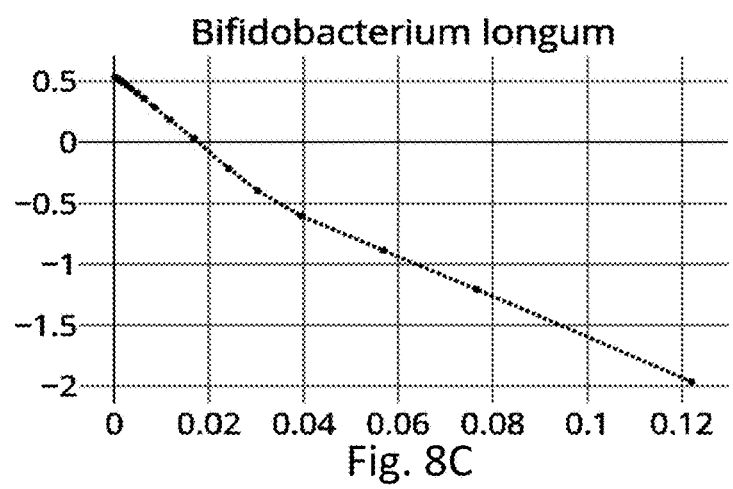
Figure 8D:
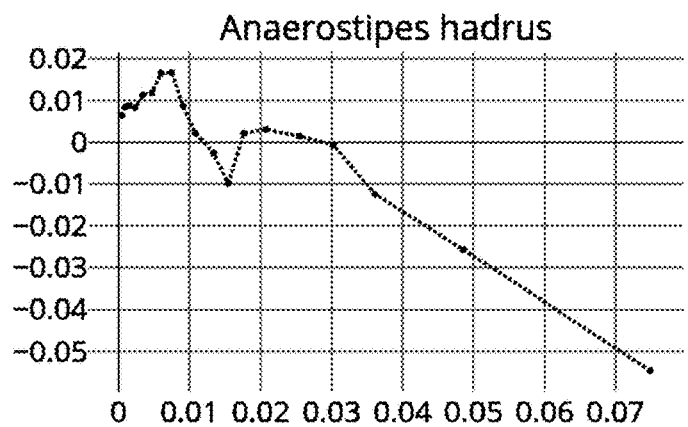
Figure 8E:
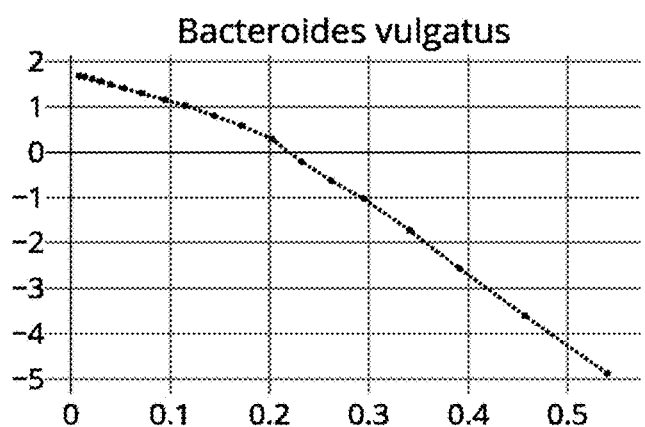
Figure 8F:
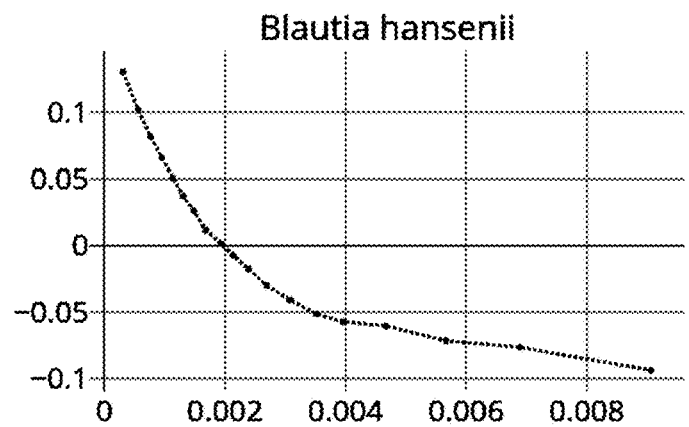
Figure 8G:
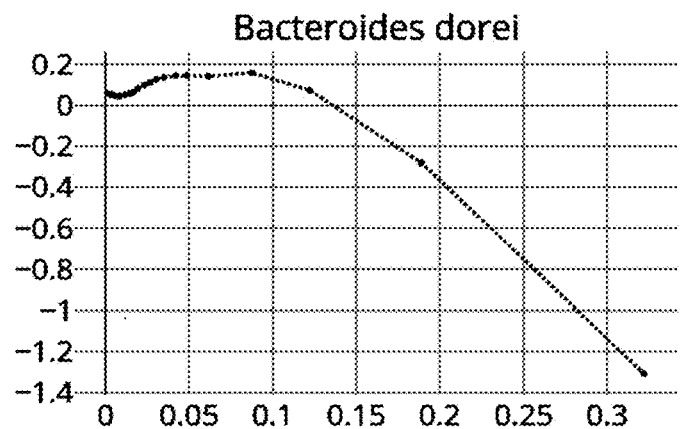
Figure 8H:
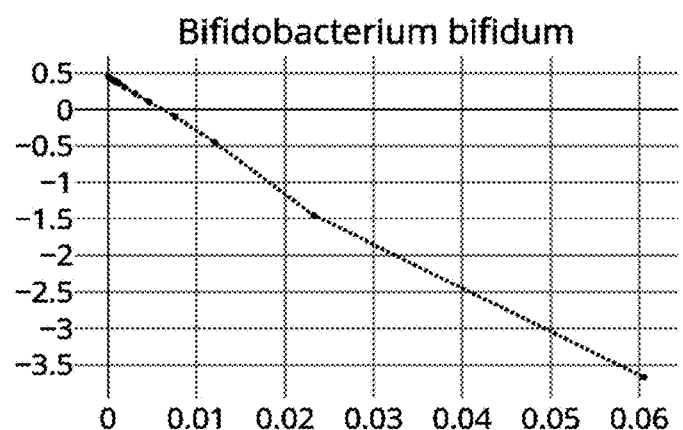
Figure 8I:
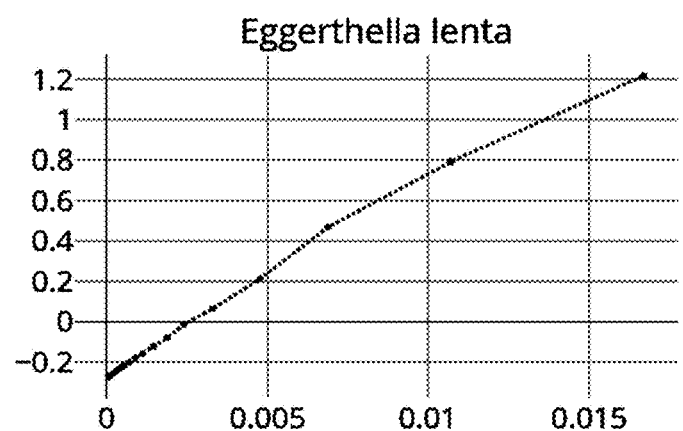
Figure 8J:
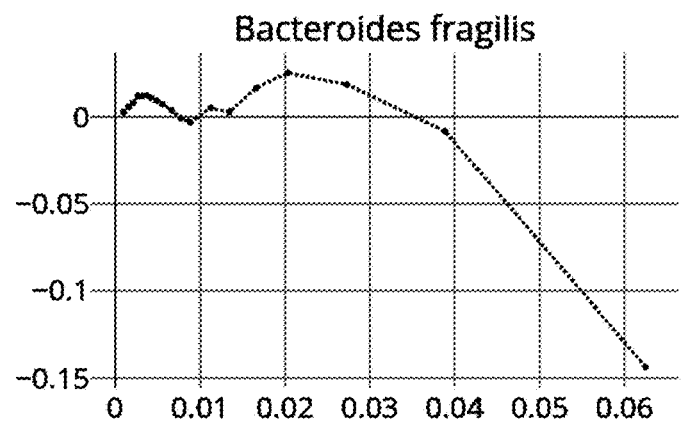
Figure 8K:
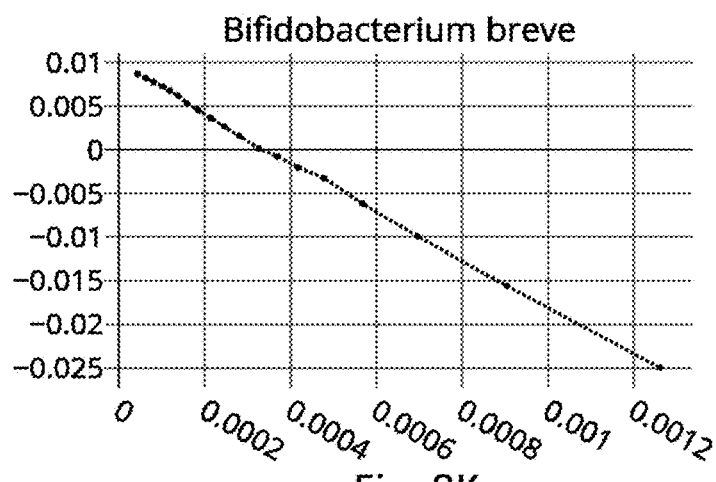
Figure 8L:
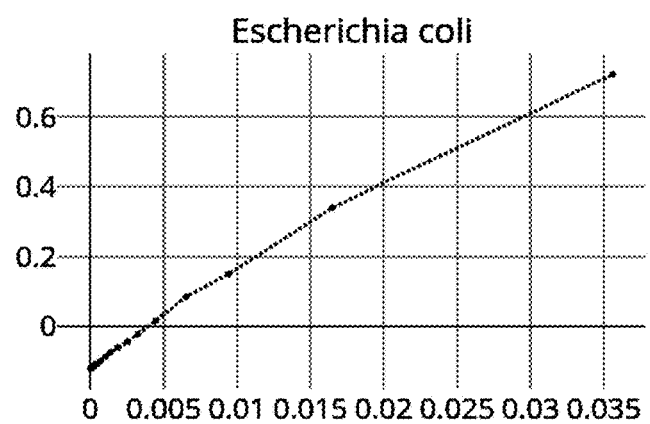
Figure 8M:
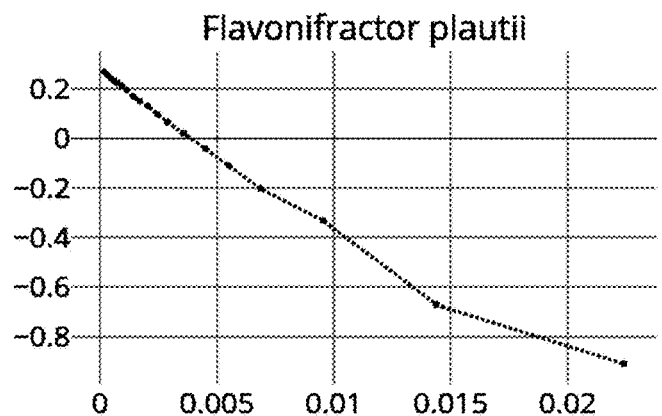
Figure 8N:
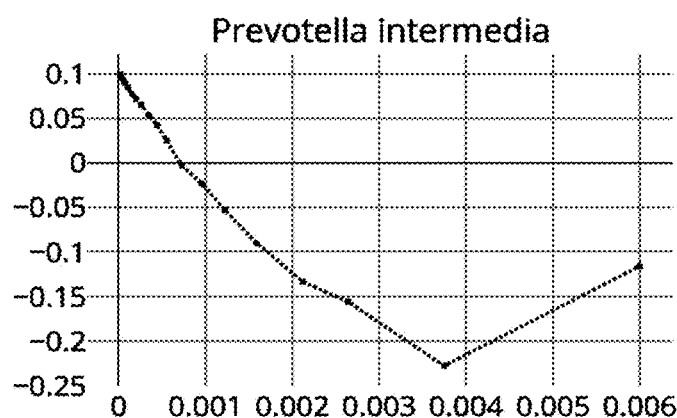
Figure 8O:
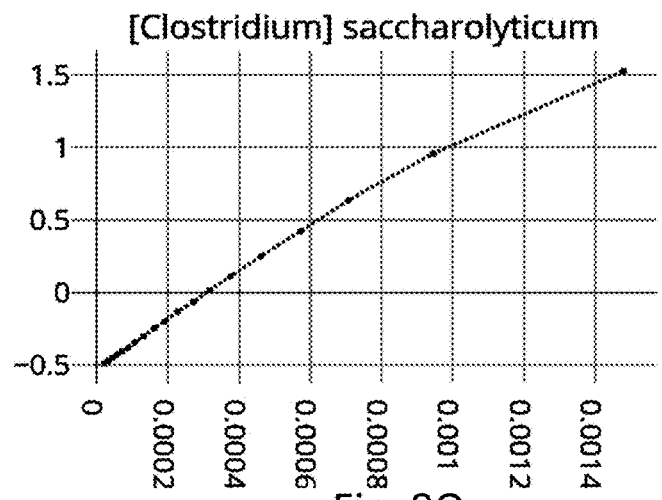
Figure 8P:
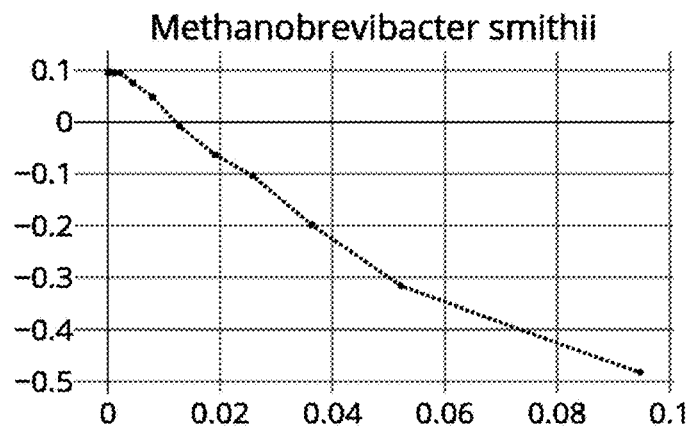
Figure 8Q:
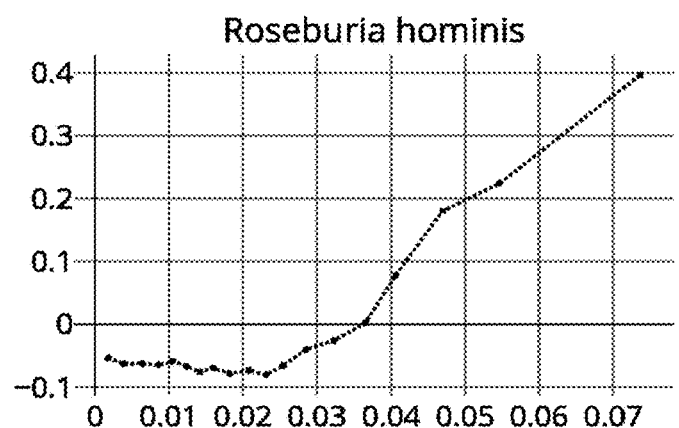
Figure 8R:
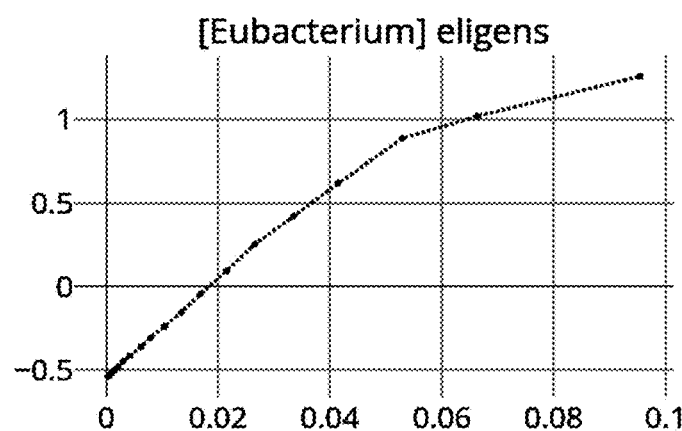
Figure 8S:
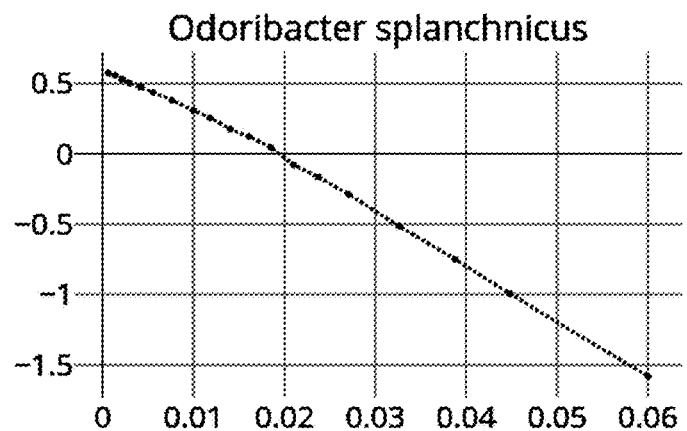
Figure 8T:
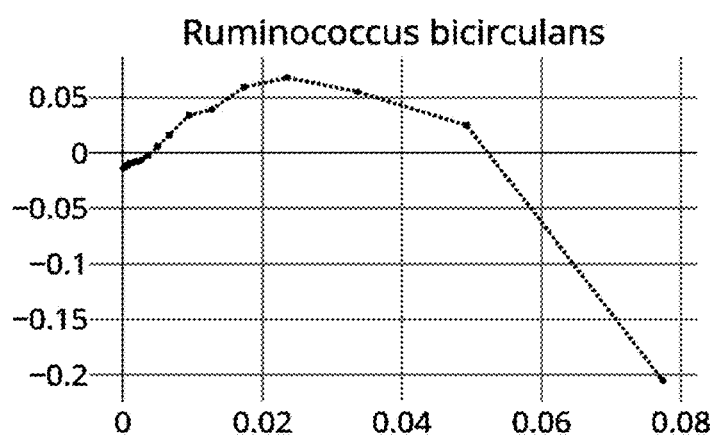
Figure 8U:
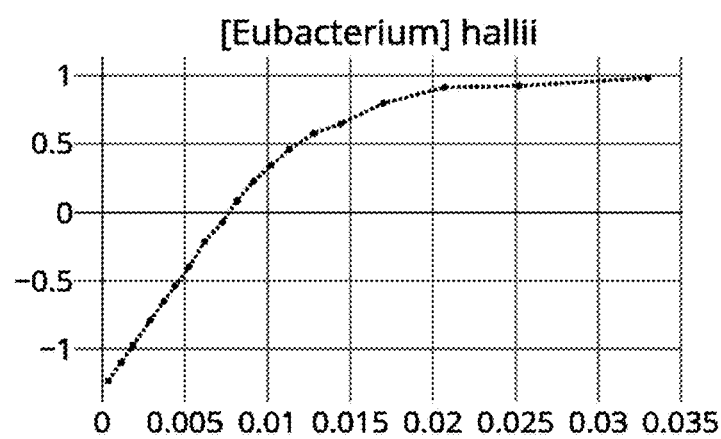
Figure 8V:
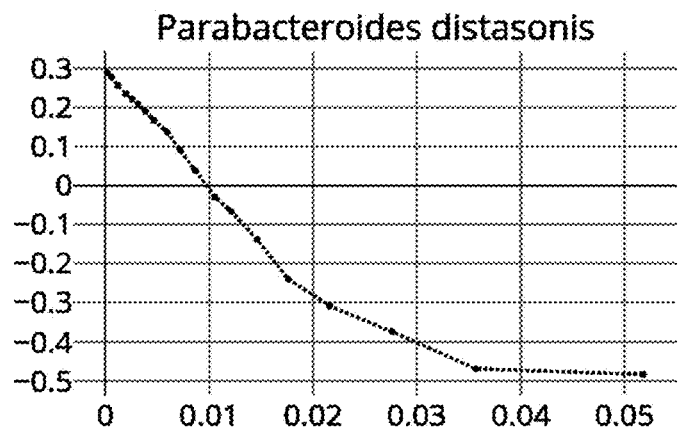
Figure 8W:
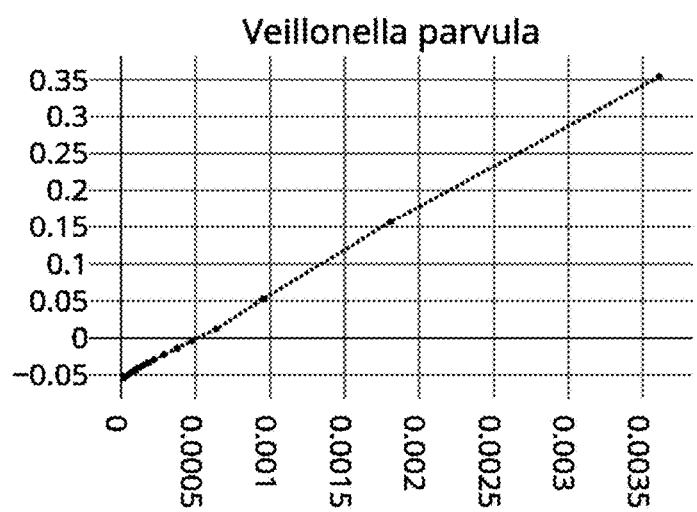
Figures 9A, 9B:
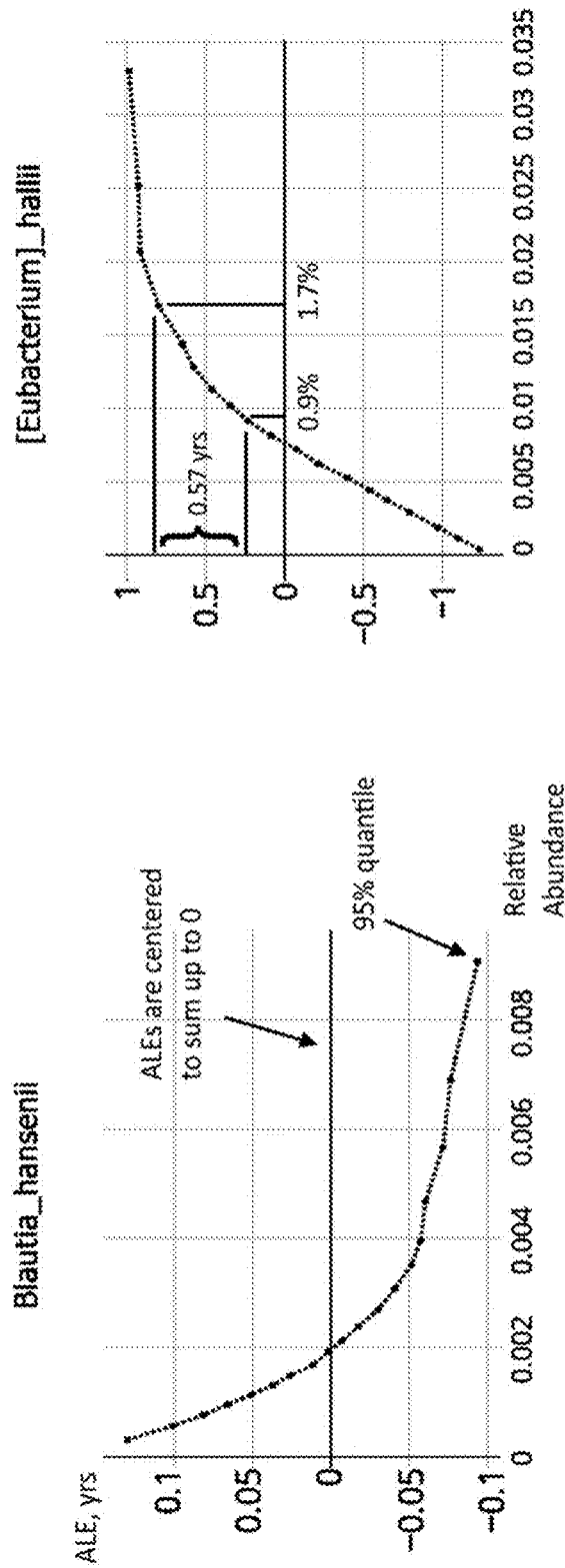
FIGS. 9A and 9B provide some instructions for using ALE plots.

In some embodiments, two or more of the microorganisms are used. In some aspects, only the even numbered microorganisms are used. In some aspects, only the odd numbered microorganisms are used. In some aspects, five or more of the microorganisms are used. In some aspects, only the microorganisms of FIG. 4 are used. In some aspects, only the microorganisms of FIGS. 8A-8Y are used. In some aspects, only the microorganisms of FIGS. 9A-9B are used.

Using ALE plots, such as in the figures herein, allows to estimate the impact a specific microbe elicits on the age predicted within the model. Microbes whose effect is monotonically rising with abundance will be termed here as "progeroid" and whose effect is monotonically decreasing as "geroprotective" (see FIG. 8A-8Y). Additional information is provided herein. In some instances, the ALE is carried out on profiles that are derived from real profiles, where the derived profiles are somewhat altered.

Within this definition such species as follows are geroprotective: *Acidaminococcus intestine; Bacteroides caccae; Bacteroides caecimuris; Bifidobacterium catenulatum; Bifidobacterium pseudocatenulatum; Chryseobacterium gallinarum; Desulfovibrio fairfieldensis; Dialister pneumosintes; Lachnoclostridium sp. YL32; Lactobacillus amylovorus; Megasphaera elsdenii; Ornithobacterium rhinotracheale; Oxalobacter formigenes; Prevotella jejuni; Rhodococcus sp. YL-1; Alistipes finegoldii; Anaerostipes hadrus; Bacteroides dorei; Bacteroides ovatus; Bacteroides vulgatus; Bifidobacterium bifidum; Bifidobacterium breve; Bifidobacterium longum; Blautia hansenii; Flavonifractor plautii; Methanobrevibacter smithii; Odoribacter splanchnicus; Parabacteroides distasonis; Prevotella intermedia*; and others. In some aspects, the microorganisms of this paragraph are a specific group, and are used as a specific combination, herein "Geroprotective Group," which designates that the specific members in the group are geroprotective. Accordingly, each of the different types of recited microorganisms in this paragraph is present in the Geroprotective Group.

Within this definition such species as follows are progeroid: *Acidaminococcus fermentans; Bifidobacterium dentium; Enterococcus faecalis; Faecalibacterium prausnitzii; Hafnia sp. CBA7124; Lactococcus lactis; Parvimonas micra; Pseudomonas aeruginosa; Eggerthella lenta; Escherichia coli; Roseburia hominis; Ruminococcus bicirculans; Veillonella parvula*; and others. In some aspects, the microorganisms of this paragraph are a specific group, and are used as a specific combination, herein "Progeroid Group," which designates that the specific members in the group are monotonically rising with abundance. Accordingly, each of the different types of recited microorganisms in this paragraph is present in the Progeroid Group.

The methods described herein use biological information, such as information regarding one of the Groups of microbes. As such, the method includes obtaining the biological information. The steps of obtaining the biological information can include the physical acts of obtaining biological samples and processing the samples, such as described herein or generally known, to obtain the biological information. As such, examples of ways to acquire the biological information can include: analyzing the plurality of microorganism nucleic acids to determine the amount of microorganisms in a host habitat; analyzing the plurality of an organism's nucleic acids to determine the amount and location of genomic mutations; analyzing the plurality of an organism's nucleic acids to determine the intensity of gene transcription; analyzing the plurality of chemical compounds within an organism's tissue to determine their concentration; analyzing the plurality of cell types within an organism's tissue to determine their amount. This can be done by obtaining the information from biological samples. Alternatively, data of the biological information can be provided. Then, the analyzing actions can be performed.

In some embodiments, the derived biomarkers are used to approximate the initial aging clock performance with reduced number of features. In some aspects, the reduced number of features is used to assess the health status of an organism. In some aspects, the reduced feature vectors are stored in a database with regulated access. In some aspects, machine learning models built on reduced feature vectors are accessible to the professionals or public to provide general life style advice. In some aspects, machine learning models built on reduced feature vectors are included into an ensemble with other machine learning models to increase their performance in age or health status prediction.

In some embodiments, seno-positive features are treated separately from seno-negative features to provide two scores associated with an organism's age or health status. Some embodiments may include only seno-positive features, while others may include only seno-negative features. In some aspects, the seno-status of one or more specific features is determined on the same samples used in model training, in others, it is determined on outside samples. In some aspects, features with the determined seno-status are used to design geroprotective consumer products, diet plans, interventions, therapies or other services.

In some embodiments, the process of possessing the taxonomic profile can include inputting and processing various profiles of one or more of the microorganisms with a computing system. For example, the processing can include processing the absolute amount or percentage (e.g., absolute abundance), genus level profiles for the microorganisms (e.g., amount or percentage for each microorganism in a defined genus), taxon specific gene counts for the microorganisms (e.g., amount or percentage for each microorganism in a defined taxon), ecological group amounts or percentages (e.g., abundance) or other profile information. The data can be manipulated in any way, such as by factors, to obtain processed data, and such processed data can be used in the analysis and predictions. For example, the relative or absolute amounts can be multiplied by a factor, and the result used in the methods.

In some embodiments, the method can include processing the biological sample to provide a taxonomic profile with strain, species or genus resolution. This can allow the profile to be specific to different strains, specific at the species level (e.g., including all of the organisms in a species) or specific at the genus level (e.g., including all of the microorganisms in a genus). As such, the data can be processed in a manner to select a certain taxa for use in making the age prediction, and/or parsing the different taxa from each other so that individual profiles can be generated for each individual taxon.

In some embodiments, each taxonomic profile is based on 16S variable region data. In some embodiments, each taxonomic profile is based on whole metagenome data.

In some embodiments, the taxonomic profile can be considered a metagenomics profile. The metagenomics profile of a subject can then be compared to a reference metagenomics profile or a plurality of reference metagenomics profiles. A reference metagenomics profile can be from one subject or combined from a plurality of subjects. The comparison can then be used to further determine the subject's biological age. In some instances, the comparison can be performed in order to find similar microbial compositions that produce different age predictions, as well as various microflora alterations that can modulate or change the predicted age. Such information can be included in a report, for example to report a suggested alteration to the subject's microflora taxonomic profile.

In some embodiments, the method can include obtaining personal information regarding the subject, and including the personal information in the processing in order to determine the subject's biological age. The personal information can include personal medical history, family medical history, length of life for family members, types of diseases or disorders the subject has had or still has, types of diseases or disorders for family members, medical images for the subject and/or family members, medical diagnostic data for subject and/or family members, current weight and/or weight history for subject and/or family members, current body mass index for subject and/or family members, biometrics of subject and/or family members, geographical location of current residence and/or residence history for subject and/or family members, drinking or smoking habits, eating habits, exercise habits, or other personal data related to health or lifestyle. The family member can be people that are within 1, 2, 3, 4, or 5 degrees of consanguinity. The personal data can then be compared with the metagenomics profile of the subject or of reference metagenomics profiles during the determination of biological age. This information can be used to explore correlations between a predicted biological age and the data of the taxonomic profiles in view of the personal data. When done across multiple profiles, the correlations of personal data with the predicted age and the data of the taxonomic profiles can be used to enhance the predictions as well as determine unhealthy personal data that can contribute to higher phenotypic ages, or use the healthy personal data to design strategies (e.g., treatment, diet, exercise, lifestyle, etc.) to reduce the biological age in others.

In some embodiments, the protocols can include particular analytics of the microbial taxa for obtaining the taxonomic profiles that show the relative amount or abundance or absolute amount or abundance of a specific taxon metagenomics profile. As such, the relative analysis can be one specific taxon relative to the other taxa in the profile of a subject or relative to the same taxa in another subject or a population of subjects, such as the average or mean relative amount. The absolute amount or abundance can be characterized as the number of microorganisms of each taxon being considered in the metagenomic profile.

In some embodiments, the protocols for obtaining the taxonomic profile while estimating/determining the amount or percentage of each taxon of the taxa can include generating a corresponding functional profile of the subject's microbiota. In some aspects, the protocol can use taxonomic profiles, which may include a feature that is a bacterial species. The protocols can also use the same data to produce functional profiles, wherein a feature is a gene family that may contribute to: (1) lower phenotypic age than real age; (2) same phenotypic age as real age; and/or (3) higher phenotypic age than real age. The methods can use functional profiles, modified to accept gene amounts, abundances, or percentages. The phenotypic age is the calculated biological age of the biological clock model.

In some embodiments, the protocols described herein can include using the resulting prediction of age as a measure of phenotypical age. As such, the phenotypical age can be compared to the subject's real age. When there is a difference, such as the phenotypical age being older than the real age, then interventional protocols can be implemented in an attempt to reduce the phenotypical age to the actual age. This may include certain treatments, such as antiaging treatments. The treatments of the incorporated references may also be used. When the difference is the phenotypical age being younger than the chronological age, the subject can be analyzed for their genetics profile, proteomics profile, health profile, family heath profile, eating habits, exercise habits, sleep habits, work habits, and other features of the subject's life can be studied in order to identify parameters that may result in the younger phenotypic age (e.g., more desirable) or an older phenotypic age (e.g., less desirable). Such parameters can then be aggregated and provided to subjects that have older phenotypic ages than their real age so that they may try to implement the parameters in order to reduce an older phenotypic age so that their phenotypic age trends toward their real age. As such, a healthy person with a younger phenotypic profile can be used as a model of health and behavior patterns so that their health and behavior patterns can be implemented in other subjects in an attempt to reduce the phenotypic ages to be closer or younger than the real age.

In some embodiments, the protocols can be performed with a number of subjects such that a plurality of taxonomic profiles can be obtained and compared to each other. This also allows for the plurality of taxonomic profiles to be used to identify one or more taxon that are present in subjects that have: (1) lower phenotypic age than real age; (2) same phenotypic age as real age; and/or (3) higher phenotypic age than real age. The taxa that are involved in either category can be identified across a population of subjects, and then used as standards for determining the predicted phenotypic age. As such, the identification of at least one microbe or group of microbes whose change in amount or percentage or other value (e.g., abundance) that can affect a subject's predicted age can be made. The identity of the one or more microbes can be used to identify the microbes that can be useful for obtaining a lower phenotypic age, and such microbes may be included in a treatment to provide such microbes to a subject having the same or higher phenotypic age than their real age. As such, the beneficial microbes attributed to a lower phenotypic age can be used in therapies. On the other hand, microbes that are identified to contribute to an older phenotypic age can be used to assess the phenotypic age of other subjects as well as being identified by removal. That is, strategies may be used to remove these types of microbes from the subject's microbiota. In an example, a mass removal of microbes can be performed, and then beneficial microbes linked to younger phenotypical ages can be established in the subject's microflora. Also, a beneficial taxa profile can be used to create a beneficial grouping of live microbes to be established in the subjects' microbiota. The information regarding the taxonomic profile and microbes thereof can be reported to the subject as well as a plan for treatment if the phenotypic age is higher than the real age.

In some embodiments, a plurality of taxonomic profiles can be compiled in a database, which may be aggregated or parsed into databases that have profiles for: (1) lower phenotypic age than real age; (2) same phenotypic age as real age; and/or (3) higher phenotypic age than real age. The taxonomic profiles may also be parsed into categories for various diseases or disorders, such as those that are age related (e.g., phenotypic age related diseases or disorders). Accordingly, the protocol for a specific subject may then include comparing the subject's taxonomic profile with the profiles of the database. This can be used for comparing a specific subject's profile to a reference database, and then assessing the subject's comparative phenotypic age and/or risk of developing age associated disorders. The risk can be calculated as the probability of having a certain taxon profile or taxa profile correlated with the associated disease or disorder. The information regarding the comparative phenotypic age and/or risk of developing age associated disorders can be compiled into a report and this information can be reported to the subject.

In some embodiments, the protocol can include creating a database of reference profiles and their corresponding predictions for chronological age, phenotypical age, or disease or disorder states associated with the difference between the true chronological age and the determined phenotypic age. The database may also include the state of health of each subject along with their various dietary, exercise, lifestyle, or other behavioral information (e.g., personal data).

In some embodiments, the protocol can include creating software that can be used for comparing a subject's microbiological taxonomic profile to the reference database. This can include creating software that receive a subject's microbiological taxonomic profiles and comparing it to one or more other subject's microbiological taxonomic profiles. The profiles that are comparable and similar can be used to ascertain the age of the reference(s) or average thereof, and using such age or average ages to predict the phenotypic age of the subject. The software can also be used for providing information on specific microbes' influence on the individual's age prediction. This information can be compiled into a report, and reported to the subject.

In some instances, the database, such as the database having the microbiological taxonomic profiles with or without being associated with a phenotypic age can be configured as a blockchain storage system. The blockchain storage system can be used to track the microbiological taxonomic profile progression (e.g., change over time) of one or more subjects. The blockchain storage system can be used to track the predicted phenotypic age in view of the microbiological taxonomic profile progression.

In some instances, the protocols can include training the age predicting clock (e.g., model, machine learning platform) only on chronological age with or without being associated with a taxonomic profile. Additionally, with more personal data the protocol can transfer the method to make a phenotypic aging clock. Phenotypic age can be provided as a measure to inform subjects on the risks of aging associated disorders. In some instances, the protocol is not assessing chronological age, but only a phenotypic age, or vice versa.

In some embodiments, the databases and reports can include information about at least one specific microbe that can modulate an age prediction. The microbe may increase the age prediction or reduce the age prediction. Such one or more microbes can be identified for use in analyzing the taxonomic profiles to determine a predicted age. The presence, absence, or amount of such one or more microbes can be beneficial in correlating a subject's taxonomic profile with a phenotypic age estimation or prediction.

In some embodiments, the protocols can include identifying dietary plans for subjects that can result in lower or equal phenotypic ages compared to the real age. In some aspects, the dietary plan to reduce a phenotypic age can be one that is from another subject that has a lower phenotypic age than the current subject. The dietary plan of a subject with a lower phenotypic age can be applied to a subject with a higher phenotypic age in an attempt to reduce the phenotypic age of the subject. In some instances, dietary plans of a plurality of subjects with lower phenotypic age can be compiled and analyzed to identify features that are consistent across a high percentage of subjects with lower phenotypic ages, and then the features of such lowering phenotypic dietary plans can be identified. The identified features of the lowering phenotypic dietary plans can then be applied to subjects with higher phenotypic ages. Thus, successful dietary plans can be used for treatments in other subjects in need thereof.

In some aspects, the protocol can include creating a dietary plan designed to support or suppress specific microbes whose change in amount, percentage, or abundance can affect the predicted age, such as lower the phenotypic age. The created dietary plan can then be included in a report that is delivered to a subject in need of reducing their phenotypic age. Also, the created dietary plan can be implemented as a treatment dietary plan in a subject in need of reducing their phenotypic age.

In some embodiments, a method can include generating a recommended therapy for a subject based on their taxonomic profile. This can include determining the metagenomics profile and/or age prediction (e.g., phenotypical age), which can then be used for determining a recommended therapy. The recommended therapy can include traditional medicinal therapies, such as by administering therapeutic agents (e.g., drugs, vaccines, etc.) as well as a therapy to change the microbiome of a subject into a healthy microbiome that has been determined to be associated with younger phenotypic ages. The change of microbiome can include cleansing a microbiome so as to remove certain microbes or all microbes, and replenishing the microbiota with selected microbes or taxonomical microbe profiles that are associated with younger phenotypic ages. The protocol can include comparing a subject's metagenomic profile and age prediction with a reference metagenomics profile, determining a therapy, generating a report on the determined therapy, and reporting the report of the therapy to the subject.

In some embodiments, the protocol can include analyzing information on at least one specific microbe's influence on age prediction. Then, the protocol can include creating microflora therapies, such as causing the microflora of a subject to trend towards being similar to a healthy microflora of a person with a younger phenotype. The microflora therapies can be implemented in order to change the age predictions over time. As such, the identified microbe can be used for developing such microflora therapies, and providing the microflora therapies to a subject as well as to a plurality of subjects in the population. A deep feature synthesis (DFS) model or xgboost (XGB) model can be used to define beneficial microbes (e.g., resulting in younger phenotypic age) and/or harmful microbes (e.g., resulting in older phenotypic age). These beneficial microbes can be included in therapies or treatments applied to the subject in order to increase the amount, abundance or percentage of such beneficial microbes. The harmful microbes can be then be targeted for selective removal, or possibly for general microbe removal when the harmful microbes are found. Then, beneficial microbes can be used to restore the microbiota to a beneficial state.

In some embodiments, consumer goods can be designed based on the taxonomic profiles as well as the correlated predicted phenotypic age. The protocols allow for the models to estimate the influence certain microbes elicit on an ageing process. Some dietary products could be designed specifically to alter gut microflora compositions in a desirable way, such as to increase the predicted phenotypic age. The consumer goods can be personalized or designed based on general patterns of microbiome age progression in the population for younger predicted phenotypic age. The microbes identified to be correlated with older predicted phenotypic age may be specifically excluded from consumer goods. While this technology is described with a focus on human gut microbiome, the same methods disclosed here may be applied to other human habitats or other types of animals to obtain similar results. These taxonomic profiles and predicted phenotypic age can be used in designing a plethora of consumer goods that are designed to modify corresponding microbiota, where some examples of consumer goods can include clothes, body odor blockers, underwear, toothpaste and oral care products as well as many others. Additionally, consumer goods for non-humans may also be designed based on age prediction and marker set derivation. For example, the methods may also be applied to modify cattle feed additives.

The identified beneficial microbes and identified harmful microbes can be useful for developing consumer goods or articles of manufacture or any substance or anything that can be a good provided to a consumer. These can be used for increasing the beneficial microbes in a microbiota of a subject. These can also be used for reducing the harmful microbes in a microbiota of a subject. These can also be used for creating a beneficial microbe taxonomic profile in the microbiota of a subject. In part, designing consumer goods can be based on generalizing the taxonomic profile information in a reference database. The goods can then be delivered to the consumer for: for increasing the beneficial microbes in a microbiota of a subject; reducing the harmful microbes in a microbiota of a subject; or creating a beneficial microbe taxonomic profile in the microbiota of a subject. Some examples of the goods can be cosmetics, dietary products, medical products, clothes, instruments, comestibles, or the like. The goods can include the beneficial microbe(s), substances to promote wellness, substances that beneficial microbes depend on (e.g., Vitamins A, B, C, D, etc.) or the like.

In some embodiments, the information regarding identified beneficial microbes and identified harmful microbes as well as beneficial microbe taxonomic profiles can be used in creating a cosmetics product designed to support or suppress specific microbes whose change in amount, percentage, abundance, or other parameter would affect the age prediction (e.g., make the age prediction younger). The cosmetic product can be delivered to the subject and used by the subject. The cosmetics can include makeup, mascara, foundation, lip gloss, eyeshadow, eyeliner, lip balm, primer, blush, lipstick, nail polish, concealer, powder, bronzer, highlighter, lip stain, lip liner, shampoo, conditioner, hair styling composition, hair color, shine serum, pomade, moisturizer, cleanser, antiaging cream, exfoliators, eye drops, blemish control composition, acne control composition, makeup remover, toners, astringents, oral care compositions, night cream, tanners, sun blocks, toothpaste, lip plumper, body lotion, fragrance, body wash, antiperspirant, deodorant, soap, hair removal composition, sun care composition, body scrub, bath salts, bath fizzes, aromatherapy, cellulite treatments, scar reducers, body powders, or others.

In some embodiments, the information regarding identified beneficial microbes and identified harmful microbes as well as beneficial microbe taxonomic profiles can be used in creating a dietary product designed to support or suppress specific microbes whose change in abundance would affect the age prediction (e.g., make the age prediction younger). The dietary product can be delivered to the subject and used by the subject. The dietary product can be anything that is comestible, such as food, drink, supplement, powder, pill, capsule, or anything else.

In some embodiments, the information regarding identified beneficial microbes and identified harmful microbes as well as beneficial microbe taxonomic profiles can be used in creating a medical product designed to support or suppress specific microbes whose change in abundance would affect the age prediction (e.g., make the age prediction younger). The medical product can be delivered to the subject and used by the subject. The medical product can include those used on an inside of a subject (e.g., catheter, stent, filter, needle, implant, etc.) or those used on an outside of a subject (e.g., bandage, brace, cast, etc.).

In some embodiments, the information regarding identified beneficial microbes and identified harmful microbes as well as beneficial microbe taxonomic profiles can be used in creating clothes designed to support or suppress specific microbes whose change in abundance would affect the age prediction (e.g., make the age prediction younger). The clothes can be delivered to the subject and used by the subject. The clothes can be any item worn by a subject, such as underwear, bra, pants, shorts, shirts, hats, gloves, socks, or the like.

In some embodiments, method of insurance rate determination can take the predicted phenotypic age as well as the taxonomic profiles into consideration. The methods in the insurance industry can allow the insurance companies to estimate rates that are more accurately representative of the predicted phenotypic age. A prediction that places a client in a higher age bracket (e.g., higher predicted age) than he actually is in (e.g., lower real age) provides a signal that they may have hidden conditions that could affect the expected life span or disease risk, and thus the intended insurance rate. For example, gut microflora associations with certain health issues and treating the age prediction as a general marker of human phenotypical age, an insurance agent can assess the likelihood of the payout events in the future. For example, if a healthy 30 year old male wants to purchase a life insurance, but his microflora is more typical for a 60 year old person, the agent may look up the risk of developing a heart condition in a reference data base for older individuals and factor in that risk by increasing the annual rate by the weight of this age prediction among other criteria. On the other hand, if a 60 year old person provides a profile that is predicted to be much younger, the client may receive a discount.

In some embodiments, in order to receive insurance policy discounts, policy holders may be willing or required to provide their microbiological taxonomic profiles themselves as well as the predicted phenotypic age as determined by the present invention.

In some embodiments, to keep track of a subject's phenotypic age or their taxonomic profiles, a blockchain solution can be implemented. Immutable and tamper-proof blockchain data bases would allow insurance-agents to request data easily and let the clients control who has access to their personal data.

In some embodiments, the predicted phenotypic age can be used in determining insurance policies for a subject. As such, insurance methods can be configured to consider the predicted phenotypic age in order to increase a policy cost when the predicted phenotypic age is higher than a threshold or actual age. Also, insurance methods can be configured to consider the predicted phenotypic age in order to decrease a policy cost when the predicted phenotypic age is lower than a threshold or actual age. Accordingly, the insurance methods can include developing insurance policies based on analyzing the metagenomics microbiological taxonomic profile of the subject in view of the metagenomics microbiological taxonomic profiles in the reference database. The insurance policy based at least on part on the metagenomics microbiological taxonomic profile can be delivered to insurance customers. In some instances, a policy holder's payment rate is influenced by age prediction derived from their microbiological taxonomic profile as described herein. In some instances, a policy holder is required to provide verified dynamics of their microbiological taxonomic profile and corresponding age predictions to the insurance provider for analysis.

In some embodiments, a method can be performed for creating predictive computer models that can analyze the microbiological taxonomic profile of one or more subjects and then provide the predicted phenotypic age. The protocol can include analyzing aggregated data (e.g., microbiological taxonomic profile and/or predicted phenotypic age) to produce generative models for creating in silico microbiome communities. The in silico microbiome communities can be configured to be difficult to distinguish from real reference databases. As such, the in silico microbiome communities can be used in place of real reference databases. This can allow for the age predicting methods to use simulated data, such as the in silico microbiome communities, instead of real data of real subjects.

In some embodiments, a method of generating a synthetic taxonomic profile can include: providing a microbiomic aging clock that has been trained with abundance profiles of the abundance of microbes of the microbiota of a plurality of subjects based on the nucleic acid information for each subject; generating at least one synthetic taxonomic profile; and generating a report for the at least one synthetic taxonomic profile. In some aspects, the method can include: inputting criteria into the microbiomic aging clock for a synthetic subject having a defined phenotype; and generating the synthetic taxonomic profile for the synthetic subject based on the defined phenotype. For example, the generative model can be used to create a synthetic (e.g., in silico) microbiome community or taxonomic profile for a synthetic microbiota. That is, once the microbiomic aging clock is obtained, it can be used to generate a synthetic microbiomic community or synthetic taxonomic profile for a synthetic subject that is not a real subject. This provides predictive information for a non-real subject. In an example, the microbiomic aging clock can be input with parameters to obtain the synthetic microbiomic community or synthetic taxonomic profile for the input parameters, where the input parameters can include information such as health status, weight, sex, age, any disease, any injuries, or other similar information. In an example, the input can include information for a 21 year old man with diabetes, and the microbiomic aging clock can provide a prediction or one or more examples of a synthetic microbiomic community or synthetic taxonomic profile for the 21 year old man with diabetes. Thus, based on input information for a non-real subject, the synthetic microbiomic community or synthetic taxonomic profile can be generated.

In some embodiments, the protocols, such as using the predictive computer models, can result in a predicted phenotypic age. Such predicted age can be provided as a value. Also, such predicted age can achieve a mean absolute error of a number of years, months, and/or days when predicting a subject's age based on their microflora taxonomic profile. Such predictions of phenotypic age may be used for forensic methods, medical methods, and scientific purposes.

To prevent personal information leaks, subjects can digitally sign their samples using an asymmetric algorithm with their personal signing key. This allows the key holder to prove the authenticity of their microbiological profile and the corresponding age prediction without mentioning their digital identities in the storage. Moreover, expert facilities may also sign profile and prediction hashes to verify that data acquisition and analysis has been carried out by them.

To decentralize data analysis and prevent data association and accumulation by expert facilities, WGS machines could be attached to decentralized computation systems. As an illustration: a sequenator performs sequencing without possessing any information about the subject, however it receives a subject's digital signatures and keeps signature-sequencing associations in memory. It feeds the output and the signature to a decentralized computing system, where data goes through quality control, binning and prediction algorithms shared by all its agents. Such systems that allow for secure remote computation via enclaves guarantee that the agents do not have access to the data they analyze. A subject may need to share their public keys and a signed path to the decentralized storage location with the computation system beforehand in order to be the only person that can be granted access to the output. The computation system checks the signature of its input and redirects the output to an assigned location. This way the metagenomic profile and prediction are available only to the subject: the expert facility carries out the sequencing, but does not receive any output, while the computation network agents have no access to sequencing data by design and the final output is stored in the subject's location of choice. To verify the legitimacy of all processing steps, each participant in this pipeline leaves its signature on the output hash.

In some embodiments, after the subject receives the data they may share it with an entity (e.g., with the insurance policy provider) that will be able to check the authenticity of the prediction by checking signatures accumulated during processing.

The present models can be obtained by machine learning.

The present invention can adapt several machine learning approaches for age prediction. The objective of a machine learning problem is a classical supervised regression. Models can be trained on bacterial taxon features as input variables.

Data for training machine learning algorithms can be modified to contain only reliably detected features (>1e-5 abundance). For example, the size of the data after removing non-existent or missing age values can be about 3,058 records from about 621 people. Each record can contain 1,673 bacteria features. The target variable can include ages in a range of 7 and 90 years old. For example, the age distribution can be depicted in FIGS. 10A-10B.

The models can be evaluated by various protocols.

Models can be trained with five-fold cross validation and grid/random search strategies to compensate for overfitting. Due to the considerably moderate size of the dataset, no outer test set is introduced. Instead, given metrics can be obtained as prediction of 5 test sets corresponding to each fold, thus resulting in the fully predicted input dataset. All models can be evaluated with the same fold-splitting for the fair comparison. The following metrics can be measured for all evaluations.

The coefficient of determination ($R^2$) is defined as:

$$R^2 = 1 - \frac{SS_{residual}}{SS_{total}}$$

$$SS_{total} = \sum_{i=1}^{N} (Age(C_i)_{obs} - \overline{Age})^2$$

$$SS_{residual} = \sum_{i=1}^{N} (Age(C_i)_{obs} - Age(C_i)_{pred})^2;$$

where $\overline{Age}$ is average age in the data set and C is a taxonomic profile from sample i.

The mean absolute value (MAE) can be defined as:

$$MAE = \frac{1}{N}\sum_{i=1}^{N} |Age(C_i)_{pred} - Age(C_i)_{obs}|;$$

where $C_i$ is a taxonomic profile from sample i.

The Pearson's correlation coefficient (r) can be defined as:

$$r = \frac{\sum_{i=1}^{N}(Age(C_i)_{obs} - \overline{Age_{obs}})(Age(C_i)_{pred} - \overline{Age_{pred}})}{\sqrt{\sum_{i=1}^{N}(Age(C_i)_{obs} - \overline{Age_{obs}})^2}\sqrt{\sum_{i=1}^{N}(Age(C_i)_{pred} - \overline{Age_{pred}})^2}};$$

where N is the number of samples, and $\overline{Age}$ is an average predicted or observed age.

The $R^2$ metric can be chosen as a target metric for performance comparison. The performance of different models and their configurations can be compared based on target metric on the whole predicted dataset.

In some embodiments, the model can be configured as a neural network configuration, which can be a deep feature selection (DFS) model. Between different choices of neural nets models, DFS can be used for the methods described herein for at least two reasons. First, the DFS model is aimed to identify the most important features, which can be necessary for feature interpretation. Secondly, the DFS model implies a deep architecture, which shows the best results for a task of prediction from high-dimensional data. The main idea of the DFS model is to add a sparse one-to-one linear layer between the input layer and the first hidden layer of the MLP. The objective of DFS model is defined as:

$$\min_{\theta} f(\theta) = l(\theta) + \lambda_1\left(\frac{1-\lambda_2}{2}\|w\|_2^2 + \lambda_2\|w_1\|\right) + \alpha_1\left(\frac{1-\alpha_2}{2}\sum_{k=1}^{K+1}\|W^{(k)}\|_F^2 + \alpha_2\sum_{k=1}^{K+1}\|W^k\|_1\right)$$

The architecture of the final model can be obtained by adjusting the following hyperparameters: number of layers with number of neurons within each layer, types of nonlinearity (ReLU, PReLU, ELU, LeakyReLU), learning rates (0,001, 0.005, 0.001). Adam can be used as an optimizer. A dropout technique with probability rate of 0.5 can be used to reduce overfitting. For the architectures with 2 and 3 hidden layers, Batch Normalization technique can be employed.

In some embodiments, a feature analysis can be performed. To identify bacterial taxa (e.g., more than one taxon) that are important for age prediction, the present protocols can employ the following techniques: permutation feature importance (PFI) and accumulated local effects (ALE).

In some instances, the PFI method can be used. The method computes relative importance values of features in age prediction by measuring target metric before and after feature-column permutation ($R^2$). The underlying assumption is that permutation of important feature causes a greater reduction of prediction accuracy compared to the original prediction. On the other hand, non-important feature random displacement should not affect prediction to a significant degree. Due to the bias causing random permutation, significance scores for each feature can be averaged across results of k permutations. All significant scores can be calculated for each of the five trained models with subsequent averaging to avoid overfitting bias tendency.

$$PFI_{feature} = S_{original} - \frac{1}{K}\sum_{i=1}^{K} S_{shuffled(k)}$$

Where $S_{original}$ is the target metric score, $S_{shuffled}(k)$ is the target metric after the prediction with the permuted feature-column and is a bootstrap parameter that controls a number of permutation of each feature. Target metric can be chosen as metric $R^2$.

The ALE method may also be used. The ALE method estimates the influence of particular features on the age prediction by measuring, how the prediction changes on average upon small changes in feature values. ALE plots are assembled by first calculating local effects (LE) for each quantile (ALE Equation 1):

$$LE_Q = \frac{1}{N_Q}\sum_{j \in Q} F(C_j, Q) - F(C_j, Q-1); \quad \text{(ALE Equation 1)}$$

where: $N_Q$ is a number of samples in the interval between Qth and (Q-1)th quantiles of the target feature; $C_j$ is the abundance vector for a sample j that belongs to the interval; and $F(C_j, Q)$ is the predicted age for the vector, where the feature's Qth quantile value was substituted for the target feature value.

To produce ALEs, LEs are summed (ALE Equations 2):

$$ALE_1 = LE_1$$

$$ALE_Q = LE_Q + ALE_{Q-1} \quad \text{(ALE Equations 2)}$$

Additionally, ALEs are centered, so that the sum of all ALEs for a feature is zero.

In some embodiments, a gradient boosting classifier can be used. To verify the selected marker feature set a gradient boosting classifier was trained based on 96 features (95 from the marker set in Table 5 and a 96th, which equals all other microbe abundances). A data set can be separated into training and testing sets, with a training set containing 75% of all individuals. All samples can be separated into three groups: young (15-40 years), middle aged (41-60 years old) and old (61-90 years old) individuals. The classifier can be implemented using Python SciKit standart GradientBoostingClassifier class with the following settings: {'n_estimators': 100, 'max_depth': 4, 'min_samples_split': 4, 'learning_rate': 0.2, 'loss': 'deviance'}. Prediction quality metrics are shown in Table 3 for a one-vs-all setting, while Table 4 displays the quality of a random classifier. The disclosed list of markers provides a >25% edge over random in this simple setting.

In some embodiments, a method of predicting an organism's age can include models based on: neural networks, gradient boosting, random forest.

FIG. 1 shows predicted age versus an observed age in a DFS model. As such, FIG. 1 illustrates age predictions obtained with an example working embodiment of the invention. A Deep Feature Selection (DFS) pipeline was utilized to predict age for 3,058 microbiome samples (621 individuals) in a 5-fold 90-10% cross-validation setting. Microbiome profiles were obtained from open access projects, available at ENA and SRA archives (project IDs: ERP019502, ERP009422, SRP002163, ERP004605, ERP002469, ERP008729, ERP005534). The overall accuracy of this working embodiment allows the invention to predict a person's age with a mean absolute error (MAE) of 2.83 years.

Figure 2A:
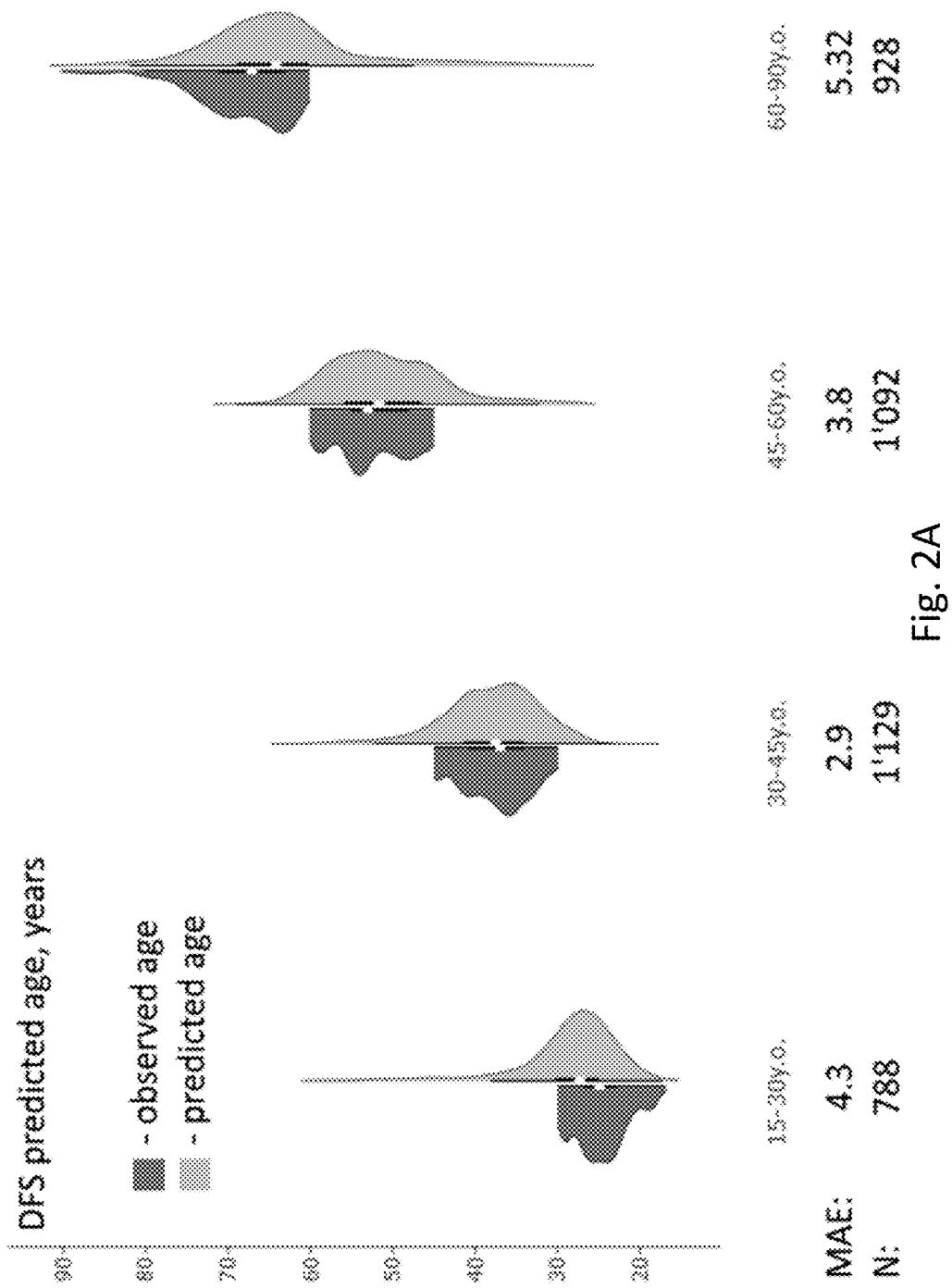
FIGS. 2A-2B show an observed age versus predicted age by age groups in a DFS model (FIG. 2A) and in an XGB model (FIG. 2B).
Figure 2B:
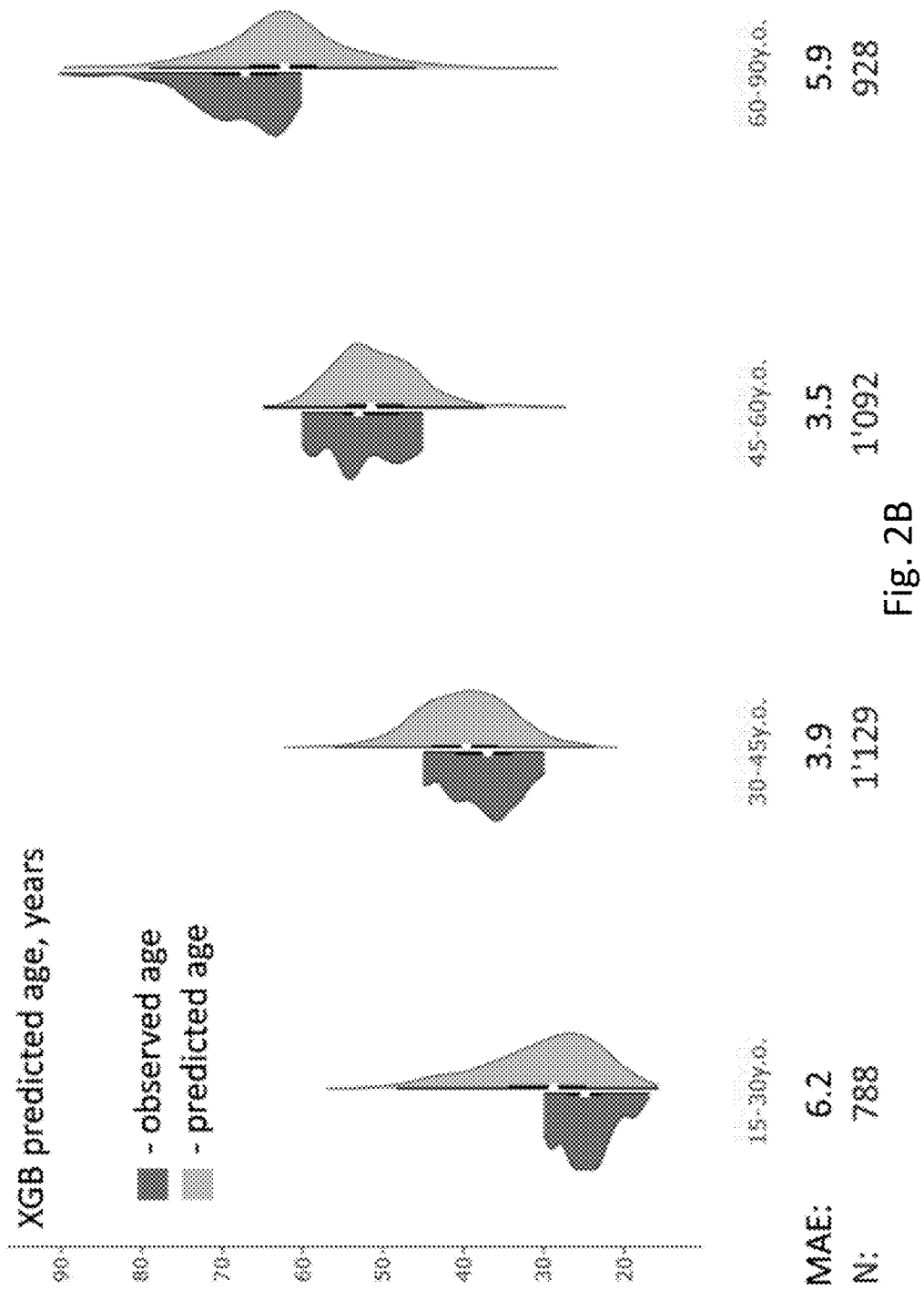

FIGS. 2A-2B show an observed age versus predicted age by age groups in a DFS model (FIG. 2A) and in an XGB model (FIG. 2B). The MAE for mean absolute error, N for number of samples for each age group. Accordingly, FIGS. 2A-2B provide a more detailed look at the accuracy of the example DFS (FIG. 2A) and XGB (FIG. 2B) working embodiments. The prediction error is non-uniformly distributed among different age groups being the lowest for people aged 30-60 years old.

Table 1 shows PFI importances, prevalence, and average abundance in DFS and XGB models. This model may be referred to as Model 1. As such, Table 1 provides information on the proposed microbiological marker set. XGB and DFS importance columns display decline in $R^2$ quality metrics upon permutation of corresponding features according to PFI method (average for five folds). Prevalence column displays the portion of samples in which the feature was detected reliably (cell count>10 cells/million) and Abundance column shows the average relative quantity of the microorganism in gut communities where it is detected.

TABLE 1

| Species | XGB importance | DFS importance | Mean importance | Prevalence, % | Abundance, % |
|---|---|---|---|---|---|
| Bacteroides vulgatus | 0.013 | 0.125 | 0.069 | 99.97 | 19.13 |
| Fusobacterium ulcerans | 0.035 | 0.087 | 0.061 | 4.16 | 2.37 |
| Bacteroides ovatus | 0.007 | 0.064 | 0.036 | 99.87 | 3.68 |
| Bifidobacterium bifidum | 0.016 | 0.032 | 0.024 | 90.21 | 1.05 |
| Chryseobacterium gallinarum | 0.038 | 0.009 | 0.023 | 57.38 | 0.15 |
| [Eubacterium] rectale | 0.008 | 0.038 | 0.023 | 99.89 | 6.64 |
| [Eubacterium] hallii | 0.012 | 0.031 | 0.021 | 99.24 | 1.14 |
| Bifidobacterium longum | 0.011 | 0.025 | 0.018 | 97.79 | 2.68 |
| Alistipes finegoldii | 0.005 | 0.029 | 0.017 | 99.47 | 2.82 |
| Faecalibacterium prousnitzii | 0.003 | 0.030 | 0.017 | 99.92 | 4.13 |
| [Clostridium] saccharolyticum | 0.025 | 0.008 | 0.016 | 81.50 | 0.04 |

TABLE 1-continued

| Species | XGB importance | DFS importance | Mean importance | Prevalence, % | Abundance, % |
|---|---|---|---|---|---|
| Ornithobacterium rhinotracheale | 0.018 | 0.012 | 0.015 | 95.21 | 0.29 |
| Bacteroides dorei | 0.004 | 0.026 | 0.015 | 99.84 | 6.64 |
| Parvimonas micra | 0.021 | 0.008 | 0.015 | 42.57 | 0.11 |
| Lactococcus lactis | 0.005 | 0.024 | 0.014 | 72.11 | 0.22 |
| Bifidobacterium adolescentis | 0.001 | 0.025 | 0.013 | 91.63 | 4.02 |
| Bifidobacterium catenulatum | 0.006 | 0.019 | 0.012 | 78.58 | 0.67 |
| Enterococcus faecalis | 0.016 | 0.008 | 0.012 | 63.43 | 0.13 |
| [Eubacterium] eligens | 0.005 | 0.019 | 0.012 | 98.26 | 2.53 |
| Roseburia hominis | 0.003 | 0.020 | 0.012 | 99.89 | 2.70 |
| Lachnoclostridium sp. YL32 | 0.019 | 0.004 | 0.011 | 91.00 | 0.11 |
| Bacteroides cellulosilyticus | 0.012 | 0.009 | 0.011 | 98.40 | 1.76 |
| Akkermansia muciniphila | 0.002 | 0.019 | 0.011 | 78.14 | 2.84 |
| Parabacteroides distasonis | 0.003 | 0.017 | 0.010 | 99.42 | 1.43 |
| Bifidobacterium pseudocatenulatum | 0.005 | 0.014 | 0.010 | 87.69 | 1.24 |
| Bacteroides caccae | 0.003 | 0.016 | 0.010 | 98.58 | 2.25 |
| Ruminococcus bicirculans | 0.002 | 0.017 | 0.009 | 98.82 | 1.93 |
| Methanobrevibacter smithii | 0.012 | 0.006 | 0.009 | 57.96 | 1.94 |
| Escherichia coli | 0.006 | 0.011 | 0.009 | 89.87 | 0.77 |
| Prevotella intermedia | 0.014 | 0.003 | 0.008 | 90.53 | 0.14 |
| Megasphaera elsdenii | 0.003 | 0.013 | 0.008 | 68.56 | 0.90 |
| [Clostridium] bolteae | 0.003 | 0.013 | 0.008 | 99.68 | 0.48 |
| Flavonifractor plautii | 0.003 | 0.012 | 0.008 | 99.58 | 0.55 |
| Streptococcus gordonii | 0.013 | 0.002 | 0.008 | 56.27 | 0.02 |
| Barnesiella viscericola | 0.001 | 0.014 | 0.008 | 96.55 | 0.75 |
| Anaerostipes hadrus | 0.006 | 0.009 | 0.008 | 99.42 | 2.23 |
| Bacteroides caecimuris | 0.007 | 0.008 | 0.007 | 99.63 | 1.02 |
| Eggerthella lenta | 0.003 | 0.012 | 0.007 | 97.08 | 0.41 |
| Odoribacter splanchnicus | 0.006 | 0.009 | 0.007 | 99.74 | 1.97 |
| Bacteroides fragilis | 0.005 | 0.009 | 0.007 | 99.37 | 1.68 |
| Shigella sp. PAMC 28760 | 0.001 | 0.013 | 0.007 | 60.72 | 2.24 |
| Rhodococcus sp. YL-1 | 0.012 | 0.001 | 0.007 | 2.45 | 0.01 |
| Acidaminococcus fermentans | 0.002 | 0.012 | 0.007 | 40.23 | 0.36 |
| Campylobacter jejuni | 0.006 | 0.008 | 0.007 | 86.90 | 0.03 |
| Streptococcus parasanguinis | 0.003 | 0.009 | 0.006 | 89.16 | 0.10 |
| Bifidobacterium angulatum | 0.004 | 0.008 | 0.006 | 67.98 | 0.26 |
| Negativicoccus massiliensis | 0.007 | 0.005 | 0.006 | 35.70 | 2.11 |
| Veillonella parvula | 0.004 | 0.007 | 0.006 | 84.35 | 0.11 |
| Streptococcus salivarius | 0.003 | 0.008 | 0.005 | 95.03 | 0.39 |
| Streptococcus anginosus | 0.004 | 0.007 | 0.005 | 93.76 | 0.46 |
| Victivallales bacterium CCUG 44730 | 0.001 | 0.009 | 0.005 | 62.09 | 0.46 |

TABLE 1-continued

| Species | XGB importance | DFS importance | Mean importance | Prevalence, % | Abundance, % |
|---|---|---|---|---|---|
| *Parabacteroides* sp. CT06 | 0.002 | 0.008 | 0.005 | 99.61 | 2.89 |
| *Streptococcus thermophilus* | 0.005 | 0.005 | 0.005 | 79.35 | 0.51 |
| *Bacteroides salanitronis* | 0.004 | 0.006 | 0.005 | 97.63 | 0.29 |
| *Hafnia* sp. CBA7124 | 0.005 | 0.004 | 0.005 | 10.79 | 0.37 |
| *Christensenella massiliensis* | 0.001 | 0.008 | 0.005 | 97.61 | 0.58 |
| *Bacteroides thetaiotaomicron* | 0.003 | 0.007 | 0.005 | 99.95 | 3.73 |
| *Bifidobacterium dentium* | 0.004 | 0.005 | 0.004 | 56.62 | 0.09 |
| *Cloacibacillus porcorum* | 0.003 | 0.006 | 0.004 | 72.80 | 0.10 |
| *Streptococcus constellatus* | 0.003 | 0.005 | 0.004 | 82.22 | 0.36 |
| *Haemophilus parainfluenzae* | 0.005 | 0.004 | 0.004 | 68.19 | 0.07 |
| *Pseudomonas aeruginosa* | 0.006 | 0.002 | 0.004 | 6.00 | 0.01 |
| *Intestinimonas butyriciproducens* | 0.003 | 0.005 | 0.004 | 98.97 | 0.40 |
| *Clostridium* sp. SY8519 | 0.004 | 0.003 | 0.004 | 89.90 | 0.09 |
| *Desulfovibrio fairfieldensis* | 0.002 | 0.005 | 0.004 | 15.34 | 0.17 |
| *Blautia hansenii* | 0.003 | 0.004 | 0.004 | 98.50 | 0.35 |
| *Prevotella jejuni* | 0.002 | 0.005 | 0.003 | 49.80 | 0.09 |
| *Lactobacillus amylovorus* | 0.002 | 0.005 | 0.003 | 50.17 | 0.21 |
| *Oxalobacter formigenes* | 0.003 | 0.004 | 0.003 | 20.26 | 0.26 |
| *Adlercreutzia equolifaciens* | 0.002 | 0.005 | 0.003 | 87.13 | 0.38 |
| *Acidaminococcus intestini* | 0.002 | 0.004 | 0.003 | 56.01 | 0.79 |
| *Dialister pneumosintes* | 0.002 | 0.004 | 0.003 | 59.69 | 0.10 |
| *Erysipelotrichaceae bacterium* I46 | 0.002 | 0.004 | 0.003 | 91.45 | 0.07 |
| *Comamonas kerstersii* | 0.002 | 0.003 | 0.003 | 8.95 | 0.22 |
| *Enterococcus faecium* | 0.004 | 0.001 | 0.002 | 89.95 | 0.03 |
| *Coriobacteriaceae bacterium* 68-1-3 | 0.003 | 0.002 | 0.002 | 46.38 | 0.02 |
| *Bifidobacterium breve* | 0.003 | 0.002 | 0.002 | 94.50 | 0.09 |
| *Collinsella aerofaciens* | 0.002 | 0.002 | 0.002 | 89.77 | 0.93 |
| *Mordavella* sp. Marseille-P3756 | 0.001 | 0.003 | 0.002 | 98.47 | 0.44 |
| *Bacteroides helcogenes* | 0.002 | 0.002 | 0.002 | 82.72 | 0.03 |
| *Prevotella melaninogenica* | 0.001 | 0.003 | 0.002 | 51.88 | 0.07 |
| *Lactobacillus ruminis* | 0.001 | 0.003 | 0.002 | 49.96 | 0.17 |
| *Rothia mucilaginosa* | 0.003 | 0.001 | 0.002 | 82.74 | 0.05 |
| *Turicibacter* sp. H121 | 0.002 | 0.002 | 0.002 | 83.71 | 0.07 |
| *Klebsiella* sp. 2N3 | 0.002 | 0.002 | 0.002 | 35.73 | 0.98 |
| *Hafnia alvei* | 0.001 | 0.002 | 0.002 | 14.84 | 0.16 |
| *Clostridium cochlearium* | 0.002 | 0.002 | 0.002 | 56.72 | 0.01 |
| *Gordonibacter urolithinfaciens* | 0.001 | 0.002 | 0.002 | 84.77 | 0.13 |
| *Propionibacterium freudenreichii* | 0.001 | 0.002 | 0.002 | 16.73 | 0.07 |
| *Lactobacillus reuteri* | 0.002 | 0.002 | 0.002 | 9.73 | 0.33 |

TABLE 1-continued

| Species | XGB importance | DFS importance | Mean importance | Prevalence, % | Abundance, % |
|---|---|---|---|---|---|
| Eggerthella sp. YY7918 | 0.002 | 0.002 | 0.002 | 76.43 | 0.03 |
| Streptococcus acidominimus | 0.002 | 0.001 | 0.002 | 57.22 | 0.02 |
| Campylobacter coli | 0.001 | 0.001 | 0.001 | 92.45 | 0.02 |
| Chryseobacterium taklimakanense | 0.001 | 0.001 | 0.001 | 44.86 | 0.08 |
| Porphyromonas asaccharolytica | 0.001 | 0.001 | 0.001 | 25.89 | 0.17 |

In some aspects, the microorganisms of Table 1 are a specific group, and are used as a specific combination, herein "Group 95," as defined above, which designates the 95 specific members in the group. Accordingly, each of the 95 different types of recited microorganisms is present in Group 95.

Figure 3:
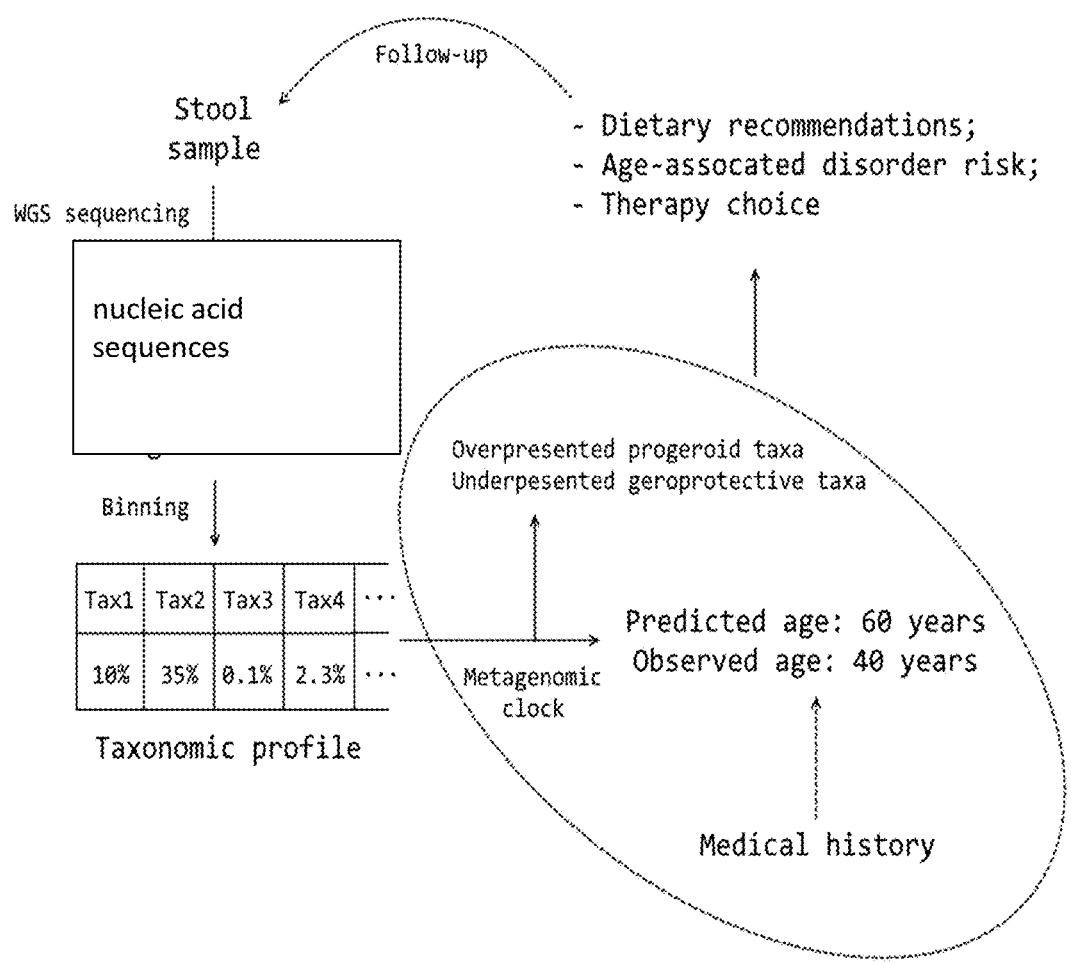
FIG. 3 shows an example working embodiment for medical purposes.

FIG. 3 shows an example working embodiment for medical purposes. Particularly, FIG. 3 displays a scheme of several working embodiments that can be used by medical professionals. Classical metagenomic approaches can be used to produce a person's gut microflora taxonomic profile or in another microbiota of the person. This profile is subsequently analyzed using the invention to determine whether the donor's microflora shows any signs of accelerated aging. If the invention-derived metagenomic clock displays that their microflora is typical for significantly older people, a piece of software can pinpoint specific alterations causing this effect. A medical professional can then assess this information (combined with personal data) to provide lifestyle advice, choose better treatment for patients or plan a diet that would support "geroprotective" (e.g., beneficial or related to being phenotypically younger) microbes and suppress "progeroid" (e.g., harmful or related to being phenotypically older) microbes in the gut or other location.

FIG. 4 shows an importance rank comparison of 74 microbial taxa assigned by DFS and XGB age predicting models for all samples (0-90 year old) and 15-30, 30-45, 45-60 and 60-90 age groups. Accordingly, FIG. 4 illustrates the microbial species that are the most important for accurate age prediction in each age group as indicated by PFI scores derived from two age prediction models (XGB and DFS). The PFI score is the drop in $R^2$ upon feature permutation and the features with the higher score are rendered more important for model performance. Twenty most important features for accurate prediction of 15-30, 30-45, 45-60 and 60-90 age group samples as well as in the all samples (aged 0-90 years) were combined to create a list of 76 features. Their PFI score ranks in each group were plotted on a heatmap (black corresponds to the most important feature), rows (importance vectors for a feature within one model and age group) and columns were reordered based on Manhattan distance to show similarities. Feature importances for XGB and DFS models are highly similar, but they rely on different features while making predictions for different age groups.

Table 2 shows the name associated with each number identifier of FIG. 4.

| | |
|---|---|
| 1 | Aeromonas salmonicida |
| 2 | Collinsella aerofaciens |
| 3 | Clostridioides difficile |
| 4 | Prevotella jejuni |
| 5 | Desulfovibrio fairfieldensis |
| 6 | Prevotella melaninogenica |
| 7 | Cloacibacillus porcorum |
| 8 | Streptococcus anginosus |
| 9 | Negativicoccus massiliensis |
| 10 | Bacteroides cellulosilyticus |
| 11 | Parvimonas micro |
| 12 | Pseudomonas aeruginosa |
| 13 | Victivallales bacterium CCUG 44730 |
| 14 | Faecalibacterium prausnitzii |
| 15 | Eubacterium sulci |
| 16 | Streptococcus gordonii |
| 17 | Akkermansia muciniphila |
| 18 | Eubacterium eligens |
| 19 | Shigella sp. PAMC 28760 |
| 20 | Ruminococcus biciruclans |
| 21 | Eggerthella lento |
| 22 | Blautio hansenii |
| 23 | Campylobacter coli |
| 24 | Streptococcus acidominimus |
| 25 | Lachnoclostridium sp. YL32 |
| 26 | Oxalobacter formigenes |
| 27 | Odoribacter splanchnicus |
| 28 | Bifidobacterium pseudocatenulatum |
| 29 | Bacteroides caccae |
| 30 | Flavonifractor plautii |
| 31 | Streptococcus salivarius |
| 32 | Campylobacter jejuni |
| 33 | Alistipes finegoldii |
| 34 | Ornithobacterium rhinotracheale |
| 35 | Anaerostipes hadrus |
| 36 | Prevotella intermedia |
| 37 | Eubacterium rectale |
| 38 | Bifidobacterium longum |
| 39 | Bifidobacterium bifidum |
| 40 | Bacteroides vulgatus |
| 41 | Veillonella parvula |
| 42 | Parabacteroides distasonis |
| 43 | Bacteroides salanitronis |
| 44 | Roseburia hominis |
| 45 | Porphyromonas gingivalis |
| 46 | Escherichia coli |
| 47 | Bifidobacterium catenulatum |
| 48 | Adlercreutzia equolifaciens |
| 49 | Enterococcus faecalis |
| 50 | Erysipelotrichaceae bacterium I46 |
| 51 | Barnesiella viscericola |
| 52 | Enterobacter hormaechei |
| 53 | Megasphaera elsdenii |
| 54 | Bacteroides caecimuris |
| 55 | Bifidobacterium angulatum |
| 56 | Clostridium bolteae |
| 57 | Eubacterium limosum |
| 58 | Olsenella sp. Marseille-P2300 |
| 59 | Clostridium saccharolyticum |
| 60 | Coriobacteriaceae bacterium 68-1-3 |
| 61 | Eubacterium hallii |
| 62 | Lactococcus lactis |
| 63 | Candidatus Methanomethylophilus alvus |
| 64 | Bacteroides ovatus |

| | |
|---|---|
| 65 | *Clostridium cochlearium* |
| 66 | *Rhodococcus* sp. YL-1 |
| 67 | *Fusobacterium ulcerans* |
| 68 | *Bacteroides fragilis* |
| 69 | *Bacteroides dorei* |
| 70 | *Chryseobacterium gallinarum* |
| 71 | *Parabacteroides* sp. CT06 |
| 72 | *Bifidobacterium adolescentis* |
| 73 | *Lactobacillus amylovorus* |
| 74 | *Comamonas kerstersii* |
| 75 | *Intestinimonas butyriciproducens* |
| 76 | *Methanobrevibacter smithii* |

In some aspects, the microorganisms of Table 2 are a specific group, and are used as a specific combination, herein "Group 76," which designates the 76 specific members in the group. Accordingly, each of the 76 different types of recited microorganisms is present in Group 76.

Figure 5:
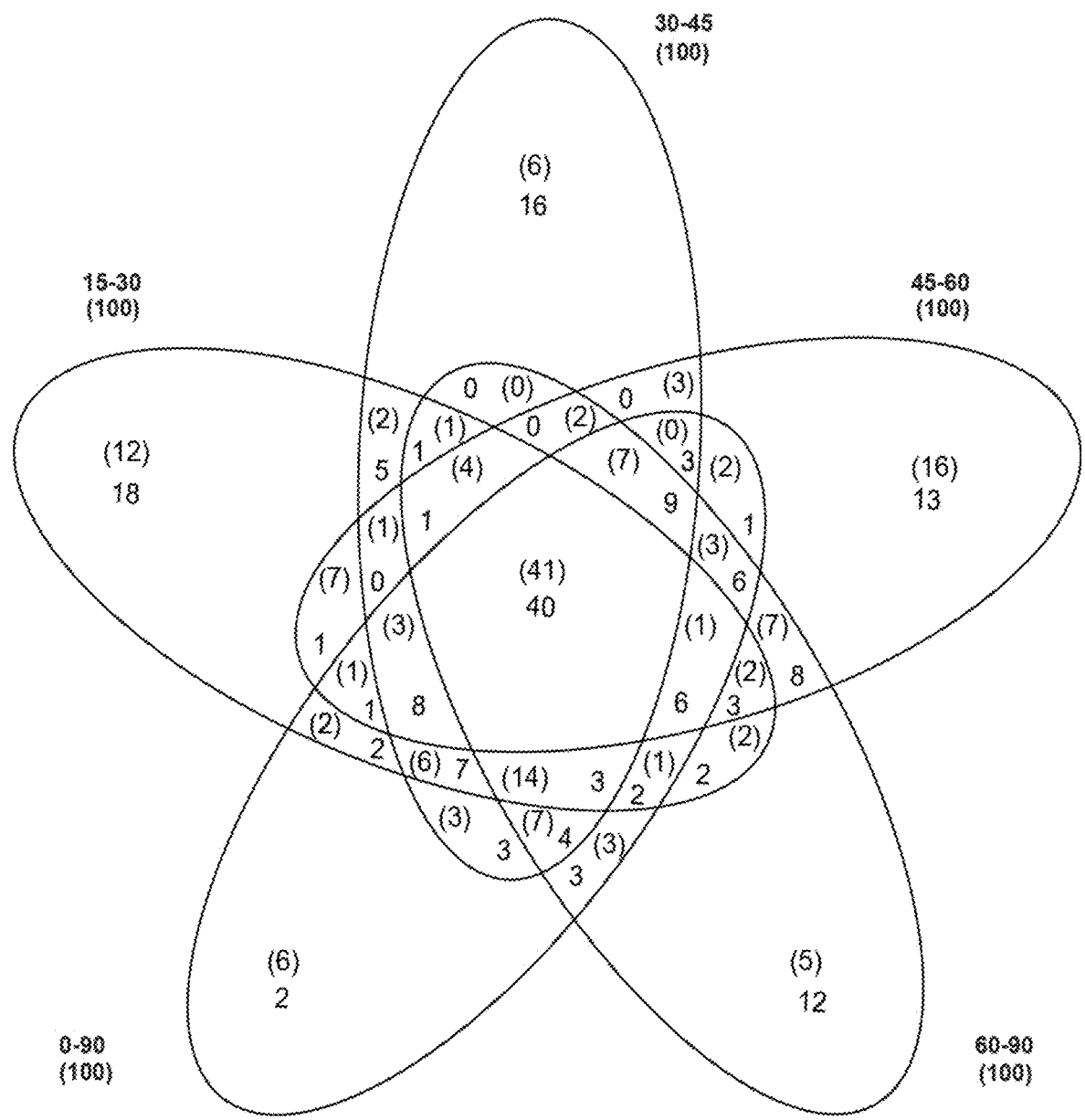
FIG. 5 shows a Venn diagram for 100 most important microbial taxa for age prediction by two machine learning methods.

FIG. 5 shows a Venn diagram for 100 most important microbial taxa for age prediction by two machine learning methods. Accordingly, FIG. 5 illustrates overlaps between 100 of the most important features in each age group as measured by PFI. Integers in parentheses indicate overlaps in XGB derived features, and non-parentheses integers indicate overlaps in DFS derived features. In both models, 40-41 features can be spotted in 100 most important feature lists for all age groups and no age group has >18 unique features in such a list.

Figure 7:
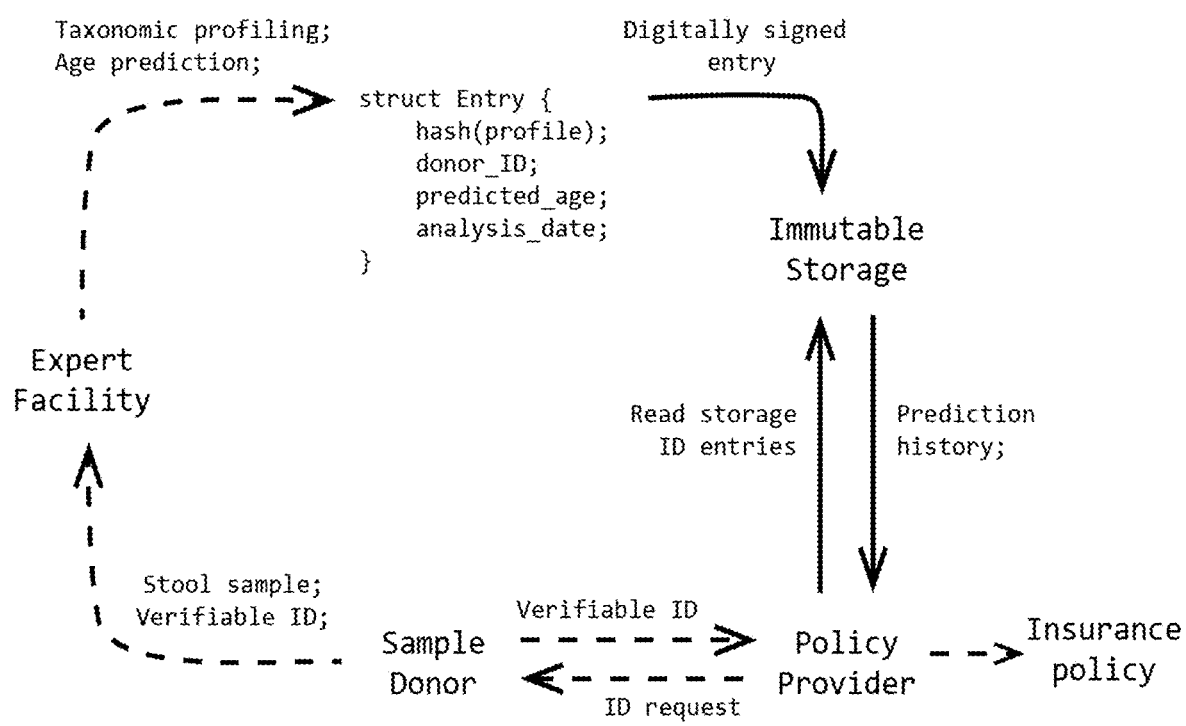
FIG. 7 shows a working embodiment for insurance industry.

FIG. 7 shows a working embodiment for insurance industry. As such, FIG. 7 displays a simplified scheme of an insurance working embodiment of the invention. Age prediction based on intestinal microbiome or from another microbiota can be requested from a potential policy holder by a policy provider to modify the terms of the insurance policy contract. The policy holder then proceeds to a designated facility that runs microbiome screening and interpretation, using the method and/or markers specified in herein. Test results are then stored on an immutable storage with enabled smart contracts and can be accessed by anyone possessing the sample donor ID. By sharing their ID, the donor lets the policy provider inspect their gut microflora (or other microbiota) level or progression (e.g., over time) and corresponding age predictions. This information is then factored in by the policy provider to calculate life insurance discounts or by a third party to evaluate a viatical settlement cost. However, any type of insurance provider can use this embodiments. Also, this embodiment can be modified for any industry, such as medical, or service and commodity that has a contract. The policy provider can be replaced to a contract administrator for any type of contract, which can be modified based on the predicted biological age (i.e., results of biological clock model), where one or a series of results can be used for preparing or modifying a contract for any goods or services.

Table 3 shows a gradient boosting classifier performance. As such, Table 3 illustrates the predicting power of the specified marker list provided herein. A gradient boosting classifier was trained on 75% of the available data and tested on 842 samples. Relative abundances from only 95 (out of 1673 total) microbial taxa were used. The quality metrics are calculated as in a one-vs-all setting. TP stands for True Positive (number of right assignments to this age group), FP stands for False Positive (number of faulty assignments to the group), FN stands for False Negative (number of samples belonging to this group, but assigned to another one), TN stands for True Negative (number of samples correctly not assigned to this group). Precision equals TP/(TP+FP) (measures the portion of correct assignments to this group among all assignments), Miss equals FN/(FN+TP) (measures the portion of test samples that should have been assigned to this group, but were assigned to another one), Accuracy equals (TP+TN)/(#Samples) (measures the number of correct assignments among all samples in the one-vs-all context). P-value is defined as the portion of prediction vector permutations that give better than observed accuracy. None of such permutation (among 10'000 iterations) has provided better accuracy.

Table 4 shows random (equiprobable) assignment of samples to age groups. As such, Table 4 provides a frame of reference for Table 3. The metrics are derived from equiprobable assignment of samples to each age group. P-value is calculated as a number of permutations of the original prediction vector that provide better accuracy than equiprobable assignment. Some random permutations have provided better classification accuracy, which shows that the gradient boosting model (Table 3) performs significantly better than equiprobable assignment.

TABLE 3

| | Age group | | | |
|---|---|---|---|---|
| | 15-30 | 31-60 | 61-90 | total |
| Number of samples | 378 | 265 | 199 | 842 |
| TP | 320 | 194 | 133 | |
| FP | 58 | 83 | 54 | |
| FN | 58 | 71 | 66 | |
| TN | 406 | 494 | 589 | |
| Precision | 0.85 | 0.7 | 0.71 | |
| Miss | 0.15 | 0.27 | 0.33 | |
| Accuracy | 0.86 | 0.82 | 0.86 | |
| P-value | <0.0001 | <0.0001 | <0.0001 | |

TABLE 4

| | Age group | | | |
|---|---|---|---|---|
| | 15-30 | 31-60 | 61-90 | total |
| Number of samples | 373 | 265 | 199 | 842 |
| TP | 134 | 98 | 68 | |
| FP | 144 | 187 | 211 | |
| FN | 244 | 167 | 131 | |
| TN | 320 | 390 | 432 | |
| Precision | 0.48 | 0.34 | 0.24 | |
| Miss | 0.65 | 0.63 | 0.66 | |
| Accuracy | 0.54 | 0.58 | 0.59 | |
| P-value | 0.0097 | 0.0719 | 0.019 | |

Figure 8X:
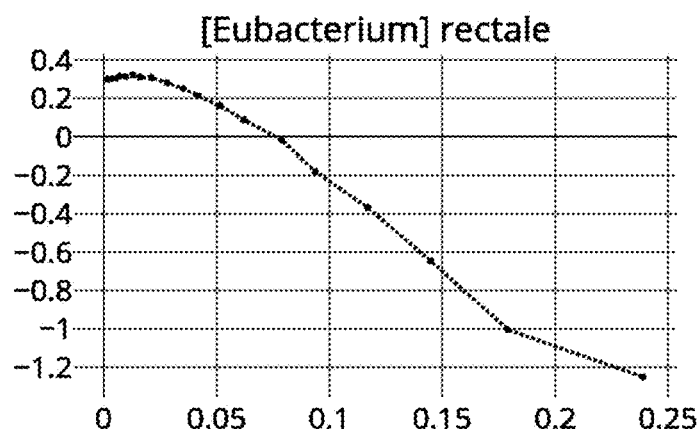

FIGS. 8A-8X show ALE plots for 24 features in DFS model. FIG. 8Y shows the calculated ALE values for FIGS. 8A-8X. Accordingly, FIGS. 8A-8X contain ALE plots for 24 features picked from 100 most important features in the DFS model. X-axis displays relative abundance of a microbe, Y axis displays change accumulated local effect (ALE) measured in years. The ALE shows how predictions change on average upon incrementing the target feature. Dots represent quantiles of the feature distribution (ALE was calculated for 1% through 95% quantiles with 5% increments). ALEs were calculated based only on samples with non-zero target feature values. In some aspects, the microorganisms of this paragraph and shown in FIGS. 8A-8X are a specific group, and are used as a specific combination, herein "Group 24," which designates the 24 specific members in the group.

Accordingly, each of the 24 different types of recited microorganisms is present in Group 24.

FIG. 12 shows the calculated ALE values for another group of microorganisms. In some aspects, the microorganisms of this paragraph and shown in FIG. 12 are a specific group, and are used as a specific combination, herein "Group 19," which designates the 19 specific members in the group. Accordingly, each of the 19 different types of recited microorganisms is present in Group 19.

FIG. 13 shows the calculated ALE values for another group of microorganisms. In some aspects, the microorganisms of this paragraph and shown in FIG. 13 are a specific group, and are used as a specific combination, herein "Group 13," which designates the 13 specific members in the group. Accordingly, each of the 13 different types of recited microorganisms is present in Group 13.

FIGS. 9A and 9B provide some instructions for using ALE plots. Accordingly, FIGS. 9A and 9B include a visual instruction to interpreting ALE plots. FIG. 9A is an example of a potentially geroprotective microbe, whose increase in abundance is associated with lower predicted age. FIG. 9B is a potential progeroid microbe, whose increase in abundance produces older predictions on average. In this particular example, increasing [Eubacterium] halii abundance by 0.8% leads to an increase in predicted age by 0.57 years on average.

Figure 10A:
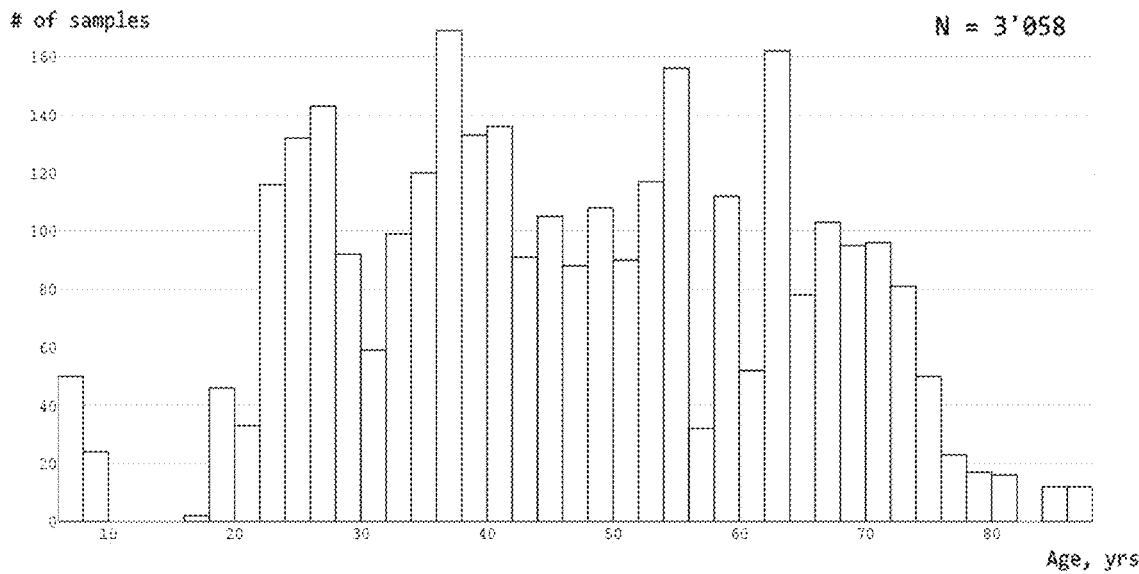
FIGS. 10A and 10B show exemplary age distributions in samples.
Figure 10B:
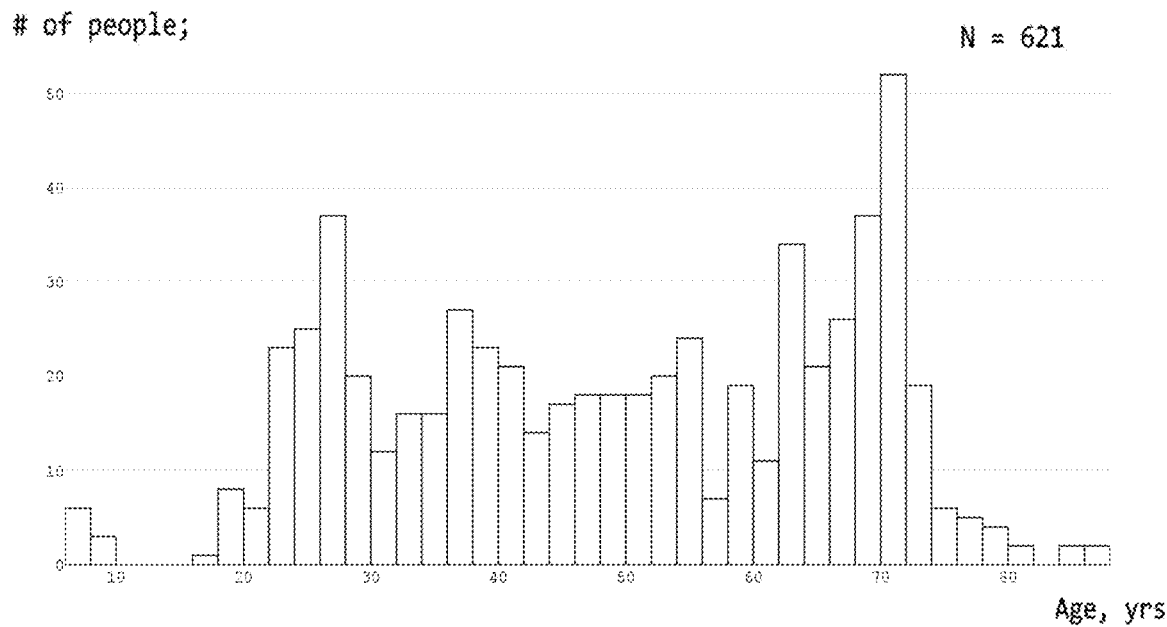

FIGS. 10A and 10B show exemplary age distributions in samples. Accordingly, FIGS. 10A and 10B illustrate the age distribution of data used for model training both on sample (FIG. 10A) and individual (FIG. 10B) levels.

Figure 11:
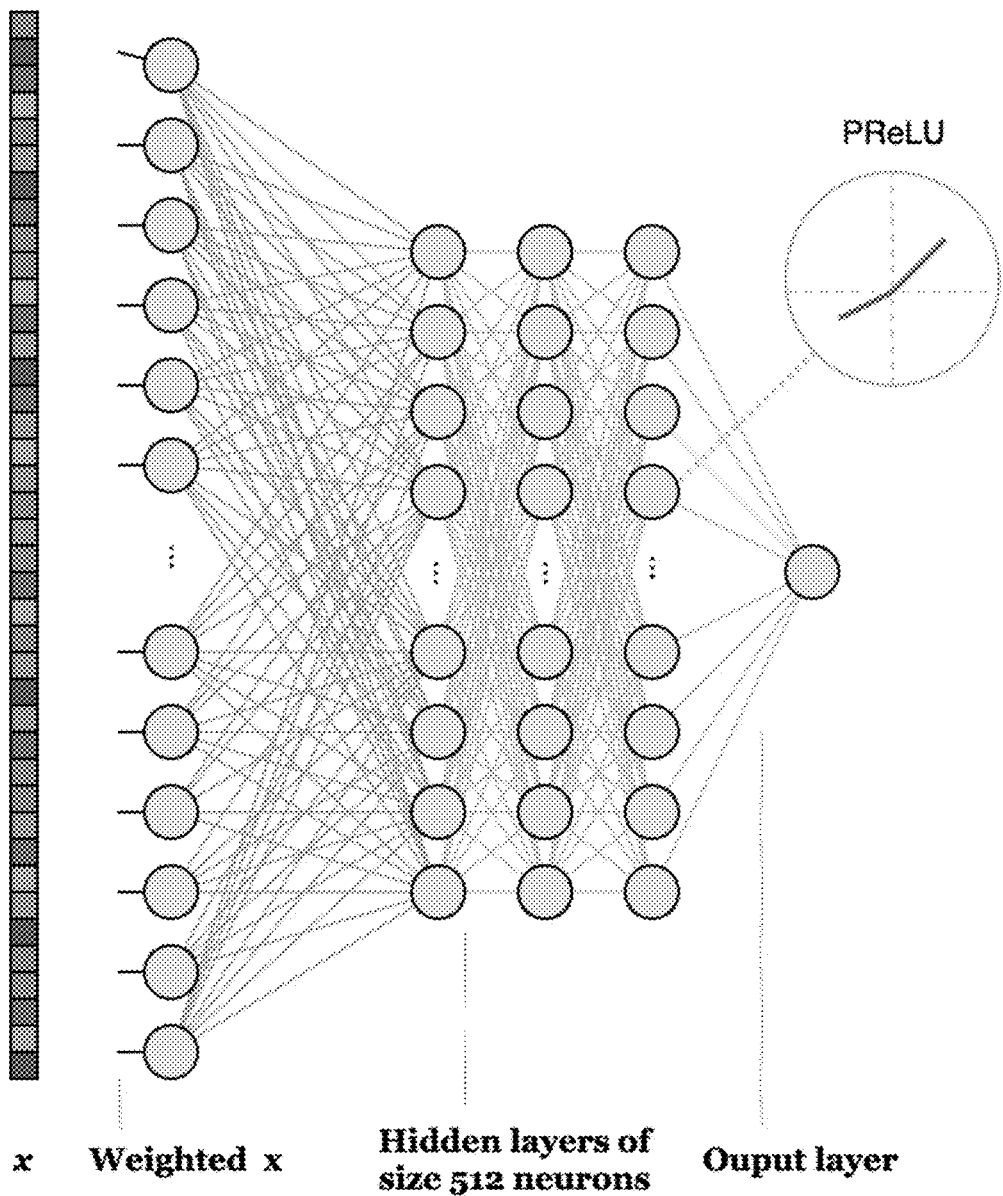
FIG. 11 shows the schematic depiction of the best configuration among tested neural networks for DFS application.

FIG. 11 shows the schematic depiction of the best configuration among tested neural networks for DFS application. As such, FIG. 11 includes schematic depiction of the best configuration among tested neural networks for DFS application. It has 3 hidden layers with 512 neurons in each one, utilizes PReLU activation function and is set to 0.001 learning_rate. "x" is the input vector of features (i.e. microbial species relative abundances).

In some embodiments, kits are provided for collection of microflora material and subsequent metagenome sequencing with the purpose of assessing a subject's (e.g., sample donor) phenotypic age. Such kits can include instructions for employing protocols based on human microbiota (e.g., gut microbiota) metagenome sequencing. The kit can also include nucleic acids of the disclosed microbiological marker set. The kit can include instructional protocols that may vary in sample preparation, sequencing platform and strategy as well as quality control measures, normalization techniques, taxonomic assignment and abundance calculation algorithms.

In some embodiments, applications of methods described herein can be used to assess other organismal properties that are dependent on chronological age, where differences in the calculated biological age compared with the actual chronological age are used to determine the presence of a disease state. For example, the methods can be used to estimate aging associated disease or disorder risks, or provide medical advice based on the predicted phenotypical age.

In some embodiments, the methods may use the whole set of disclosed microbiological markers, as well as on its subset or a set of higher order taxa that consist of the mentioned markers. For example, some working embodiments may utilize amplicon based sequencing techniques that do not provide species level resolution, but can be used to assess microbiome community profile at a genus level.

In some embodiments, the present invention can be used for medical purposes. As such, the invention can include kits and pipelines utilizing the disclosed set of marker microbes in order to provide advice on lifestyle and diet as well as other factors, such as therapies or changes in lifestyle or diet. The invention can aid medical professionals in choosing a medication, therapy, or dietary interventions based on a patient's microbiota (e.g., gut microbiota) composition or functional capabilities derived from it.

In some embodiments, specialized databases, consulting software, extensions to existing patient card systems, healthcare guidelines, kits and pipelines (as well as laboratories utilizing them) based on measures of chronological age can derived with the help of the disclosed marker set and the methods described herein.

In some embodiments, the microbe markers and methods can be used in a forensic context in order to verify or establish a person's identity. Forensic embodiments can include but are not limited to a legally effective certification system, expert witness institutions, and laboratories providing metagenome based age verification. All such embodiments can utilize the aforementioned protocols to leverage information contained within a person's microbiota (e.g., gut) metagenome.

In some embodiments, the microbe markers and methods can be used in a scientific context in order measure the effectiveness of novel therapies. For example, changes in gut microbiota derived age during a geroprotective compound screening study can be used to help identify the most potent drug candidates.

In some embodiments, microbiological clocks can be generated with the microbes and methods in order to track and compare aging speed in different populations and/or different individuals. Such microbiological clocks can be used in combination with biological pathway information, metabolic or strain profiling of gut metagenome, or host genomic information to produce new hypotheses in gerontology, microbiology, immunology and general molecular biology fields.

All the example usages of the disclosed microbiological markers can vary in protocol details, accuracy, legal status, final purpose, but are still based on the core idea of chronological age and/or phenotypic age being tied with a subject's microflora (e.g., gut microflora) contained indicators. Similarly, all future practical applications of the invention can be modified while still being subject to the markers and methods described herein Thus, the list of possible working embodiments is not limited to the ones mentioned herein and can be greatly extended by professionals.

In some embodiments, a method of predicting an individual's phenotypical age based on their microbiome taxonomic profile is provided as follows: (a) isolating DNA or other nucleic acid from a sample of an individual's microbiome, or obtaining otherwise obtaining the nucleic acids; (b) estimating relative abundances of microbial taxa in the sample with WGS techniques to produce a taxonomic profile of the microbiota or otherwise obtaining the estimated relative abundances; and (c) processing the taxonomic profile with a machine learning platform in order to predict the phenotypical age of the sample donor. The taxonomic features can include the microbes described herein, or sets thereof in the different tables or different figures. In some aspects, step (c) uses the derivative information of the microbes, such as absolute abundance, genus level profile, taxon specific gene counts, ecological group abundance or others. In some aspects, the biological sample is processed to provide a taxonomic profile with strains, species or genus resolution. or such taxonomic profile is provided as data from a database. In some aspect, the taxonomic profile is based on 16S variable regions or whole metagenome reads. In some aspects, step (b) produces a relative or absolute abundance taxonomic profile. In some aspect, the taxonomic profile obtained with step (b) is used to comprise a corresponding functional profile of donors' microbiota. In some aspect, the sample in step (a) is a sample of non-gut microbiome (e.g. urogenital, cutaneous, oral), or a gut microbiome. In some aspect, the sample donor is human, but may be a non-human animal.

In some embodiments, the methods can include comparing the metagenomic profile to reference profiles in order to find similar microbial compositions that produce different age predictions, microflora alterations that could affect the prediction and to report the suggested alterations to the donor of the sample.

In some embodiments, the methods can include making a compilation of metagenomic profiles with personal data, such as images, medical history, biometrics, geographical location in order to explore correlations between predicted age and said personal data.

In some embodiments, the sample is a gut metagenome that is obtained either with stool collection or biopsy.

In some embodiments, the methods can include using the resulting age prediction as a measure of phenotypic age. The method can also include reporting the predicted phenotypic age to the sample donor. The predicted phenotypic age can be compared to the actual chronological age of the subject, and differences thereof can be used to make predictions about health.

In some embodiments, the methods can also include identifying at least one microbe or group of microbes whose change in abundance would affect a sample donor's prediction and reporting this information to them.

In some embodiments, the methods can include comparing a sample donor's profile to a reference database, assessing their risk of developing age associated disorders, and reporting this information regarding their risk to the sample donor.

In some embodiments, the method include creating a dietary plan designed to support or suppress specific microbes whose change in abundance would affect the prediction and delivering the plan to the sample donor.

In some embodiments, the method can include generating a recommended therapy for an individual based on comparing their metagenomic profile and age prediction with the reference database, and reporting the therapy to them.

In some embodiments, the method can include assessing multiple metagenomic profiles at once to discover common determinants of microbiome ageing, and using this information to suggest microflora alterations that can affect a group of people. Which can include modulating the predicted age. The methods can include creating a database of reference profiles and their corresponding predictions. The methods can include information on at least one specific microbe's influence on age prediction that allows for creating microflora interventions able to change the predictions, developing such interventions, and providing the microflora interventions to the sample donors, subjects, or the general public.

In some embodiments, the methods can include designing consumer goods based on generalizing information in a reference database, and delivering the goods to a consumer. In some aspects, the methods can include creating a cosmetics product designed to support or suppress specific microbes whose change in abundance would affect the prediction, and delivering the product to the sample donors, subjects, or the general public. In some aspects, the methods can include creating a dietary product designed to support or suppress specific microbes whose change in abundance would affect the prediction and delivering the product to the sample donors, subjects, or the general public. In some aspects, the methods can include creating a medical product designed to support or suppress specific microbes whose change in abundance would affect the prediction and delivering the product to the sample donors, subjects, or the general public. In some aspects, the methods can include creating clothes designed to support or suppress specific microbes whose change in abundance would affect the prediction and delivering the product to the sample donors, subjects, or the general public.

In some embodiments, the methods can include creating software comparing a user's microbiological profiles to a reference database, and providing information on specific microbes' influence on the user's age prediction, and reporting this information to the user. In some aspects, the database is realized as a blockchain storage to track user's microbiological profile progression and its derived age progression. In some aspect, the personal data can be shared only upon its owner cryptographically assured agreement.

In some embodiments, the methods can be used in developing insurance policies based on analyzing the reference database and delivering policies to customers. In some aspects, a policy holder's payment rate is influenced by age prediction derived from their microbiological profile. In some aspects, a policy holder is expected to provide verified dynamics of their microbiological profile and corresponding age predictions.

The invention further provides for methods for predicting age of a subject based on age-associated microflora comprising: (a) obtaining a biological sample of the subject or nucleic acids thereof; (b) determining the amount/percentage of one or more gene(s) associated with age-associated microflora marker(s) whose amount/percentage changes with age, or obtaining the data thereof from a database or from an analysis performed off-site; (c) comparing the amount/percentage of one or more gene(s) associated with age-associated microflora marker(s) whose amount/percentage changes with age with the change of the same microflora from an age correlated reference population; and (d) obtaining a value or range of values for the predicted age of the subject; wherein comparing the amount/percentage of one or more gene(s) associated with age-associated microflora marker(s) whose amount/percentage changes with age with the expression of the same gene(s) from an age correlated reference population comprises any statistical method, multivariate regression method, linear regression analysis, tabular method, or graphical method used to predict the age of a subject based on expression of gene(s) associated with age-associated microflora marker(s) whose amount/percentage changes with age; thereby predicting age (e.g., phenotypic age) of a subject.

In some embodiments, a method can include developing a drug therapy based on the output predicted phenotypic age. In some aspects, a method can include developing a senolytic therapy based on the generated output predicted phenotypic age. In some aspects, a method can include developing a senoremediation therapy based on the generated output predicted phenotypic age.

In some embodiments, a method of predicting a phenotypical age of a subject based on a microflora taxonomic profile of a microbiota of the subject can include: isolating a plurality of microorganism nucleic acids of microorganisms from a sample of a microbiota of the subject or otherwise obtaining the nucleic acids; analyzing the plurality of microorganism nucleic acids to determine the amount of the microorganisms of the microbiota based on the plurality of microorganism nucleic acids or otherwise receiving data about the amount of microorganisms; generating a taxonomic profile of the microbiota of the subject based on the amount of each of the microorganisms or otherwise receiving data of the taxonomic profile; processing the taxonomic profile of the microbiota with a computer configured with a machine learning platform (e.g., machine learning platform includes one or more deep neural networks) in order to predict the chronological age by calculating the phenotypical age of the subject; generating a report with the predicted chronological age and/or calculated phenotypical age of the subject; and providing the report to the subject.

The predicted chronological age, which is the determined phenotypical age, is also referred to as the biological age. The predicted chronological age can be compared to the actual chronological age, and the difference thereof can be used to determine the health of the patient. The lower a phenotypical age compared to the real chronological age, the more likely the subject is healthy. Greater differences between the phenotypical age and the real chronological age can be used to determine disease states.

In some embodiments, the processing of the taxonomic profile of the microbiota results in defining one or more of the following: an absolute amount of the microorganisms; an absolute amount of each microorganism; an absolute amount genus level taxonomic profile for each genus of the microorganisms; an absolute amount species level taxonomic profile for each species of the microorganisms; an absolute amount strain level taxonomic profile for each strain of the microorganisms; an absolute amount taxon specific gene count for microorganisms of the taxon; ecological group absolute amount; a relative amount of the microorganisms of total microorganisms in the microbiota; a relative amount of each microorganism; a relative amount genus level taxonomic profile for each genus of the microorganisms; a relative amount species level taxonomic profile for each species of the microorganisms; a relative amount strain level taxonomic profile for each strain of the microorganisms; a relative amount taxon specific gene count for microorganisms of the taxon; ecological group a relative; or combinations thereof.

In some embodiments, methods can include generating one or more of: a strain level taxonomic profile of the microbiota of the subject based on the amount of each of the microorganisms; a species level taxonomic profile of the microbiota of the subject based on the amount of each of the microorganisms; or a genus level taxonomic profile of the microbiota of the subject based on the amount of each of the microorganisms.

In some embodiments, each taxonomic profile is based on at least one of 16S variable regions or on whole metagenome reads.

In some embodiments, methods can include: accessing a database with a plurality of reference microorganism taxonomic profiles linked to chronological age and/or phenotypic age of a plurality of reference subjects; comparing the taxonomic profile of the microbiota of the subject with the plurality of reference microorganism taxonomic profiles; and grouping one or more microorganisms associated with a predicted phenotypic age range.

In some embodiments, methods can include: determining an altered taxonomic profile to reduce the predicted phenotypic age of the subject into a younger predicted phenotypic age range than the predicted phenotypic age of the subject; and including the altered taxonomic profile in the report provided to the subject.

In some embodiments, methods can include: determining a treatment method for obtaining the altered taxonomic profile of the subject to obtain a younger predicted phenotypic age range in the subject; implementing the treatment method with the subject; and obtaining the younger predicted phenotypic age range in the subject.

In some embodiments, the plurality of reference microorganism taxonomic profiles that are linked to chronological age and/or phenotypic age of the plurality of reference subjects are correlated with personal data of the reference subjects. As such, the method can include: obtaining personal data for the subject; associating the personal data of the subject with the generated taxonomic profile of the subject and/or predicted phenotypical age of the subject; and determining a correlation of the predicted phenotypical age of the subject with the personal data of the subject in view of the plurality of reference microorganism taxonomic profiles that are linked to the chronological age and/or phenotypic age of the plurality of reference subjects that is correlated with personal data of the reference subjects.

In some embodiments, methods can include: determining at least one microorganism whose change in amount provides an altered taxonomic profile to reduce the predicted phenotypic age of the subject into a younger predicted phenotypic age range than the predicted phenotypic age of the subject; changing the amount of the determined at least one microorganism in the microbiota of the subject; and obtaining the younger predicted phenotypic age range in the subject.

In some embodiments, methods can include: accessing a database with a plurality of reference microorganism taxonomic profiles linked to a plurality of diseases and/or disorders of a plurality of reference subjects; comparing the taxonomic profile of the microbiota of the subject with the plurality of reference microorganism taxonomic profiles; determining a risk of the subject developing one or more of the plurality of diseases and/or disorders; and including the risk of the subject developing one or more of the plurality of diseases and/or disorders in the report.

In some embodiments, methods can include: determining a dietary plan for obtaining the altered taxonomic profile of the subject to obtain younger predicted phenotypic age range in the subject; and including the dietary plan in the report. In some aspects, methods can include: implementing the dietary plan with the subject; and obtaining the younger predicted phenotypic age range in the subject.

In some embodiments, methods can include: determining a therapeutic treatment composition having one or more of the microorganisms for obtaining the altered taxonomic profile of the subject to obtain younger predicted phenotypic age range in the subject; and identifying the therapeutic treatment composition in the report. In some aspects, methods can include: implementing the therapeutic treatment composition with the subject; and obtaining the younger predicted phenotypic age range in the subject.

In some embodiments, a method of generating a reference database, which can be used in any of the methods, can be provided, which can include: isolating a plurality of microorganism nucleic acids of microorganisms from each of a plurality of reference samples, each reference sample being from a microbiota of a reference subject; analyzing the plurality of microorganism nucleic acids to determine an amount of the microorganisms of the microbiota of each reference subject based on the plurality of microorganism nucleic acids; generating a taxonomic profile of the microbiota of each reference subject based on the amount of each of the microorganisms; processing the taxonomic profile of the microbiota of each reference subject with a computer configured with a machine learning platform in order to predict the phenotypical age of each reference subject; and generating a reference database with the predicted phenotypical age associated with the taxonomic profile of the microbiota for each reference subject.

In some embodiments, methods can include: analyzing a plurality of reference microorganism taxonomic profiles linked to chronological age and/or phenotypic age of a plurality of reference subjects; and determining one or more common microorganisms in the plurality of reference microorganism taxonomic profiles that are associated with older predicted phenotypic age of a plurality of reference subjects and/or determining one or more common microorganisms in the plurality of reference microorganism taxonomic profiles that are associated with younger predicted phenotypic age of a plurality of reference subjects.

In some embodiments, methods can include: determining at least one altered taxonomic profile to reduce the predicted phenotypic age of the reference subjects to a younger predicted phenotypic age range than the phenotypic age of the reference subjects; including the at least one altered taxonomic profile in the report; and providing the report to plurality of reference subjects.

In some embodiments, methods can include: identifying at least one specific microorganism that modulates the phenotypic age of the reference subjects; creating a modulating composition for modulating the identified at least one specific microorganism in a microbiota; and providing the modulating composition to at least the subject.

In some embodiments, methods can include generating a reference database with a predicted phenotypical age associated with a taxonomic profile of a microbiota for a plurality of reference subjects.

In some embodiments, methods can include: analyzing a plurality of microorganism taxonomic profiles from a plurality of subjects in view of predicted phenotypical age associated with the taxonomic profile of the microbiota for of the plurality of subjects; determining at least one common microorganism that effects the predicted phenotypical age; determining at least one microflora alteration to alter at least one first microorganism taxonomic profile for at least one first subject to obtain a younger predicted phenotypical age; and optionally providing the determined at least one microflora alteration in a first report to the at least one first subject.

In some embodiments, methods can include generating a database with the plurality of microorganism taxonomic profiles associated with the predicted phenotypical age associated with the taxonomic profile of the microbiota for of the plurality of subjects.

In some embodiments, methods can include: creating a microflora intervention to obtain the at least one microflora alteration to alter the first microorganism taxonomic profile for at least the first subject to obtain the younger predicted phenotypical age; and providing the microflora intervention to at least the first subject. In some aspects, methods can include: designing a consumer good to have the microflora intervention; and delivering the consumer good to at least one consumer. In some aspects, methods can include: designing a dietary product to have the microflora intervention; and delivering the dietary product to at least one consumer. In some aspects, methods can include: designing a medical product to have the microflora intervention; and delivering the medical product to at least one consumer. In some aspects, methods can include: designing a clothing item to have the microflora intervention; and delivering the clothing item to at least one consumer. In the methods, the provided article can be utilized by the subject in order to decrease the predicted phenotypical age associated of the subject.

In some embodiments, methods can include: generating a computer program product stored on a tangible, non-transitory memory device of a computer that when executed cause the computer to: access a database in accordance with an embodiment described herein; compare the subjects taxonomic profile with the database; provide information on at least one specific microorganism that modulates the predicted phenotypical age associated of the subject; generate the report with the provided information; and cause the report to be provided to the subject. In some aspects, the database is configured as a blockchain storage system that is capable of tracking changes of the taxonomic profile of the subject and/or plurality of subjects and tracking changes of the predicted phenotypical age of the subject or plurality of subjects.

In some embodiments, a method of generating insurance policies can include: accessing an insurance profile database with a plurality of microorganism taxonomic profiles associated with a predicted phenotypical age associated with each taxonomic profile of microbiota for a plurality of subjects; obtaining information for an insurance customer; comparing the information of the insurance customer with the insurance profile database; generating an insurance policy based on the comparison of the information of the insurance customer with the insurance profile database; and delivering the insurance policy to the insurance customer. In some aspects, methods can include: obtaining a predicted phenotypical age of the insurance customer that is generated from a microorganism taxonomic profile of the insurance customer; determining a payment rate for the insurance policy based on the predicted phenotypical age of the insurance customer; and including the payment rate in the insurance policy. In some aspects, the predicted phenotypical age of the insurance customer that is generated from a microorganism taxonomic profile of the insurance customer is obtained by: isolating a plurality of microorganism nucleic acids of microorganisms from a sample of a microbiota of the insurance customer; analyzing the plurality of microorganism nucleic acids to determine an amount of the microorganism of the microbiota based on the plurality of microorganism nucleic acids; generating a taxonomic profile of the microbiota of the insurance customer based on the amount of each of the microorganism; processing the taxonomic profile of the microbiota with a computer configured with a machine learning platform in order to predict the phenotypical age of the insurance customer; generating a report with the predicted phenotypical age of the insurance customer; and providing the report to an insurance provider that administers the insurance policy. In some aspects, the microorganism are those described herein.

In some embodiments, an insurance profile database is obtained by: analyzing a plurality of microorganism taxonomic profiles from a plurality of subjects in view of predicted phenotypical age associated with the taxonomic profile of the microbiota for of the plurality of subjects; determining at least one common microorganism that effects the predicted phenotypical age; determining at least one microflora alteration to alter at least one first microorganism taxonomic profile for at least one first subject to obtain a younger predicted phenotypical age; and storing the determined at least one microflora alteration in the insurance profile database.

In some embodiments, a method of deriving microbiological biomarkers of aging can include: creating a machine learning model trained to predict the age of a host of microbiological sample using its taxonomic profile; and selecting a subset of microbiological features based on their Accumulated Local Effect (ALE) function behavior (monotonicity and range).

In some embodiments, any of the methods herein can be performed using biomarkers of the microorganisms. The methods may include using the biomarkers of a specific group defined herein, such that the Group includes all members of the defined group. In some aspects, the biomarkers and microorganisms include a set thereof, which is any group or set thereof recited in the application or incorporated applications.

Some embodiments of this invention allow people (e.g., subjects) to track the state of their gut microbiota via a web-based application. Here, the subject can provide a biological sample or the biological data (e.g., nucleic acids, proteins, chemicals, etc.) obtained from an analysis of the biological sample. The web-based application can then provide the reports, data, and analytics described herein to the subject, such as providing the information to a computer (e.g., laptop, tablet, smartphone, handheld) of the subject. The information can be the same information identified to be in the reports, and can include: the predicted biological age compared to the chronological age of the subject for based on one or more individual samples from that subject; interactive charts, selections for picking a defined age range; information for a defined age range; the quality or statistics of the predicted biological age (e.g., MAE, RMSE $R^2$, Pearson's R, etc.); identification of the number and/or types of microbes used in determining the predicted biological age; the smallest diversity coverage by the model; the maximum diversity coverage by model; comparisons of any data or results between different samples; a chronological comparison of the predicted biological age and other data or results across a plurality of samples; information about microbial lookalikes that have similar gut microbiota, with identity anonymity for the individuals that are microbial lookalikes; nutritional advice to change the predicted biological age; identity of probiotics to consume to change the predicted biological age; identify of probiotics to not consume to change the predicted biological age; or other information.

The process by the web-based application can also include information about seno-positive and seno-negative features. This can include seno-positive and seno-negative features being aggregated into other statistics to reduce the dimensionality even further. For example, all seno-negative or seno-negative features can be replaced by their weighted average abundance with the weight representing their correlation with chronological age, ALE amplitude, ALE rate of change or other values. This results in the initial 41 features of Group 41 (or other number of other Groups) collapsing into 2 dimensions which can be plotted in a web-interface. The user may observe the graph or provide it to a medical professional to establish the overall condition of their gut flora. The interface of the application or the professional may then provide nutritional advice or medication to reduce the number of seno-positive (associated with older age) microbes or increase the number of seno-negative (associated with younger age) microbes.

In some embodiments, the biological sample from the subject is a stool sample that includes the microbiota. As such, the method can include a subject ordering at least one stool sample collection container. The subject can then place a stool sample in the collection container. The stool-containing collection container can then be sent for analysis of the nucleic acids of the microorganisms of the sample of microbiota from the subject. The entity of the web-based application may process the stool sample(s) or the stool samples may be sent to a dedicated stool sample facility. At some point in the process regardless of the entity that processes the stool sample, the nucleic acids of the microorganisms of the microbiota are analyzed. The method steps of the analysis include the generation of the microbiota taxonomic profile, processing the taxonomic profile with a machine learning platform to obtain the predicted biological age of the subject, and to generate and provide the report, such as displaying the report on the subject's computing device.

FIG. 22 illustrates an example of an application that can perform the methods described herein. Here, the example includes the application being able to receive or provide the already known amount of the individual microbes in the microbiota, or receive or provide the already known taxonomic profile of the microbiota of the subject. In any event, the processing of the taxonomic profile is performed so that the biological age (e.g., phenotypical age) of the subject is obtained or predicted. As a result, the application provides displayed information in a report to the subject. The report can include a graph that shows the score of the subject (e.g., your score) compared to other subjects. The graph may be interactive and allow the subject to adjust estimate parameters, such as the KDE for a defined percentage of the population. The report may also include charts or tables regarding the results of the biological clock model. The report may also include the identity of certain microbes or the biomarker for the microbes. The information may be presented so that the subject can see the microbes or biomarkers that can be reduced that can result in decreasing the predicted biological age, and selection of a certain microbe or biomarker can provide information on how to decrease the microbe in the gut. The information may be presented so that the subject can see the microbes or biomarkers that can be increased that can result in decreasing the predicted biological age, and selection of a certain microbe or biomarker can provide information on how to increase the microbe in the gut. In the example of FIG. 22, the biomarker 6 was selected (e.g., by clicking or hovering over selection icon), where the information to increase the presence of biomarker 6 includes: adjusting diet in a specific way; avoid exposure to specific type of radiation; avoid exposure to specific types of compounds; and exercise a specific skill (e.g., athletic activity, running, weight lifting, yoga, stretching, etc.).

In some embodiments, a subscription-based service may be provided to the subject. The subscription can allow for the processing of multiple samples and the identification of multiple biological ages based on the sequence of the multiple samples. This can allow tracking of the final scores of each sample. The trends in the samples and changes thereof can be analyzed to determine programs that may be able to reduce a high predicted biological age. The application can then provide the end user with tips on interventions that can shift the biological age results to a lower predicted age, which likely can increase the health of the subject.

In an example, the information on all identified biomarkers is compressed into 2 dimensions via the following procedure:

$$\text{Age score} = \frac{\sum w_i * X_i}{\sum w_i}$$

$$\text{Youth score} = \frac{\sum w_j * Y_j}{\sum w_j}$$

Here, "X" is the normalized (e.g. by substituting abundances with population percentiles within 0-100% range) abundance vector of seno-positive features, "w" is the vector of weights (e.g. ALE plot numerical derivative, exact ALE value or other statistic), "Y" is the normalized abundance vector of seno-negative features. The two new values can be calculated for a selected population (e.g., healthy individuals of the same age) to provide a kernel density estimation (KDE) plot to illustrate the score distribution and give the end user a frame of reference. KDE regions may be adjusted to contain a specific portion of the selected population (e.g. 90% or 50%).

In some embodiments, a method of creating a microbiomic aging clock for a subject, the method comprising: (a) receiving a microbe abundance signature of a microbes of a microbiota of the subject; (b) creating input vectors based on the microbe abundance signature; (c) inputting the input vectors into a machine learning platform; (d) generating a predicted microbiomic aging clock of the microbiota of the subject based on the input vectors by the machine learning platform, wherein the microbiota aging clock is specific to the microbiota; and (e) preparing a report that includes the microbiomic aging clock that identifies a predicted biological age of the subject. In some aspects, the method can include, after a defined time period: performing steps (a), (b), (c), (d), and (e) in a second iteration; and comparing the initial report with the report of the second iteration; and determining a change in the predicted biological age over the defined time period.

In some embodiments, the method can include: creating at least a second microbiomic aging clock by repeating any one or more of steps (a), (b), (c), and/or (d), wherein the second microbiomic aging clock is based on a second microbe abundance signature from the microbiota of the subject, a different microbiota of the subject, or a microbiota of a second subject; and optionally, preparing a report that includes the second microbiomic aging clock that identifies a second predicted biological age of the subject, a different tissue or organ of the subject, or a tissue or organ of a second subject. In some aspects, the method can include combining the microbiomic aging cock with the second microbiomic aging clock to create a synthetic microbiomic aging clock, wherein the synthetic microbiomic aging clock provides a synthetic biological age of the subject; and optionally, preparing a report that includes the synthetic microbiomic aging clock that identifies the synthetic biological age of the subject. In some aspects, the method can include: comparing the predicted biological age of the tissue or organ with the actual age of the subject; comparing the second predicted biological age of the tissue or organ with the actual age of the subject; comparing the synthetic biological age of the tissue or organ and with the actual age of the subject, wherein the method further comprises: preparing a report with the comparing and with a difference from the actual age of the subject.

In some embodiments, the report includes one or more of: a therapeutic regimen based on the predicted biological age in view of an actual age of the subject; a diet regimen based on the predicted biological age in view of an actual age of the subject; a questionnaire about lifestyle habits; a prognosis of the life expectancy with and/or without the therapeutic regimen; a prognosis of the life expectancy with and/or without the diet regimen; a prognosis of the probability of survival of patient during the therapeutic regimen; or a prognosis of the probability of survival of patient during the diet regimen. In some aspects, the method includes: comparing the initial report with the report of a second iteration; determining a change in the predicted biological age over the defined time period; and determining: whether the therapeutic regimen changed the predicted biological age, if the therapeutic regimen changed the predicted biological age, then determine whether or not to: continue therapeutic regimen, change therapeutic regimen, or stop therapeutic regimen, or if the therapeutic regimen does not change the predicted biological age, then determine whether or not to: continue therapeutic regimen, change therapeutic regimen, or stop therapeutic regimen.

In some embodiments, the report can include a therapeutic regimen based on the predicted biological age in view of an actual age of the subject, or a diet regimen based on the predicted biological age in view of an actual age of the subject.

In some embodiments, the method can include performing one or more of an actuarial assessment of the subject based on the predicted biological age; a risk assessment based the predicted biological age; or an insurance assessment based on the predicted biological age.

In some embodiments, a computer program product includes a tangible, non-transitory computer readable medium having a computer readable program code stored thereon, the code being executable by a processor to perform a method for biological aging clock for a patient, wherein the method includes the steps of one of the methods recited herein that are performed by the computer.

EXAMPLES

All the data used in the DFS example working embodiment was obtained from published studies (project IDs at SRA and ENA: ERP019502, ERP009422, SRP002163, ERP004605, ERP002469, ERP008729, ERP005534).

All these studies operate with similar sample preparation technique. Stool samples (approximately 50 g) are obtained from healthy donors and are stored at 4° C. or are frozen at −80° C. if case immediate DNA isolation is not possible, which prevents bacterial blooming.

DNA can be isolated using a variety of kits and methods to prepare it for WGS sequencing on either Illumina Genome Analyzer II or Illumina HiSeq 2000 platforms (Wesolowska-Andersen et al. 2014). Read processing and taxonomic profiling can be implemented. Downloaded sequencing files were not downsampled. Quality control included adaptor removal, quality trimming and quality filtering, human reads removal. Additionally 4-mer distribution entropy was assessed in order to verify that none of the samples had been too diluted. Reads were mapped in Centrifuge against a FM index of bacterial and archaeal genomes previously released. The relative abundance table for each sample was filtered to contain only reliably detected microbes (>1e-5 relative abundance).

The present study adapted several machine learning approaches for age prediction. The objective of machine learning problem is a classical supervised regression. Models were trained on bacterial taxon features as input variables.

Data for training machine learning algorithms were modified to contain only reliably detected features (>1e-5 abundance). The size of the data after removing non-existent or missing age values is 3'058 records from 621 people. Each record contains 1'673 bacteria features. The target variable consists of ages in a range of 7 and 90 years old. The age distribution is depicted in FIG. 12.

Models were trained with five-fold cross validation and grid/random search strategies to compensate for overfitting. Due to the considerably moderate size of the dataset no outer test set was introduced. Instead, given metrics obtained as prediction of 5 test sets corresponding to each fold, thus resulting in the fully predicted input dataset. All models were evaluated with the same fold-splitting for the fair comparison.

All methods demonstrated relatively good correlation of predicted age with actual chronological age, but both gradient boosting machine and DFS outperformed other models. The best configuration of the DFS model had 3 layers with 512 neurons in each, PReLU activation function and learning rate of 0.001. The best gradient boosting configuration has maximum depth of a tree of 6, learning rate of 0.1, maximum delta step of 2, L2 regularization term of 0 and L1 regularization term of 0.5. The results metric presented in Table 5, which provides the CV results of XGB and DFS models.

TABLE 5

| Model | MAE | RMSE | $R^2$ | Pearson |
|---|---|---|---|---|
| XGB | 3.81 | 5.63 | 0.90 | 0.95 |
| DFS | 2.83 | 5.00 | 0.92 | 0.96 |

Method of Constructing Microbiomic Aging Clock

Figure 24:
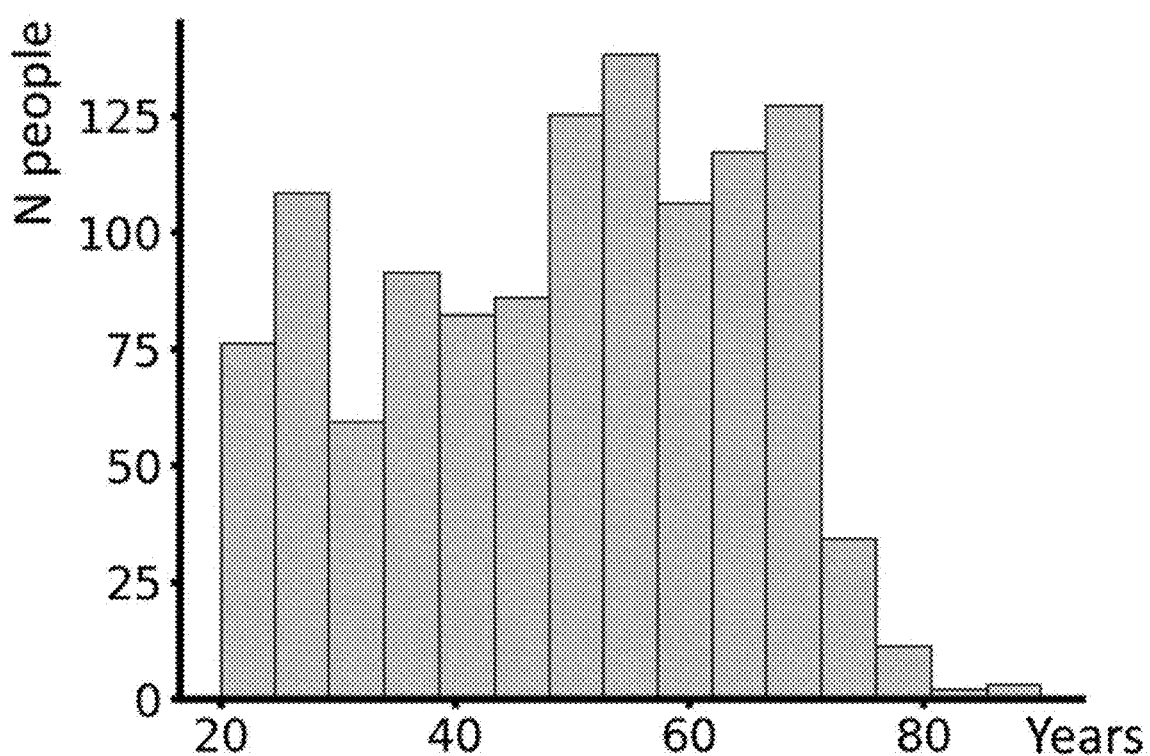
FIG. 24 includes a graph showing the age distribution for the sample used in "Model 2" training (N=1165 donors).

A method 1400 of constructing a microbiomic aging clock is provided, as described by the following steps and shown in FIG. 14. The method includes obtaining nucleic acid information contained within the guts of a cohort of subjects (block 1402). This can be done by obtaining the nucleic acids from a biological sample of each subject and performing the assays to get the information, or the information may be obtained elsewhere and the nucleic acid information is provided for this method. All the subject should have a definite chronological age (CA). Age distribution within the cohort will affect the resulting clock biases, and thus uniform distribution is preferable. The cohort should contain the subjects belonging to the age range of the intended use, such as using a clock trained on the cohort of young people will produce reliable predictions for young people but unreliable predictions for the elderly. In the implementation, data from publicly available studies was used, their ENA identifiers are: ERP002061, ERP008729, SRP002163, ERP004605, ERP003612, ERP002469, ERP019502, SRP008047, ERP009422, ERP005534, PRJEB2054, PRJNA375935, and PRJNA289586. The data included 1165 people within 20-90 year old age range with no health conditions specified in the accompanying study metadata obtained from ENA or publication supplementary information. FIG. 24 shows the age distribution for the 1165 people in Model 2.

The method 1400 can include filtering the obtained nucleic acid information (block 1404). In some aspects, all WGS reads were truncated based on the end bases' quality score (cutoff: 50 phred score) and all reads with average quality <20 phred score were removed completely. Additionally, all reads originating from the human genome were removed using Bowtie2 alignment tool against hg19 index.

The method 1400 can include inferring microbe abundance profiles from nucleic acid information (block 1406). In some aspects, a Centrifuge classifier can be used for metagenomic sequences with Bacteria, Archaea index. Centrifuge individual output files were aggregated into one sparse table containing the microbe species relative abundance profiles of all subjects in the cohort. Relative abundance profiles can be obtained via other software products (e.g. Metaphlan2) or by normalizing absolute abundance profiles.

The method 1400 can include filtering and normalizing raw abundance profiles (step 1408). Each microbial taxon in the relative abundance table is hereupon treated as a mathematical feature. To reduce the chance of subsequent model overfitting, the protocol includes reducing the dimensionality and leave only the most relevant features. There are multiple feature selections methods that can be used for this task. In some aspects, this can include use of a straightforward and simple approach of assigning zero values to all abundances <1e-5, justifying that as removing unreliably detected microorganisms. Then, the protocol removed all features that were present in <0.0013 of samples. This led to not one sample losing >5% of its community. Then all values were divided by the sum of abundances in their respective samples.

The method 1400 can include defining cross-validation (CV) sets of data (block 1410). The data was separated in 10 folds stratified by the study of origin of that data in order to reduce the possible influence of any particular study's data bias. All folds remained fixed during the training stage. The separated data can then be used as a defined data set, and then processed through the model to validate the model. The different data sets can be used for validation.

The method 1400 can include training neural network models (block 1412). A number of neural network architectures can be picked by a professional and then trained with various parameter configurations. Neural network training was carried out using Python3 public libraries Keras and TensorFlow. All the possible configurations are tried using grid search approach. Since at this stage CV is used, each parameter and architecture configuration was is used to produce as many models as there are folds. In this training, each configuration produced 10 models trained on different slices of the original data. Training continues for 2500 epochs.

The method 1400 can include assessing model performance (block 1414). Each parameter configuration in this case produced 10 models. Each one of them was used to predict their respective testing sets, as defined at the CV fold definition stage. The overall quality of the configuration was assessed using mean absolute error (MAE) across all folds. Other metrics, such as $R^2$, Pearson's R, mean square error or median absolute error can be used as well. The best configuration obtained in CV was: 3×1024 nodes, ReLU activation function, Adam optimizer, dropout fraction 0.5 at each layer, and 0.001 learning rate. This is from Model 2.

The method 1400 can include generating a model ensemble of a group of models that have low error (block 1416). The models that show the smallest error are combined into one ensemble, which is then used with a previously untouched verification data set. The ensemble models' individual predictions were then averaged by either taking their mean prediction value. Other methods of aggregating can also be valid, e.g. taking the median value or performing aggregation after removing outlier predictions or picking the midpoint of the prediction range. The final model error was reported as the MAE achieved by the best configuration—5.91 years. This is from Model 2.

Assessing Probiotic Effect on Host Condition

The biological clock model described herein can be used to assess the effect of a probiotic on a condition of a host. This can include assuming that administering a probiotic changes only the probiotic's abundance. As such, it is easy to check how a particular microbe affects intestinal age, using the model. The gerontological potential of 16 commercially available probiotic bacteria was assessed by Model 2 with the following: Bacillus coagulans, Bifidobacterium animalis, Bifidobacterium bifidum, Bifidobacterium breve, Bifidobacterium longum, Enterococcus faecium, Lactobacillus acidophilus, Lactobacillus casei, Lactobacillus gasseri, Lactobacillus helveticus, Lactobacillus plantarum, Lactobacillus reuteri, Lactobacillus rhamnosus, Lactobacillus salivarius, Propionibacterium freudenreichii, Streptococcus thermophilus. However, using the described method it is possible to check the effect of any other microbe, whose abundance belongs to the model input. In some aspects, the microorganisms of this paragraph are a specific group, and are used as a specific combination, herein "Group 16," as defined above, which designates the 16 specific members in the group. Accordingly, each of the 16 different types of recited microorganisms is present in Group 16.

To illustrate how these probiotics affect age prediction on an individual level, the protocol increased their abundance by 1% in seven relative abundance profiles and calculated the changes in the predicted age. Other methods of numerical differentiation could also be applied. Using the model, it is impossible to estimate the efficiency of probiotic implantation, and thus the absolute values of the predicted age change are not as important as the sign of the change. The sign of the age change, however, can be used to predict the ability of a probiotic to cause geroprotective effect. FIG. 15 shows the simulated effect of increasing 16 probiotic bacteria in microflora profiles, where the dark grey is the predicted age increases, light grey is the predicted age decreases, and white is the predicted age does not change.

From the example of FIG. 15 it is seen that different people can have both positive and negative effects on the predicted age from the same bacterium by using the biological clock model. To see how a bacterium affects intestinal age on a population level it is suggested to use accumulated local effects (ALE). The methods of calculating the ALE are provided herein.

The data shows that some of the microbes used in the model identified as seno-negative within the >50 years old group. Increasing some of them has an almost linear effect, while others affect age prediction only in the higher end of their abundance distribution, and certain ones may have a non-monotonic effect on a population. The results shown in the table of FIG. 16A and FIG. 16B are obtained from processing the publicly available ENA entries, and provide proof of concept.

Figure 16B:
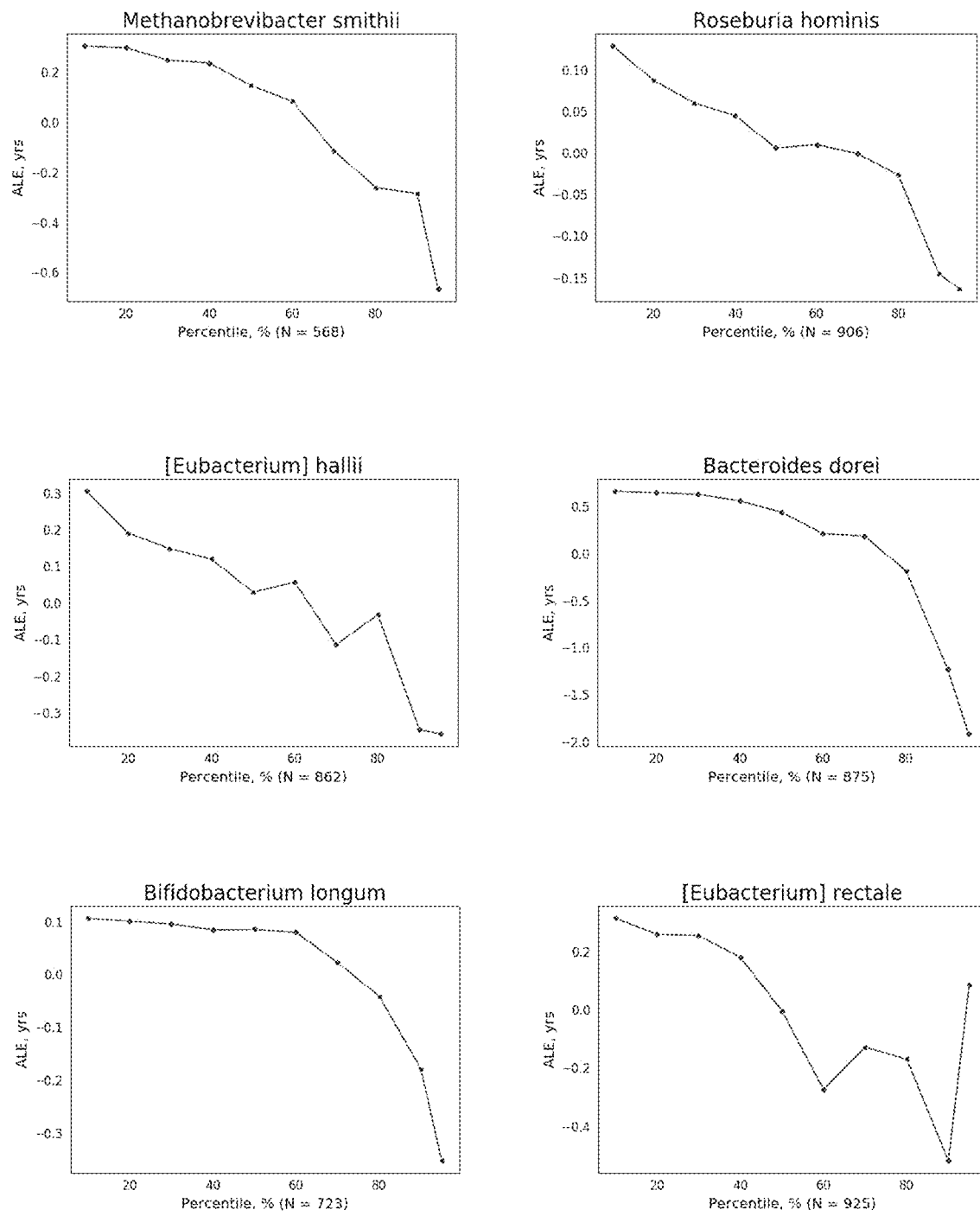
FIG. 16B shows the effect of 6 microbes on a sample of people older than 50 years old.

The data in FIG. 16B shows the effect of 6 microbes on a sample of people older than 50 years old. The change in ALE between two points on X axis indicates the average change in the predicted age while shifting a microbe's abundance. Only people with non-zero microbe abundances were considered in each particular case.

The data in FIG. 16A shows average changes in the predicted while shifting microbes' abundance within the subsample of people older than 50 years old. Only people with non-zero microbe abundances were considered in each particular case.

Predicting Risk of Disease and Morbidity

The biological clock model can also be used to assess intestinal age for use in a morbidity prediction. This can also be used to predict the risk of obesity. For example, the body mass index (BMI) can be predicted by using the biological clock model along with microbiomic information.

In some embodiments, the biological clock model can be used for predicting the BMI. The intestinal age predicted by the biological clock model can be used alongside microbiomic information to predict a person's BMI, as substitute obesity risk metrics. Using information on 314 prevalent microbial species' abundances (as defined in the Centrifuge index) and the predicted intestinal age the model managed to estimate hosts' BMI better than baseline median assignment. The specific microbes are:

The sample that was used to train and verify the BMI predictor contained 968 microbiomic profiles with known BMI and the age prediction error <10 years. An example of 30 of these profiles are provided in FIG. 23, which shows the profile ID, actual BMI, Predicted BMI, Predicted Phenotypic Age, and the actual Chronological Age. These profiles were also used in the aging clocks' training, their predicted age is that determined during the CV stage. These profiles were obtained from samples deposited in ENA. The specific version of the Centrifuge index is "Bacteria, Archaea from last updated Apr. 15, 2018."

Median BMI assignment yields the MAE of 4.129 kg/m$^2$, while the biological clock models have the MAE of 3.642±0.208 kg/m2, as estimated across five folds. The BMI estimator is realized as a gradient boosting regressor, created with XGBoost 0.90 Python 3.7.3 library. The exact parameters used during training are: {alpha:0, eta:0.1, eval_metric: mae, gamma:0.0, lambda:0.5, max_delta_step:0.0 max_depth:6, tree_method:gpu_hist}, which is provided as an example. However, variations of this may also be used.

Figure 17:
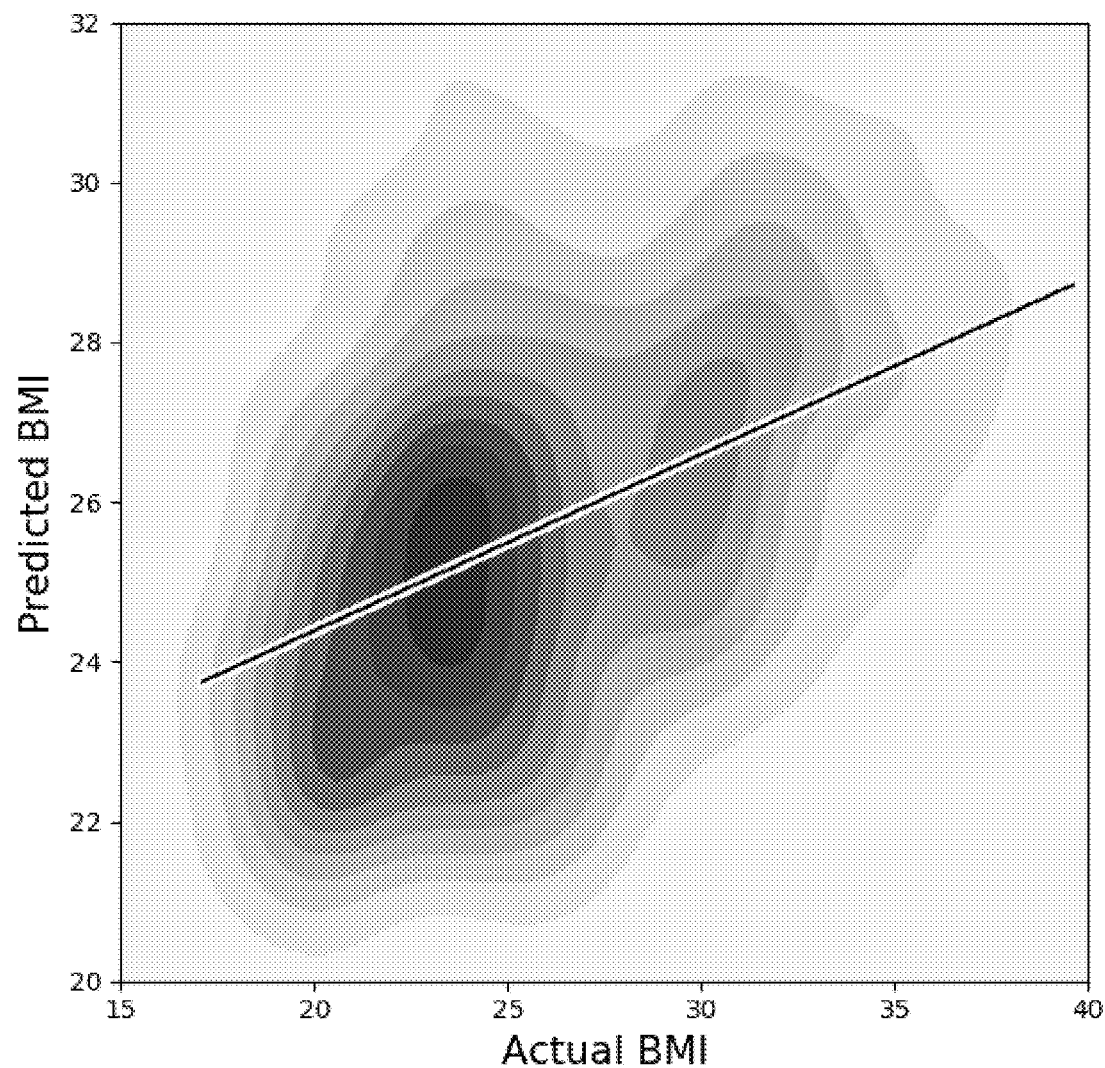
FIG. 17 shows a kernel density estimation (KDE) chart of BMI predictions.

FIG. 17 shows a kernel density estimation (KDE) chart of BMI predictions obtained with an XGBoost model for 968 relative abundance profiles with accompanying intestinal age information The line indicates the ordinary least squares regression for the observations, its equation is (Predicted BMI)=0.215×(Actual BMI)+20.16.

In some embodiments, the biological clock can be used in methods for predicting risk of developing Type I Diabetes (T1D), which can use Model 2. While verifying the intestinal age predictor containing 1606 features, the protocol was modified to include profiles obtained from people with T1D in the verification set. According to the clock model trained with T1D data, people with T1D are more likely to be predicted older than they actually are, where the average error is +14.75 years. For comparison, average prediction error for profiles from healthy hosts in this study (PRJNA289586) is +0.41. Meanwhile MAE for T1D hosts is 18.02 years and for healthy hosts is 8.40 years. Thus, the error distribution for diabetic people is skewed towards highly positive numbers, which could be used as an indication of their health condition, and thereby be used as a biomarker of diabetes.

Figure 18:
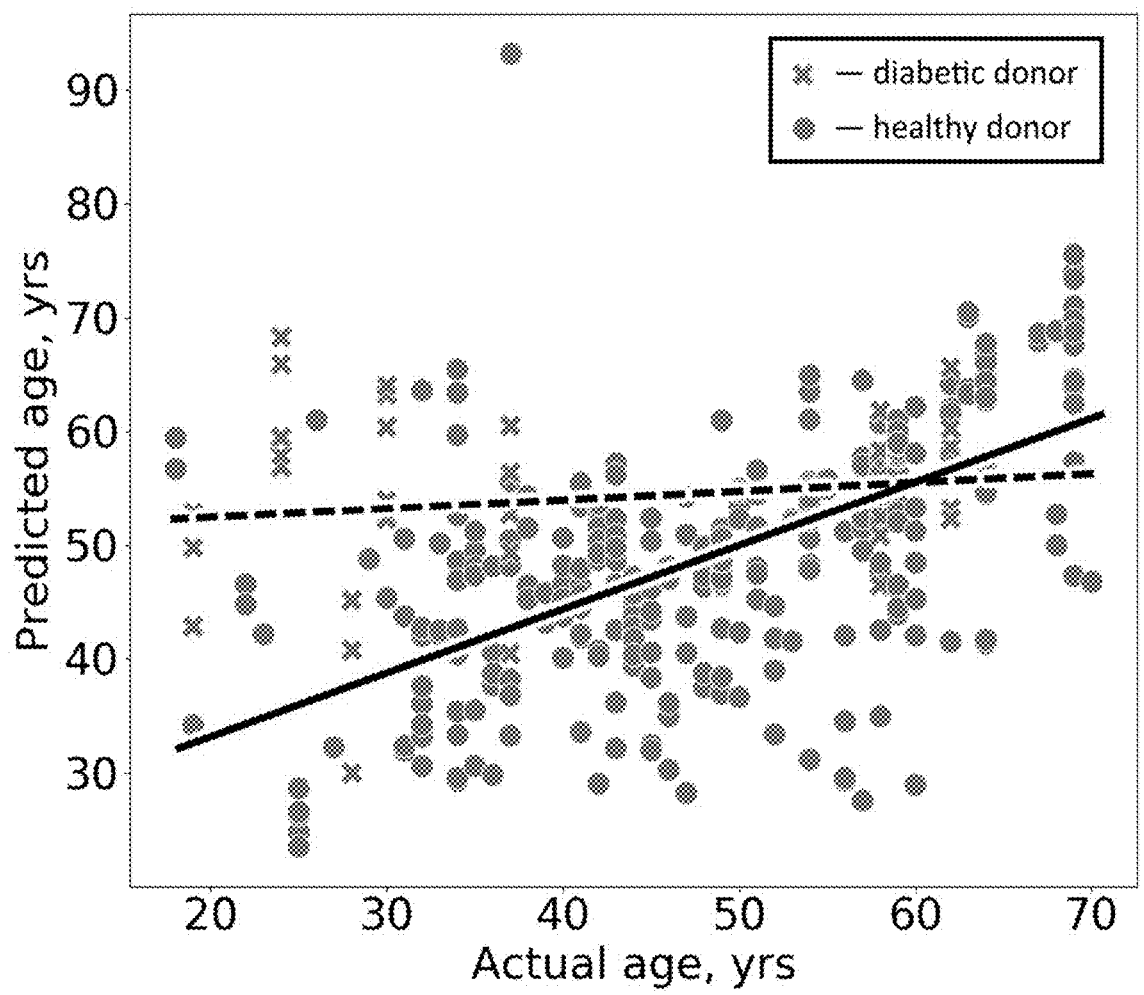
FIG. 18 shows the model performance in an independent set of samples obtained from public studies deposited at ENA servers.

FIG. 18 shows the Model 2 performance in an independent set of 436 samples obtained from public studies deposited at ENA servers (ERP000108, PRJNA375935, PRJNA289586), the latter of which contains 34 samples from donors with Type-1 Diabetes. Median age assignment provides a baseline of 9.27 years mean absolute error (MAE), while our model shows MAE of 5.91 years (R2 score=0.81). Meanwhile, the model fails to accurately predict the age for people with diabetes (R2 score=−0.73, MAE=18.02 years, Baseline=13.65 years) and assigns young diabetic donors higher than actual age. This indicates that the model qualifies as an accurate aging clock in healthy individuals and responds to diseases as age-affecting conditions. FIG. 18 includes a verification set ($N_{Total}$=323, $N_{T1D}$=34) for age prediction with the model containing 1606 features. The dashed line is the OLS regression of diabetic profiles, solid line is OLS regression of healthy profiles. The diabetic hosts typically are predicted older than the healthy ones.

Biological Aging Clock Model

The following example provides a method to reduce the dimensionality of high-throughput biological data and rank the features according to the magnitude of their effect on aging process. The method can include two as illustrated in FIG. 19: (1) training a reliable aging clock model, and (2) applying accumulated local effect (ALE) to the model to measure its responses to changes in feature values. The initial aging clock can be trained on any biologically relevant data with the sole limitation of it being of finite predetermined dimensionality (e.g. a vector of microbe relative abundances). The model in essence can represent any method of machine learning, including deep neural networks (DNN) used in the described example.

In this example, a DNN model is trained to predict a person's age from their gut microbiota relative abundance profiles. The DNN model consists of 3 hidden layers with 1024 nodes in each, trained using PReLU activation function, dropout rate of 0.5 and 0.001 learning rate. Only the samples from people 20-90 years old have been used with only one sample per donor, for a total of 1,165 donors.

The model achieves mean absolute error of 5.91 years with baseline (median age assignment) producing 9.27 years error during independent data set verification. The age of people with Type-1 Diabetes is predicted older than actual and results in 18.02 year error with baseline being 13.65. Thus, the model accurately predicts age in healthy individuals and reacts by overestimating the age of people with disease.

The model is then subjected to accumulated local effect analysis (ALE) to see how the model reacts to slight changes in specific microbe abundances. If the model reacts by on average decreasing the predicted age when the microbe is simulated to be more abundant, then the microbe is assigned a seno-negative status. If the model produces higher predicted age with increased microbe abundance, its seno-status is seno-positive. For example ALE Equation 1 can be used to calculate the local effects (LE) for each quantile. To produce ALEs, LEs are summed as per ALE Equations 2).

Additionally, ALEs are centered, so that the sum of all ALEs for a feature is zero.

In this example, biomarkers of aging are selected based on ALE amplitude, such as the maximum shift in prediction that can be achieved by changing a feature value. Choosing only the features that have amplitude higher than 0.1 year produces the list of microbes in Group 41 defined herein. However, the other groups of microbes defined herein may be used.

To estimate the influence of a feature on model performance all samples from a set are separated into equal bins according to a selected feature distribution (in this case with 25% steps). Then for each bin predicted age is calculated on its left and right borders, the change in prediction between them is averaged to obtain local effects (LE). LE are further summed into accumulated local effects (ALE) to provide a continuous picture of a feature's influence. At the last step all ALEs are shifted so that the average ALE is zero. See FIG. 19.

Figure 20:
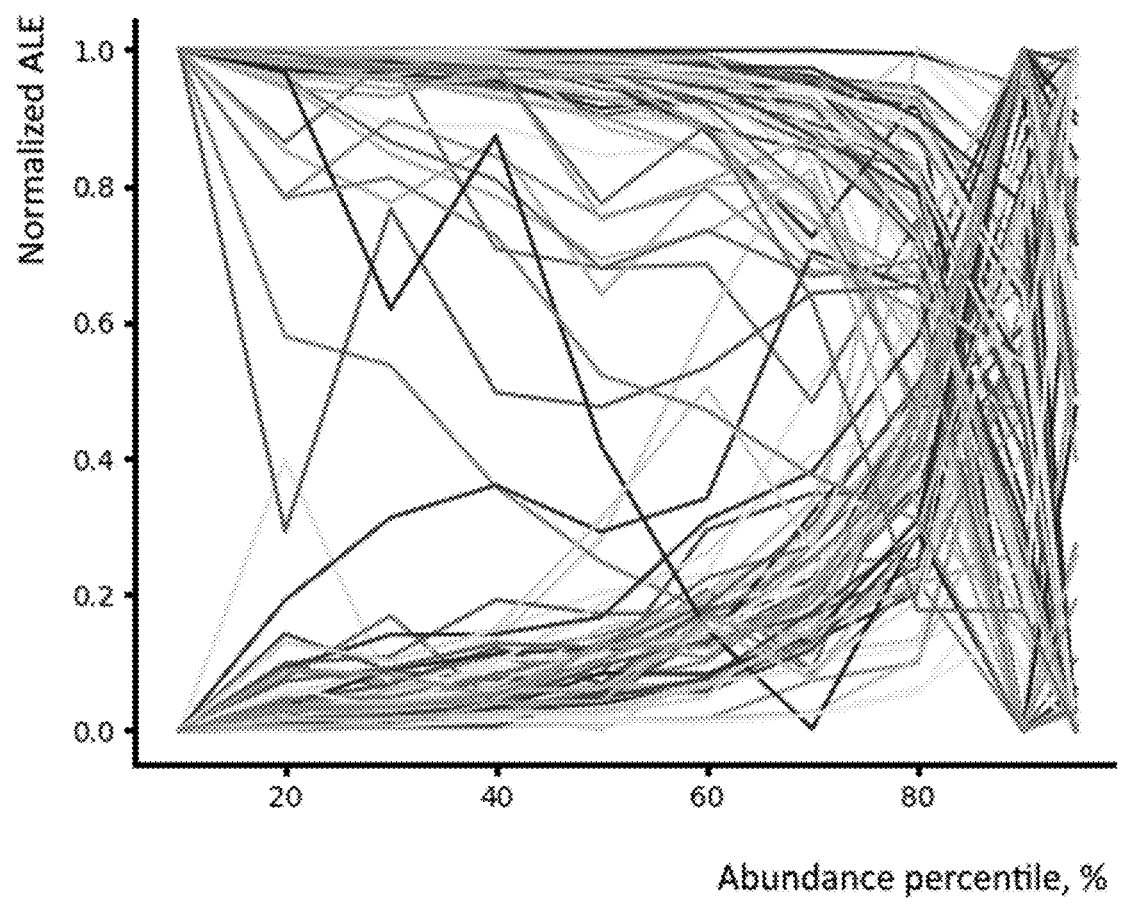
FIG. 20 provides examples of seno-positive and seno-negative behavior for the gut microflora aging clock.

Most features when subjected to ALE analysis display generally monotonic growth or decline. Those features that show increased predicted age with higher values (increasing ALE plot) are called seno-positive. On the other hand, features that show decreased predicted age with higher values (decreasing ALE plot) are called seno-negative. Some features do not produce monotonic ALE plots, but most are. FIG. 20 displays ALE plots of the features whose maxima and minima are located in the leftmost bin of feature distribution, i.e. seno-negative and seno-positive features. As such, FIG. 20 provides examples of seno-positive and seno-negative behavior for the gut microflora aging clock, as well as some non-monotonic features. ALE is normalized to lie within [0;1] region, actual amplitudes vary.

Definitions

"Artificial neural networks", also called "ANNs" or just "neural networks", are based on a large collection of connected simple units called artificial neurons loosely analogous to axons in a biological brain. If the combined incoming signals are strong enough, the neuron becomes activated and the signal travels to other neurons connected to it. The activation function of such neurons is often, though not always, represented as a sigmoid function.

"Deep learning" (DL) (also known as deep structured learning, hierarchical learning or deep machine learning) is the study of artificial neural networks that contain more than one hidden layer of neurons. Such a neural network is called a "deep neural network". A "convolutional neural network" is a type of neural network in which the connectivity pattern is inspired by the organization of the animal visual cortex.

"Deep Feature Selection" (DFS) is a machine learning method based on adding a sparse one-to-one linear layer between the input layer and the first hidden layer of the MLP.

"Mean Absolute Error" (MAE) is a quality metrics equal to the average absolute difference between predicted and observed ages.

"Permutation Feature Importance" (PFI) is a method of estimating feature importance in a machine learning model based on measuring the reduction in predictive power upon permuting specific features.

"Multi Layer Perceptron" (MLP) is a neural network model used for supervised learning consisting of more than 3 layers and used for distinguishing linearly inseparable data.

"Whole Genome Sequencing" (WGS) a number of sequencing methods that suggest fragmenting long DNA molecules prior to reading them. WGS methods' output is usually a file containing 105-106 short DNA sequences.

"XGBoost" (XGB) is an open source implementation of gradient boosting machine learning technique, which relies on iteratively combining weak prediction models.

"Human gut microbiome" is the aggregate of all microbial communities inhabiting human gut. Microbiota is the total sum of all organisms inhabiting human gut. "Gut microbiome sample" usually stands for "stool sample" in microbiology, however biopsy samples are also used.

"Taxonomic Profile" is a vector consisting of relative or absolute amounts, abundances or percentages for all microbes present in the community. All taxonomic profiles sum up to 1, or 100%. That is the amounts of different microbes are fractions that sum to 1, or up to 100%.

"Accumulated Local Effects" (ALE) is a method of visualizing importance of features in a model. ALE score in this patent is the average change in predicted age upon substituting a target taxon abundance with its lower and upper 5% quantile values.

"Metagenome" is an aggregate of all DNA information present in the community. Usually it is represented by a text file containing short sequences (reads of length 100-200 nucleotides) identified during sequencing.

"Binning" is the procedure of assigning each read from the sequencing output file to one or more taxon(s) or taxa.

"Phenotypical age" is an aggregate metrics of human health that reflects an individual's likelihood of developing age associated disorders and their organism performance compared to healthy individuals of all chronological ages.

"Pipeline" is a series of sequentially executed programs that take in raw data, carry out data formatting, filtering and normalization, perform calculations and generate an output, which can be a predictive model, a generative model, a data statistic or an estimated hidden variable.

Chronological age is the actual age of a subject or organism. For animals and humans, chronological age may be based on the age calculated from the moment of conception or based on the age calculated from the time and date of birth. The chronological age of the cell, tissue or organ may be determined from the chronological age of the subject or organism from which the cell, tissue or organ is obtained, plus the duration of the cell, tissue or organ is placed in culture. Alternatively, in the case of the cell or tissue culture, the chronological age may be related to the total or accumulative time in culture or passage number.

Phenotypic age may or may not be the actual age of a subject or organism, but phenotypic age is the age that the body or organ appears to be biologically. While a subject may actually be 40, their biology may have a phenotypic age much higher or lower than 40. The phenotypic age can include the set of observable characteristics of an individual resulting from the interaction of its genotype with the environment. Phenotypic age is related to the physiological health of the individual, and biomarkers thereof. Phenotypic age is associated with how well organs and regulatory systems of the body are performing and at what extent the general homeostasis at all levels of the organism is being maintained, as such functions generally decline with time and age.

Biological age is defined as a score illustrative of an individual's health issues risk. In aging clocks it is most typically defined as a projection of aging biomarkers $f(b) \to R^n$ onto the numerical line, representing chronological age. $f(b)$ is constructed in a way to maximize the probability $P(CA=f(b)|b)$, where CA is the individual's actual chronological age. Thus, comparing the distance between $f(b)$ and CA conveys information on the individual's health status. This is the way biological age is defined in the embodiments of microbiomic clock. However, biological age can also provide an indication of the risk of developing specific health conditions in future, remaining life expectancy or the distance to age-matched counterparts.

For the processes and methods disclosed herein, the operations performed in the processes and methods may be implemented in differing order. Furthermore, the outlined operations are only provided as examples, and some operations may be optional, combined into fewer operations, eliminated, supplemented with further operations, or expanded into additional operations, without detracting from the essence of the disclosed embodiments.

The subject may be human, mammal, animal, plant, or any multicellular organism. Examples of suitable mammals include but are not limited human, monkey, ape, dog, cat, cow, horse, goat, pig, rabbit, mouse and rat.

The biological sample may be any of blood, lymphocyte, monocyte, neutrophil, basophil, eosinophil, myeloid lineage cell, lymphoid lineage cell, bone marrow, saliva, buccal swab, nasal swab, urine, fecal material, hair, breast tissue, ovarian tissue, uterine tissue, cervical tissue, prostate tissue, testicular tissue, brain tissue, neuronal cell, astrocyte, liver tissue, kidney, thyroid tissue, stomach tissue, intestine tissue, pancreatic tissue, vascular tissue, skin, lung tissue, bone tissue, cartilage, ligament, tendon, fat cells, muscle cells, neurons, astrocytes, cultured cells with different passage number, cancer/tumor cells, cancer/tumor tissue, normal cells, normal tissue, any tissue(s) or cell(s) with a nucleus containing genetic material, or genetic material in the form of DNA of a known or unknown subject, such as the microbe markers described herein.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

Figure 6:
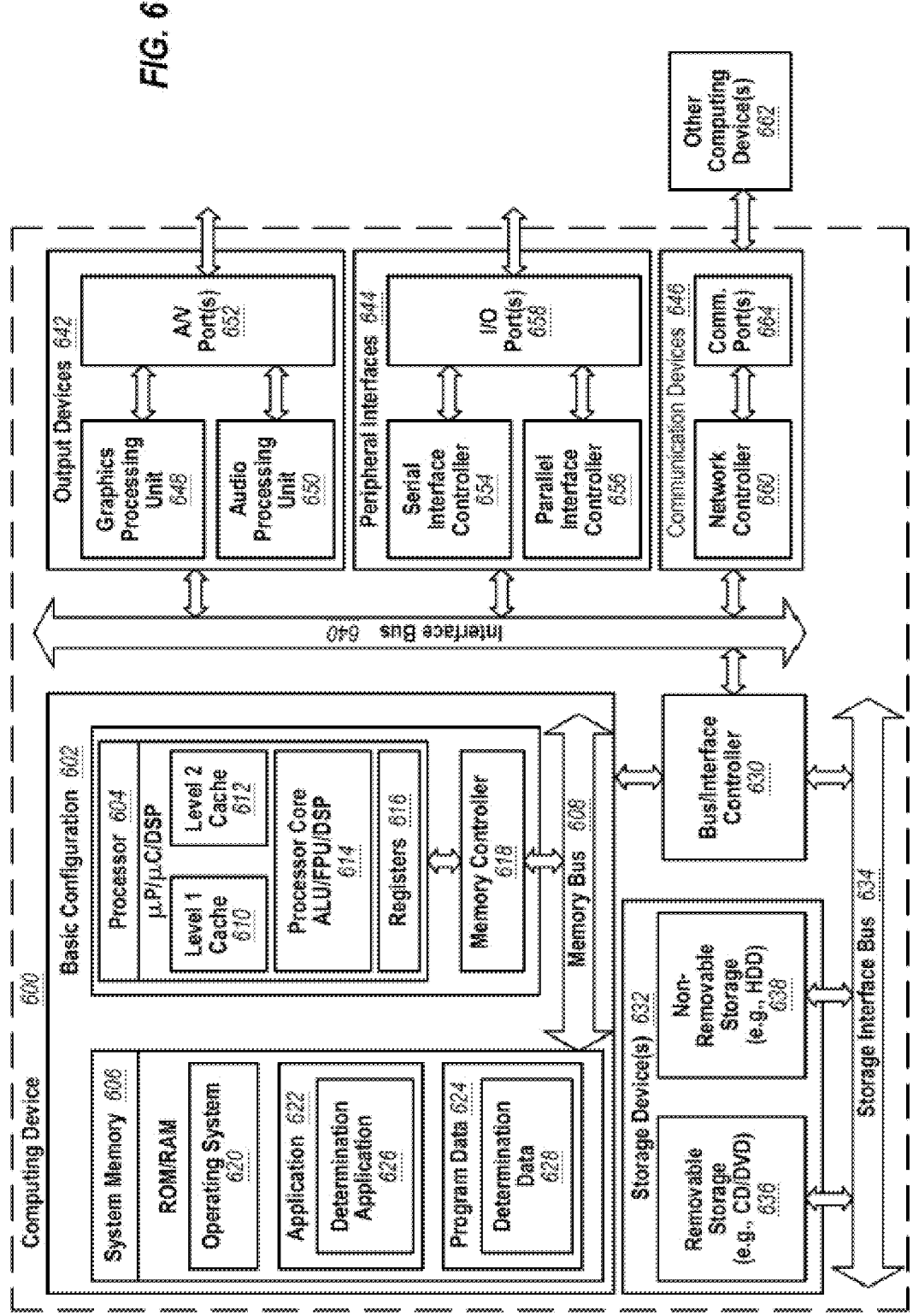
FIG. 6 illustrates a computer or computing system that can be used in the methods described herein.

FIG. 6 shows an example computing device 600 (e.g., a computer) that may be arranged in some embodiments to perform the methods (or portions thereof) described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor (µP), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations, memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, including those described with respect to methods described herein. The determination application 626 can obtain data, such as pressure, flow rate, and/or temperature, and then determine a change to the system to change the pressure, flow rate, and/or temperature.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and non-volatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

This patent application cross-references: U.S. Ser. No. 16/415,855 filed May 17, 2019; U.S. Ser. No. 16/104,391 filed Aug. 17, 2018; U.S. Ser. No. 16/044,784 filed Jul. 25, 2018; U.S. No. 62/536,658 filed Jul. 25, 2017; and U.S. No. 62/547,061 filed Aug. 17, 2017, wherein each application is incorporated herein by specific reference in its entirety.

All references recited herein are incorporated herein by specific reference in their entirety.

REFERENCES

Blalock, Eric M., Kuey-Chu Chen, Keith Sharrow, James P. Herman, Nada M. Porter, Thomas C. Foster, and Philip W. Landfield. 2003. "Gene Microarrays in Hippocampal Aging: Statistical Profiling Identifies Novel Processes Correlated with Cognitive Impairment." *The Journal of Neuroscience: The Official Journal of the Society for Neuroscience* 23 (9): 3807-19.

Chowers, Itay, Dongmei Liu, Ronald H. Farkas, Tushara L. Gunatilaka, Abigail S. Hackam, Steven L. Bernstein, Peter A. Campochiaro, Giovanni Parmigiani, and Donald J. Zack. 2003. "Gene Expression Variation in the Adult Human Retina." *Human Molecular Genetics* 12 (22): 2881-93.

Hong, Mun-Gwan, Amanda J. Myers, Patrik K. E. Magnusson, and Jonathan A. Prince. 2008. "Transcriptome-Wide Assessment of Human Brain and Lymphocyte Senescence." *PloS One* 3 (8): e3024.

Horvath, Steve. 2013. "DNA Methylation Age of Human Tissues and Cell Types." *Genome Biology* 14 (10): R115.

Horvath, Steve, Yafeng Zhang, Peter Langfelder, René S. Kahn, Marco P. M. Boks, Kristel van Eijk, Leonard H. van den Berg, and Roel A. Ophoff. 2012. "Aging Effects on DNA Methylation Modules in Human Brain and Blood Tissue." *Genome Biology* 13 (10): R97.

Magalhães, João Pedro de, João Curado, and George M. Church. 2009. "Meta-Analysis of Age-Related Gene Expression Profiles Identifies Common Signatures of Aging." *Bioinformatics* 25 (7): 875-81.

Mendelsohn, Andrew R., and James W. Larrick. 2013. "The DNA Methylome as a Biomarker for Epigenetic Instability and Human Aging." *Rejuvenation Research* 16 (1): 74-77.

Park, Sang-Kyu, Kyoungmi Kim, Grier P. Page, David B. Allison, Richard Weindruch, and Tomas A. Prolla. 2009. "Gene Expression Profiling of Aging in Multiple Mouse Strains: Identification of Aging Biomarkers and Impact of Dietary Antioxidants." *Aging Cell* 8 (4): 484-95.

Park, Sang-Kyu, and Tomas A. Prolla. 2005. "Gene Expression Profiling Studies of Aging in Cardiac and Skeletal Muscles." *Cardiovascular Research* 66 (2): 205-12.

Weindruch, Richard, Tsuyoshi Kayo, Cheol-Koo Lee, and Tomas A. Prolla. 2002. "Gene Expression Profiling of Aging Using DNA Microarrays." *Mechanisms of Ageing and Development* 123 (2-3): 177-93.

Welle, Stephen, Andrew I. Brooks, Joseph M. Delehanty, Nancy Needler, and Charles A. Thornton. 2003. "Gene Expression Profile of Aging in Human Muscle." *Physiological Genomics* 14 (2): 149-59.

Wesolowska-Andersen, Agata, Martin Iain Bahl, Vera Carvalho, Karsten Kristiansen, Thomas Sicheritz-Pontén, Ramneek Gupta, and Tine Rask Licht. 2014. "Choice of Bacterial DNA Extraction Method from Fecal Material Influences Community Structure as Evaluated by Metagenomic Analysis."*Microbiome* 2 (June): 19.

Wolters, Stefanie, and Björn Schumacher. 2013. "Genome Maintenance and Transcription Integrity in Aging and Disease." *Frontiers in Genetics* 4. https://doi.org/10.3389/fgene.2013.00019.

Zahn, Jacob M., Suresh Poosala, Art B. Owen, Donald K. Ingram, Ana Lustig, Arnell Carter, Ashani T. Weeraratna, et al. 2007. "AGEMAP: A Gene Expression Database for Aging in Mice." *PLoS Genetics* 3 (11): e201.

The invention claimed is:

1. A method of creating a predicted biological aging clock for a subject, the method comprising:
   (a) analyzing DNA from a sample of a microbiota from the gut of the subject to determine an amount of each microorganism in a plurality of microorganisms in the sample of the microbiota of the subject to obtain a biomarker signature;
   (b) creating input vectors based on the biomarker signature;
   (c) inputting the input vectors into a machine learning platform having a deep neural network;
   (d) generating a predicted biological aging clock of the subject based on the input vectors that are inputted into the machine learning platform, wherein the biological aging clock is specific to the subject; and
   (e) preparing a report that includes the predicted biological aging clock, wherein the predicted biological aging clock is indicative of a predicted biological age of the subject.

2. The method of claim 1, wherein the sample of the microbiota of the subject is at least part of a stool sample of the subject.

3. A method of predicting a biological age of a subject based on a taxonomic profile of a microbiota of the subject, the method comprising:
analyzing DNA from a sample of the microbiota of the subject to determine an amount of each microorganism in a plurality of microorganisms in the sample of the microbiota of the subject to obtain the taxonomic profile of the microbiota of the subject, wherein the taxonomic profile is based on the amount of each microorganism in the sample of the microbiota of the subject, wherein the sample is from a gut of the subject;
processing the taxonomic profile of the microbiota with a computer configured with a machine learning platform having a deep neural network;
predicting the biological age of the subject based on output of the processed taxonomic profile; and
generating a report with the predicted biological age of the subject.

4. The method of claim 3, wherein the amount of each microorganism in the sample of microbiota of the subject is determined by analyzing a plurality of microorganism nucleic acids of the plurality of microorganisms from the sample of the microbiota of the subject.

5. The method of claim 3, wherein the taxonomic profile identifies a specific group of microorganisms.

6. The method of claim 5, wherein the specific group of microorganisms includes: Group 95; Group 76; Group 39; Group 41; Group 16; Geroprotective Group; Progeroid Group; or combinations thereof.

7. The method of claim 6, wherein the specific group of microorganisms includes: Group 39 or Group 41.

8. The method of claim 3, wherein the processing the taxonomic profile of the microbiota results in defining an amount of each microorganism relative to the total amount of microorganisms in the microbiota.

9. The method of claim 8, further comprising generating a species level taxonomic profile of the microbiota of the subject based on the amount of each of the microorganisms.

10. The method of claim 9, wherein the relative amount of each of the microorganisms is quantified on the basis of a metagenome.

11. The method of claim 3, further comprising:
accessing a database with a plurality of reference subject microorganism taxonomic profiles of a plurality of reference subjects, each profile linked to a biological age of one of the subjects; and
comparing the taxonomic profile of the microbiota of the subject with the plurality of reference microorganism taxonomic profiles.

12. The method of claim 3, further comprising:
determining an altered taxonomic profile to reduce the predicted biological age of the subject into a younger predicted biological age range than the predicted biological age of the subject; and
including the altered taxonomic profile in the report provided to the subject.

13. The method of claim 12, further comprising:
determining a treatment method for obtaining the altered taxonomic profile of the subject to obtain a younger predicted biological age range in the subject; and
providing the treatment method in the report.

14. The method of claim 3, further comprising:
determining at least one microorganism that when there is a change in amount provides an altered taxonomic profile that is predicted to reduce the predicted biological age of the subject into a younger predicted biological age range than the predicted biological age of the subject; and
providing information about the determined at least one microorganism in the report.

15. The method of claim 3, further comprising:
receiving the biological sample having the microbiota of the subject; and
isolating the plurality of microorganism nucleic acids of microorganisms from the sample of the microbiota of the subject.

16. The method of claim 3, further comprising:
analyzing a plurality of microorganism nucleic acids from a plurality of reference subjects, wherein a first plurality of microorganism nucleic acids of the plurality of microorganism nucleic acids are analyzed for each subject;
determining amounts of each of the microorganisms of the microbiota of each reference subject based on the plurality of microorganism nucleic acids;
generating a taxonomic profile of the microbiota of each reference subject based on the amount of each of the microorganisms of each reference subject;
processing the taxonomic profile of the microbiota of each reference subject with the computer configured with a machine learning platform and thereby predicting the biological age of each reference subject; and
saving the predicted biological age and associated taxonomic profile for each reference subject in a reference database with the predicted biological age associated with the taxonomic profile of the microbiota for each reference subject.

17. The method of claim 16, further comprising:
generating a computer program product stored on a tangible, non-transitory memory device of the computer that when executed causes the computer to:
access the reference database;
compare the subject's taxonomic profile with the reference database;
provide information on at least one microorganism that modulates the predicted biological age associated with the subject;
generate the report with the provided information; and
cause the report to be provided to the subject.

18. The method of claim 3, further comprising:
creating input vectors based on the taxonomic profile;
inputting the input vectors into the machine learning platform;
generating a predicted biological aging clock of the subject based on the input vectors inputted into the machine learning platform, wherein the biological aging clock is specific to the subject; and
preparing the report to include the biological aging clock and identifying the predicted biological age of the subject based on the microbiota.

19. The method of claim 3, further comprising:
providing an internet application to a computer of the subject;
receiving input from the internet application to obtain the report for the subject;
associating the generated report with the subject; and
providing the generated report to the internet application on the computer.

20. The method of claim 19, further comprising:
providing a selectable selection to the internet application;
receiving a selected selection input from the internet application, the selected selection input being obtained from the subject selecting the selectable selection;
identifying information regarding the predicted biological age from the selected selection input; and
providing the information regarding the predicted biological age to the internet application on the computer of the subject.

21. The method of claim 20, further comprising at least one of:
- providing information about the types of microorganisms in the microbiota;
- providing dietary information about how to increase specific microorganisms of the microbiota;
- providing dietary information about how to decrease specific microorganisms of the microbiota;
- providing health information about microbiota for a defined age range for a reference group of microbiota;
- providing information about reference subjects having similar microbiota taxonomic profiles; or
- providing a sequence of a plurality of predicted biological ages for the subject,
wherein the providing is over the internet to the internet application on the computer of the subject.

* * * * *